(12) United States Patent
Forsell

(10) Patent No.: US 10,695,207 B2
(45) Date of Patent: Jun. 30, 2020

(54) METHOD AND INSTRUMENT FOR TREATING OBESITY

(71) Applicant: Peter Mats Forsell, Bouveret (CH)

(72) Inventor: Peter Mats Forsell, Bouveret (CH)

(*) Notice: Subject to any disclaimer, the term of this patent is extended or adjusted under 35 U.S.C. 154(b) by 394 days.

(21) Appl. No.: 14/743,126

(22) Filed: Jun. 18, 2015

(65) Prior Publication Data

US 2016/0022462 A1    Jan. 28, 2016

Related U.S. Application Data

(63) Continuation of application No. 12/865,071, filed as application No. PCT/SE2009/000043 on Jan. 29, 2009, now Pat. No. 9,060,771.

(Continued)

(30) Foreign Application Priority Data

Oct. 10, 2008   (SE) ...................................... 0802138

(51) Int. Cl.
*A61F 5/00* (2006.01)
*A61B 17/00* (2006.01)
(Continued)

(52) U.S. Cl.
CPC ................ *A61F 5/003* (2013.01); *A61B 1/04* (2013.01); *A61B 1/2736* (2013.01); *A61B 1/3132* (2013.01); *A61B 17/00* (2013.01); *A61B 17/00234* (2013.01); *A61B 17/0469* (2013.01); *A61B 17/064* (2013.01); *A61B 17/068* (2013.01); *A61B 17/08* (2013.01); *A61B 17/30* (2013.01); *A61B 17/320016* (2013.01); *A61B 17/3423* (2013.01); *A61B 17/3474* (2013.01); *A61F 2/04* (2013.01); *A61F 5/0003* (2013.01); *A61F 5/004* (2013.01); *A61F 5/005* (2013.01); *A61F 5/0013* (2013.01); *A61F 5/0026* (2013.01); *A61F 5/0033* (2013.01); *A61F 5/0036* (2013.01); *A61F 5/0043* (2013.01); *A61F 5/0046* (2013.01); *A61F 5/0069* (2013.01); *A61F 5/0073* (2013.01); *A61F 5/0079* (2013.01); *A61F 5/0086* (2013.01); *A61F 5/0089* (2013.01); *A61N 1/36007* (2013.01); *A61B 17/0682* (2013.01);
(Continued)

(58) Field of Classification Search
CPC ..... A61B 17/0469; A61B 17/068; A61F 2/04; A61F 5/0033; A61F 5/0036; A61F 5/004; A61F 5/0043; A61F 5/0046; A61F 5/0069
See application file for complete search history.

(56) References Cited

U.S. PATENT DOCUMENTS 6,067,991 A * 5/2000 Forsell .................. A61F 5/0053
128/899
6,461,293 B1 * 10/2002 Forsell .................. A61F 2/0036
128/899

(Continued)

*Primary Examiner* — Sean P Dougherty

(57) ABSTRACT

A surgical or laparoscopic method of treating obesity of a patient using a device adapted to stretch a portion of the stomach wall of said patient. The method comprising the steps of: cutting a hole in the abdominal wall of said patient, dissecting an area around the stomach, placing said device in contact with the stomach, and fixating, direct or indirect, through invagination of the stomach wall, said device to the stomach wall such that said device can stretch a portion of said stomach wall.

11 Claims, 37 Drawing Sheets

Related U.S. Application Data

(60) Provisional application No. 61/006,719, filed on Jan. 29, 2008.

(51) Int. Cl.

| | | |
|---|---|---|
| *A61B 17/04* | (2006.01) | |
| *A61B 17/068* | (2006.01) | |
| *A61N 1/36* | (2006.01) | |
| *A61F 2/04* | (2013.01) | |
| *A61B 17/08* | (2006.01) | |
| *A61B 1/273* | (2006.01) | |
| *A61B 1/04* | (2006.01) | |
| *A61B 1/313* | (2006.01) | |
| *A61B 17/064* | (2006.01) | |
| *A61B 17/32* | (2006.01) | |
| *A61B 17/34* | (2006.01) | |
| *A61B 17/30* | (2006.01) | |

(52) U.S. Cl.
CPC ........... *A61B 2017/00278* (2013.01); *A61B 2017/00561* (2013.01); *A61B 2017/00818* (2013.01); *A61B 2017/00827* (2013.01); *A61B 2017/081* (2013.01); *A61B 2017/306* (2013.01); *A61B 2017/308* (2013.01); *A61F 5/0076* (2013.01); *A61F 2002/044* (2013.01); *A61F 2002/045* (2013.01); *A61F 2005/002* (2013.01); *A61F 2005/0016* (2013.01); *A61F 2005/0023* (2013.01); *A61F 2250/0001* (2013.01); *A61F 2250/0004* (2013.01)

(56) References Cited

U.S. PATENT DOCUMENTS

| | | | | |
|---|---|---|---|---|
| 6,470,892 B1* | 10/2002 | Forsell | ............... | A61B 17/1322 128/899 |
| 6,966,875 B1* | 11/2005 | Longobardi | ............ | A61F 5/005 600/31 |
| 6,981,978 B2* | 1/2006 | Gannoe | ............ | A61B 17/00234 128/898 |
| 6,994,715 B2* | 2/2006 | Gannoe | ............. | A61B 17/0401 606/151 |
| 7,017,583 B2* | 3/2006 | Forsell | ................. | A61F 2/0036 128/899 |
| 2002/0183768 A1* | 12/2002 | Deem | ................. | A61B 17/064 606/151 |
| 2004/0024386 A1* | 2/2004 | Deem | ................. | A61B 17/064 606/1 |
| 2004/0092892 A1* | 5/2004 | Kagan | ...................... | A61F 2/04 604/264 |
| 2005/0096673 A1* | 5/2005 | Stack | ................. | A61B 17/0469 606/151 |
| 2005/0245957 A1* | 11/2005 | Starkebaum | .......... | A61F 5/0069 606/191 |
| 2005/0261712 A1* | 11/2005 | Balbierz | .......... | A61B 17/12009 606/153 |
| 2005/0266042 A1* | 12/2005 | Tseng | ........................ | A61F 2/07 424/423 |
| 2006/0257446 A1* | 11/2006 | Tropsha | ................. | A61B 17/12 424/423 |
| 2006/0271088 A1* | 11/2006 | Alfrhan | ................... | A61F 5/003 606/192 |
| 2007/0027493 A1* | 2/2007 | Ben-Haim | ......... | A61N 1/36007 607/40 |
| 2007/0162059 A1* | 7/2007 | Gannoe | ............ | A61B 17/00234 606/153 |
| 2007/0179556 A1* | 8/2007 | Ben Haim | ............. | A61B 5/053 607/40 |
| 2007/0219571 A1* | 9/2007 | Balbierz | ............... | A61F 5/0036 606/153 |
| 2007/0250020 A1* | 10/2007 | Kim | ........................ | A61F 5/003 604/264 |
| 2007/0250103 A1* | 10/2007 | Makower | ................. | A61B 5/42 606/192 |
| 2007/0276432 A1* | 11/2007 | Stack | .................. | A61B 17/0469 606/151 |
| 2008/0009680 A1* | 1/2008 | Hassler, Jr. | ........... | A61F 5/0053 600/300 |
| 2008/0015406 A1* | 1/2008 | Dlugos | ................ | A61F 5/0003 600/37 |
| 2008/0051823 A1* | 2/2008 | Makower | ........... | A61B 17/1285 606/192 |
| 2008/0147112 A1* | 6/2008 | Sheets | ............. | A61B 17/00491 606/205 |
| 2009/0012372 A1* | 1/2009 | Burnett | .................. | A61B 5/076 600/300 |
| 2009/0012554 A1* | 1/2009 | Makower | ................. | A61B 5/42 606/191 |
| 2009/0118749 A1* | 5/2009 | Shalon | .................. | A61F 5/0079 606/157 |
| 2010/0114124 A1* | 5/2010 | Kelleher | ................ | A61B 17/10 606/151 |
| 2010/0305468 A1* | 12/2010 | Policker | ............. | A61N 1/36007 600/547 |

* cited by examiner

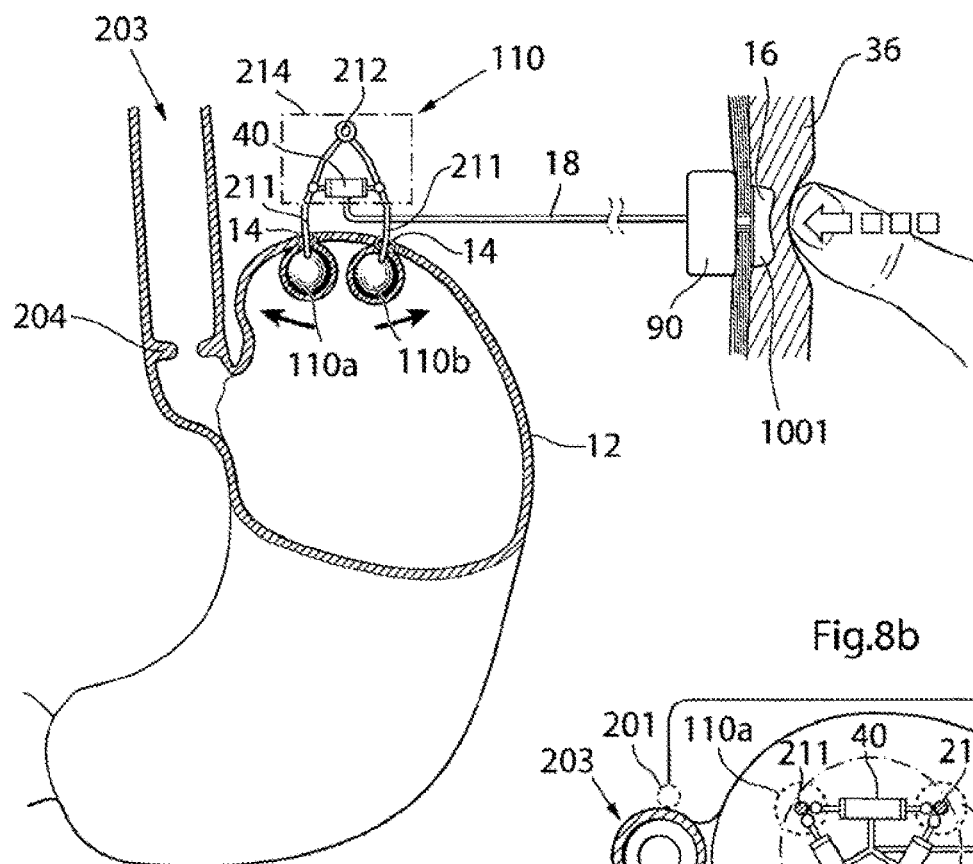
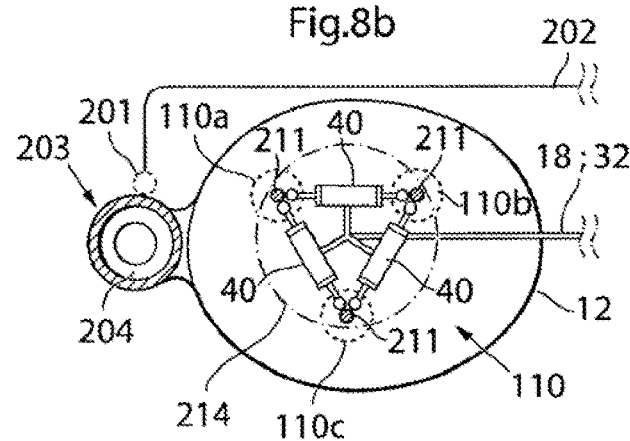
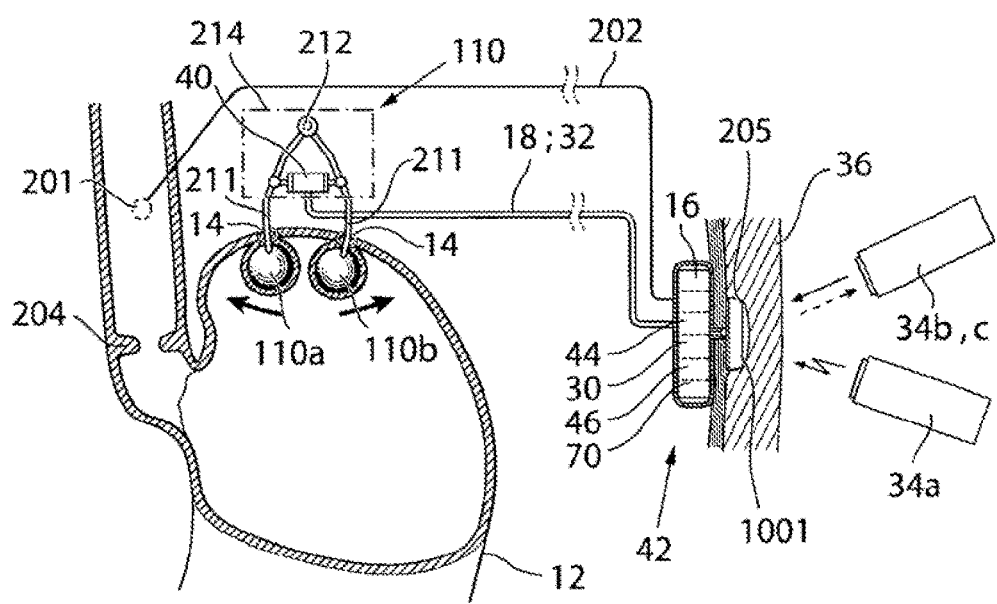

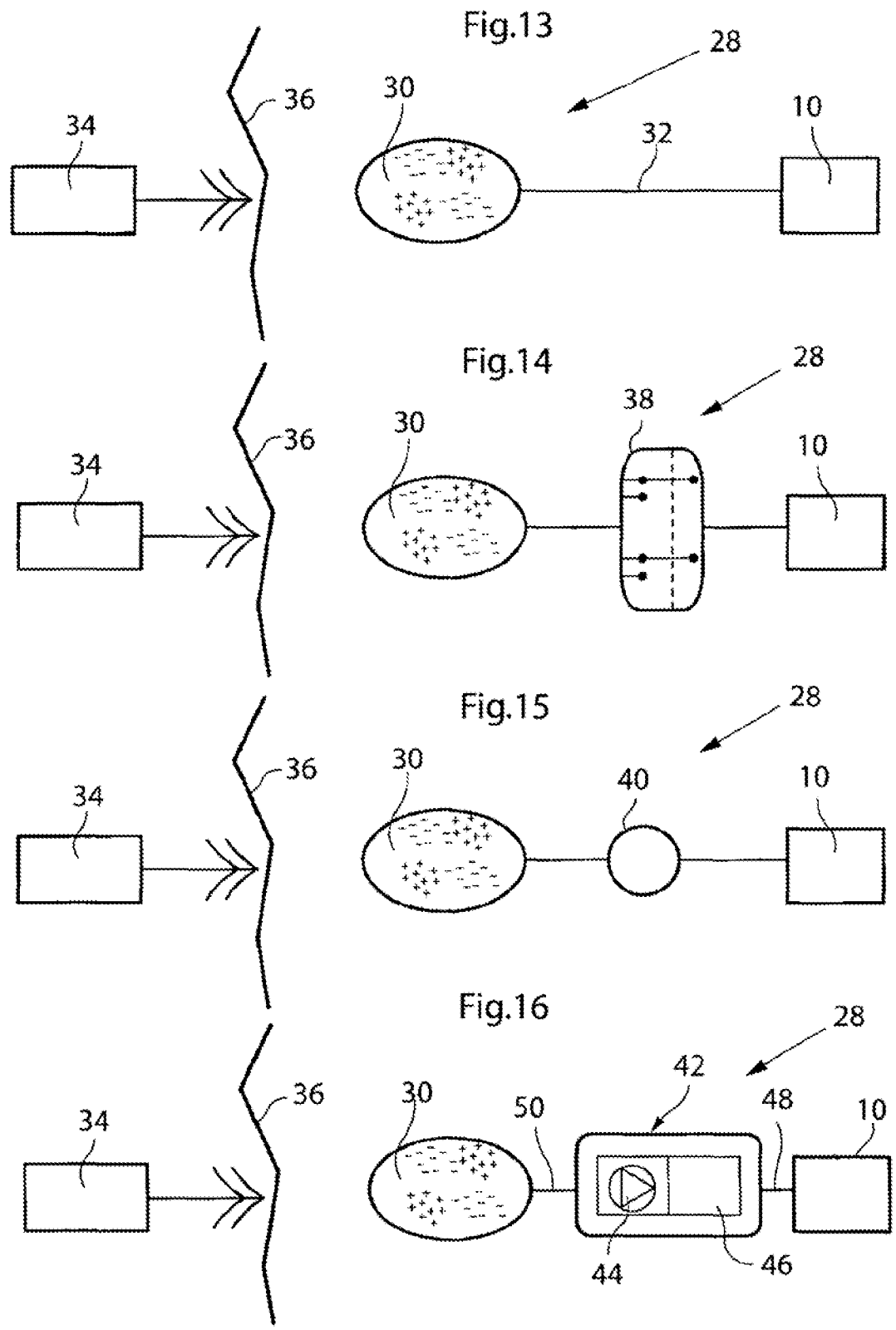

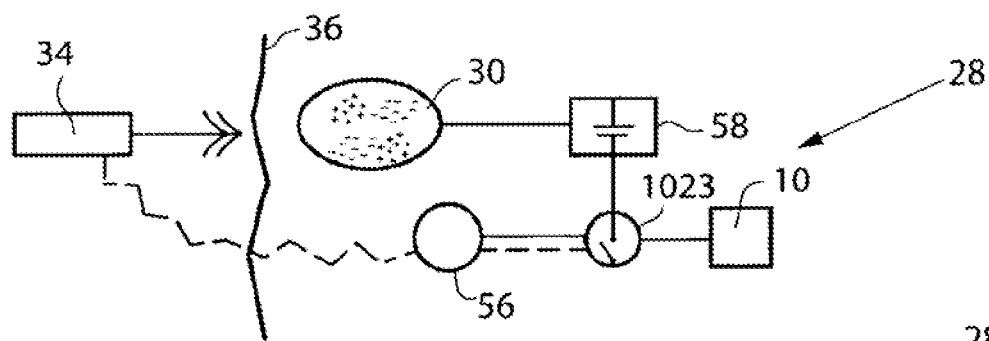
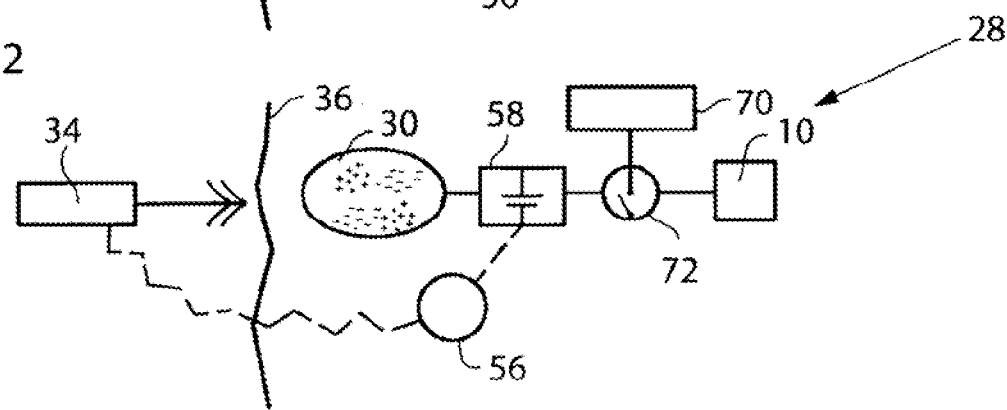
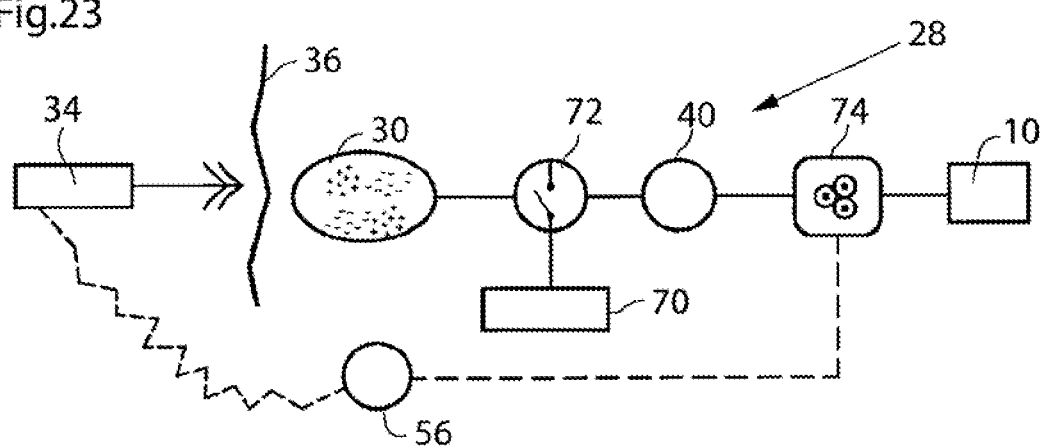
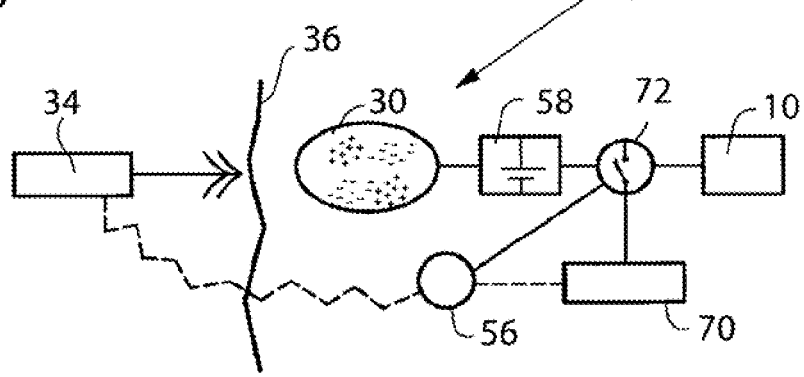

METHOD AND INSTRUMENT FOR TREATING OBESITY

This application is a continuation of U.S. patent application Ser. No. 12/863,071 filed. Jul. 28, 2010, issued as U.S. Pat. No. 9,060,771 on Jun. 23, 2015, which is the US national phase of International Application No. PCT/SE09/00043, filed Jan. 29, 2009, which designates the US and claims priority to Swedish Application No. 0802138-8 filed Oct. 10, 2008, and which claims the benefit of U.S. Provisional No. 61/006,719 filed on Jan. 29, 2008, the entire contents of each of which are hereby incorporated by reference.

TECHNICAL FIELD

The present invention relates to an device, a system, and a method for treating obesity.

BACKGROUND

In the past, obese patients have been treated by gastric reduction surgery to restrict the food intake of the patient. At present, two gastric restriction procedures for treating obesity are most commonly performed, namely Adjustable Gastric Banding (AGB) and Vertical Banded Gastroplasty (VBG).

In AGB, a constricting hand is placed completely around an obese patient's surgically intact stomach near the upper end thereof, just below the junction of stomach and esophagus, to restrict the food intake of the patient. As the band constricts the stomach, a small gastric pouch is formed above the band and a reduced permanent stoma in the stomach. The idea being that a small amount of food filling the small pouch causes the patient to sense fullness, i.e., satiety. Examples of AGB are disclosed in U.S. Pat. No. 4,592,339 and European Patent No. 0611561, In VBG, typically the stomach is stapled vertically with four rows of linear staples, which compartmentalize the stomach into an elongate proximal smaller compartment adjacent the esophagus and a distal larger compartment, so that the volume of the smaller compartment is about 10% of the volume of the stomach. A circular hole is punched-out in the stomach at the lower end of the rows of linear staples and several circular rows of staples are placed on the stomach around the circular hole. A band is placed through the circular hole and is secured around the stomach, whereby the band defines a narrow outlet opening from the smaller compartment into the larger compartment of the stomach. Once secured, the band prevents the stomach from stretching at the outlet opening, which results in that the outlet opening over time maintains its initial small diameter. Food that the patient takes in is held up in the smaller compartment causing the sensation of fullness. Then, the food empties slowly through the outlet opening into the larger compartment where digestion takes place normally. Examples of VBG are disclosed in U.S. Pat. Nos. 5,345,949 and 5,549,621.

There are few complications associated with AGB and VBG. However, it is important that the patient very carefully Chews food completely before swallowing it, so that food pieces collected in the smaller compartment of the stomach are able to pass through the narrow outlet opening of the smaller compartment. If food pieces were stuck in the outlet opening it might cause the patient to vomit and feel sick. In such a case the patient should have to visit a doctor or nurse.

Another complication associated with AGB and VBG is that the patient may suffer from acid stomach reflux at night.

The use of electrical stimulation of the stomach wall to cause the patient to feel satiety has also been used.

SUMMARY

A surgical or laparoscopic method of treating obesity of a patient using a device adapted to stretch a portion of the stomach wall of the patient is provided. The method comprises the steps of: cutting a hole in the abdominal wall of the patient, dissecting an area around the stomach, placing the device in contact with the stomach, and fixating, direct or indirect, through invagination of the stomach wall the device to the stomach wall such that the device can stretch a portion of the stomach wall.

According to one embodiment the method the step of fixating the device comprises the steps of fixating a first portion of the device to a first part of the stomach wall, and fixating a second portion of the device to a second part of the stomach wall, wherein the first and second portion of the device is fixated, such that the device is adapted to stretch a portion of the stomach wall between the first and second part of the stomach wall.

According to another embodiment, the device is a first device, and the method comprises the additional steps of: fixating direct or indirect through invagination of the stomach wall a second device adapted to stretch a part of the stomach wall in contact with the stomach, fixating the second device to the stomach wall, stretching a first portion of the stomach wall using the first device, and stretching a second portion of the stomach wall using the second device.

According to another embodiment the method comprises the additional step of postoperatively and non-invasively regulating the device to stretch a portion of the stomach wall to affect the appetite of the patient.

A surgical or laparoscopic method of treating obesity of a patient using a device adapted to stretch a portion of the stomach wall of the patient is further provided. The method comprises the steps of inserting a needle or tube like instrument into the abdomen of the patients body, using the needle or tube like installment to fill the patient's body with gas, placing at least two laparoscopic trocars in the patient's body, inserting a camera through one of the laparoscopic trocars in the patient's body, inserting at least one dissecting tool through one of the at least two laparoscopic trocars, dissecting an area of the stomach, introducing a device into the abdominal cavity, placing the device on the outside of the stomach wall, engaging the stomach wall.

According to another embodiment the method comprises the step of postoperatively and noninvasively regulating the device to stretch a part of the stomach wall comprises the step of increasing the distance between the first part of the stomach wall and the second part of the stomach wall.

According to another embodiment the step of regulating, the device is performed from outside the patient's body.

According to another embodiment the step of regulating the device comprises from time to time regulate different device to at a first time stretch a first portion of the stomach wall and at a second time stretch a second portion of the stomach wall.

According to another embodiment the method comprises placing two or more device in contact with the stomach and from time to time regulate different device to stretch a portion of the stomach wall. The step of fixating, the first and second portion of the device could further comprise the step of invaginating, the first and second portion with stomach to stomach sutures or staplers.

According to another embodiment, the device further comprises an implantable control unit, wherein the method step of regulating the device comprises regulating the device by the implantable control unit from inside the body.

According to another embodiment the stretching of the second portion comprises the step of:

time delaying stretching the second part, with a predetermined time delay.

Manual

According to another embodiment the step of placing a device in contact with the stomach comprises placing a device adapted to have, a variable, volume in contact with the stomach, which could be regulated by means of at least one moveable wall portion, which in turn could be an elastic wall portion. The device could have an essentially round shape, or egg shape.

According to another embodiment the device comprises a subcutaneous switch, and the method further comprises pressing the switch for manually and non-invasively regulating the device. Regulating the device could comprise the step of moving a fluid front a reservoir to the device.

According to another embodiment the device further comprises a pump, and the method further comprises the step of pumping a fluid from the reservoir to the device to stretch the stomach wall.

According to another embodiment the step of moving a fluid from a reservoir to the device comprises the step of moving a wall portion of the reservoir, which could be done through the step of manually pressing the reservoir.

The reservoir, according to any of the embodiments could be placed subcutaneously or in the abdomen.

Mechanical

According to another embodiment the step of increasing the distance between the first part of the stomach wall and the second part of the stomach wall comprises the step of moving fluid into a chamber having a variable volume.

Automatic

According to another embodiment the step of placing a device in contact with the stomach comprises placing a device adapted to have a variable volume in contact with the stomach.

The device adapted to have a variable volume could comprise at least one moveable wall portion, which in turn could be an elastic wall portion.

The device according to any of the embodiments could comprise a subcutaneous switch, and the method could further comprise pressing the switch for noninvasively regulating the device.

According to another embodiment the step of regulating the device comprises the step of moving a fluid from a reservoir to the device. The step of moving a fluid from a reservoir to the device could comprise the steps of: operating a pumping device, for moving the fluid from the reservoir to the device, and the device expanding in volume and thereby stretching the portion of the stomach wall.

According to another embodiment the method further comprises the step of the fluid flowing hack from the device to the reservoir, thereby releasing the stretching of the stomach wall.

According to another embodiment the method further comprises the step of: sensing a variable using an implantable sensor, interpreting the sensed variable, using the interpreted variable to control the device.

According to another embodiment the step of controlling the device comprises the steps of: operating a pumping device, for moving the fluid from a reservoir to the device, and the device expanding in volume and thereby stretching the portion of the stomach wall.

According to another embodiment the method further comprises the step of the fluid flowing back from the device to the reservoir thereby releasing the stretching of the stomach wall.

The step of sensing a variable could comprise the step of sensing a variable connected to the food intake of the patient, which could result in an increased stretching of the stomach portion, and thereby the feeling of satiety by the patient.

Mechanical

According to another embodiment the step of increasing the distance between the first part of the stomach wall and the second part of the stomach wall could comprise the step of moving thud into a chamber having a variable volume.

According to another embodiment the step moving fluid into a chamber comprises the step of moving fluid from a reservoir to the chamber having a variable volume.

According to another embodiment the step of moving a fluid from a reservoir to the device comprises the steps of: operating a pumping device, the pumping device moving the fluid from the reservoir to the device, and the device expanding in volume and thereby stretching the portion of the stomach wall.

According to another embodiment the step of operating the pumping device comprises the step of operating the pumping device using a wireless remote control.

According to another embodiment the method further comprises the step of the fluid flowing back from the device to the reservoir thereby releasing the stretching of the stomach wall.

According to another embodiment the step of increasing the distance between the first part of the stomach wall and the second part of the stomach wall comprises the step of operating a motor adapted increase the distance between the first part of the stomach wall and the second part of the stomach wall, thereby stretching a portion of the stomach wall.

The step of operating the motor could comprise the step of operating the motor using a wireless remote control.

According to another embodiment the method could further comprises the step of: sensing a variable using an implantable sensor, interpreting the sensed variable, using the interpreted variable to control the device.

According to another embodiment the step of controlling the device could comprise the steps of operating a pumping device, for moving the fluid from a reservoir to the chamber, and the chamber being filled with the fluid increasing the distance between the first part of the stomach wall and the second part of the stomach wall and thereby stretching the portion of the stomach wall.

According to another embodiment the method further comprise the step of the fluid flowing back from the device to the reservoir thereby releasing the stretching of the stomach wall.

According to another embodiment the step of sensing a variable comprises the step of sensing a variable connected to the food intake of the patient.

According to another embodiment the method further comprises the step of sensing a variable using an implantable sensor, interpreting the sensed variable, using the interpreted variable to control the device. The step of sensing a variable could comprise the step of sensing a variable connected to the food intake of the patient. The step of increasing the distance between the first part of the stomach wall and the second part of the stomach wall could comprise the step of operating a mechanical device adapted increase the distance between the first part of the stomach wall and the second part of the stomach wall, thereby stretching a portion of the stomach wall. The first and second portions of the device could comprise mechanical members adapted to move for stretching a portion of the stomach wall between the first and second part of the stomach wall.

According to another embodiment the method comprises a motor, wherein the mechanical members is moving for stretching a portion of the stomach wall using the motor.

According to another embodiment the step of stretching a portion of the stomach wall comprises the step of operating at least one mechanical device for stretching a portion of the stomach wall.

According to another embodiment the step of invaginating the mechanical device in the stomach wall comprises invaginating with stomach to stomach sutures.

According to another embodiment the method further comprises the step of expanding the mechanical device in the invaginated stomach wall to stretch the stomach wall.

According to another embodiment the invaginated mechanical device comprises a motor, expanding the invaginated mechanical device.

The device could further comprise a memory metal or a hydraulically controlled mechanical device, expanding the stomach wall.

Placing

According to another embodiment the step of placing a device comprises placing the device in connection with the stomach wall, on the outside thereof, or in the stomach fundus wall, or in connection with the stomach wall, on the inside thereof.

According to another embodiment the step of placing a device in connection with the stomach wall, on the inside thereof could comprise the steps of: cutting a hole in the stomach wall, and inserting the device through the hole in the stomach wall.

According to another embodiment the step of placing a device comprises placing the device in the stomach fundus wall of the patient.

Fixation

According to another embodiment the step of fixating the at least one device comprises suturing or stapling the at least one device to the stomach wall, e.g. by means of stomach-to-stomach sutures or staplers.

The step of fixating the at least one device could comprise placing a mesh adapted to be fixated to the stomach wall by means of fibrotic tissue. The mesh could be additionally supported by sutures or staplers and adapted to promote the growth in of human tissue, such as a net like structure.

Control Unit

According to another embodiment the method could comprise the step of placing a transferring member from the device to a control unit. The transferring member could comprise a fluid transferring member, or a transferring member adapted to transfer electrical power.

According to another embodiment the method further comprises the step of placing the control unit, which could be placed subcutaneously in the patient.

According to another embodiment the step of placing the control unit subcutaneously further comprises the steps of: inserting the control unit into the hole in the abdomen of the patient, and fixating the control unit.

An additional method is also provided, the method comprising the steps of: creating a hole in the stomach wall; introducing the stretching device into the abdomen; moving the device through the hole and placing it on the inside of the stomach wall; creating a pouch of a portion of the stomach wall outside the stomach cavity, with the device placed against the inside of the stomach wall; invaginating the device in the pouch to the stomach wall; and sealing the hole, preferably with sutures or staples.

According to another embodiment the method according to any of the embodiments could comprise the steps of: creating a hole in the stomach wall; moving the device through the hole and placing it on the inside of the stomach wall; introducing the device by means of the instrument into the pouch; and sealing the hole, preferably with sutures or staplers.

According to another embodiment the method further comprises providing a device for regulating the stretching device from the outside of the patient's body; and operating the device to regulate the device.

According to another embodiment the device comprises an implantable control unit and the method further comprises the steps of; providing an implanted control unit for regulating the stretching device from the inside of the patient's body; and operating the device to regulate the device.

The method could further comprise the steps of subcutaneously placing an injection port and connecting a tube connected to the device to the injection port.

According to another embodiment the method further comprises the step of providing a tube connected to the stretching device through the hole and further up to the abdominal wall or passing through the abdominal wall.

According to another embodiment the method further comprises the steps of: receiving a tube from the abdominal cavity of the patient, connected to the stretching device, and filling the device with fluid injected through the tube.

According to another embodiment the method could further comprise the steps of: subcutaneously placing an injection port, and connecting the tube to the injection port.

The method could further comprise the additional step of postoperatively and non-invasively regulating the device to stretch a part of the stomach wall to affect the appetite of the patient.

According to another embodiment the method comprises the additional step of filling the device with a fluid.

According to another embodiment the method could comprise the additional step of placing an internal control unit within the patient's body.

According to one embodiment the method further comprises the additional step of connecting the internal control unit to the device, which could be done hydraulically or using electrical wires.

An additional surgical or laparoscopic method of treating obesity of a patient using a device adapted to stretch a portion of the stomach wall of the patient is provided. The method comprising the steps of: inserting a needle or tube like instrument into the abdomen of the patients body, using the needle or tube like instrument to fill the patient's body with gas, placing at least two laparoscopic trocars in the patient's body, inserting a camera through one of the laparoscopic trocars in the patient's body, inserting at least one dissecting tool through one of the at least two laparoscopic trocars, dissecting an area of the stomach, introducing a device into the abdominal cavity, invaginating the device on the outside of the stomach wall with stomach to stomach sutures or staplers and postoperatively stretching the invaginated stomach wall portion by operating the device.

According to another embodiment the method comprises the additional step of; introducing a second or more device into the abdominal cavity, invaginating the second or more device on the outside of the stomach wall with stomach to stomach sutures or staplers and postoperatively stretching the invaginated stomach wall portion by operating the second or more device.

According to another embodiment the method comprises the additional step of; postoperatively stretching the invaginated stomach wall portion at the first or second or more parts of the device independent from each other.

An additional surgical or laparoscopic method of treating obesity of a patient using a device adapted to stretch a portion of the stomach wall of the patient is provided. The method comprises the steps of: inserting a needle or tube like instrument into the abdomen of the patients body, using the needle or tube like instrument to fill the patient's body with gas, placing at least two laparoscopic trocars in the patient's body, inserting a camera through one of the laparoscopic trocars in the patient's body, inserting at least one dissecting tool through one of the at least two laparoscopic trocars, dissecting an area of the stomach, introducing a device into the abdominal cavity, invaginating a first part of the stretching device placed on the outside of the stomach wall with stomach to stomach sutures or staplers and invaginating a second part of the stretching device, separate from the first part, placed on the outside of the stomach wall with stomach to stomach sutures or staplers and postoperatively stretching the stomach wall portion between the first and second part by operating the device.

According to another embodiment the method comprises the additional step of; introducing a second or more device into the abdominal cavity, invaginating a first part of the stretching second or more device placed on the outside of the stomach wall with stomach to stomach sutures or staplers, invaginating a second part of the second or more stretching device, separate from the first part, placed on the outside of the stomach wall with stomach to stomach sutures or staplers, and postoperatively stretching the stomach wall portion between the first and second part by operating the second or more device.

According to another embodiment the method comprises the additional steps of; invaginating a third or more part of the stretching device placed on the outside of the stomach wall, separate from the first or second part, with stomach to stomach sutures or staplers and postoperatively stretching the stomach wall portion between any combination of the first and second part and third or more parts, by operating the device.

A surgical method of treating obesity of a patient using a device adapted to stretch a portion of the stomach wall of the patient, the method comprising the steps of: cutting the skin of a human patient, dissecting an area of the stomach, introducing a device into the abdominal cavity, invaginating the device on the outside of the stomach wall with stomach to stomach sutures or staplers, and postoperatively stretching the invaginated stomach wall portion by operating the device.

The method could further comprise the additional step of; introducing a second or more device into the abdominal cavity, invaginating the second or more device on the outside of the stomach wall with stomach to stomach sutures or staplers, and postoperatively stretching the invaginated stomach wall portion by operating the second or more device.

According to another embodiment the method comprises the additional steps of; postoperatively stretching the invaginated stomach wall portion at the first or second or more parts of the device independent from each other.

An additional surgical method of treating obesity of a patient using a device adapted to stretch a portion of the stomach wall of the patient is provided. The method comprising the steps of: cutting the skin of a human patient, dissecting an area of the stomach, introducing a device into the abdominal cavity, invaginating a first part of the stretching device placed on the outside of the stomach wall with stomach to stomach sutures or staplers, invaginating a second part of the stretching device, separate from the first part, placed on the outside of the stomach wall with stomach to stomach sutures or staplers, and postoperatively stretching the stomach wall portion between the first and second part by operating the device.

According to another embodiment the method comprises the additional step of; introducing a second or more device into the abdominal cavity, invaginating a first part of the stretching second or more device placed on the outside of the stomach wall with stomach to stomach sutures or staplers, invaginating a second part of the second or more stretching device, separate from the first part, placed on the outside of the stomach wall with stomach to stomach sutures or staplers, and postoperatively stretching the stomach wall portion between the first and second part by operating the second or more device.

According to another embodiment the method further comprises the steps of invaginating a third or more part of the stretching device placed on the outside of the stomach wall, separate from the first or second part, with stomach to stomach sutures or staplers, and postoperatively stretching the stomach wall portion between any combination of the first and second part and third or more parts, by operating the device.

According to another embodiment the method comprises the additional steps of postoperatively and noninvasively regulating the device to stretch a part of the stomach wall to affect the appetite of the patient.

The method according to any embodiment could further comprise the step of filling the device with a fluid.

According to another embodiment the method comprises the additional step of placing an internal control unit within the patient's body, and connecting the internal control unit to the device, which could be done hydraulically or using electrical wires.

Instrument

An instrument for placing a device adapted to stretch a part of the stomach wall of a patient in connection with the stomach wall is further provided. The instrument comprises: a holding member adapted to releaseably hold the device, and a fixating member, adapted to assist in the fixation of the device to the stomach wall, on the outside thereof.

The instrument could further comprise an optical member for viewing in the area of the stomach.

The instrument could comprise a fixation member adapted to suturing the device to the stomach wall, on the outside thereof.

According to another embodiment the fixation member is adapted for stapling the device to the stomach wall, on the outside thereof, and in other embodiments the fixation member is adapted for invaginating at least a part of the device in the stomach wall with stomach-to-stomach sutures, on the outside thereof.

According to another embodiment the fixation member could be adapted for invaginating at least a part of the device in the stomach wall with stomach-to-stomach staplers, on the outside thereof.

An instrument for placing a device adapted to stretch a part of the stomach wall of a patient in connection with the stomach wall is further provided. The instrument comprises: a holding member adapted to releaseably hold the device, an insertion member adapted to insert the device through the stomach wall, and a fixating member, adapted to assist in the fixation of the device to the stomach wall, on the inside thereof.

The instrument could further comprise a cutting member for cutting a hole in the stomach wall, an optical member for viewing in the area of the stomach. The fixation member could be adapted for suturing the device to the stomach wall, on the inside thereof, or for stapling the device to the stomach wall, on the inside thereof, or for invaginating at least a part of the device in the stomach wall with stomach-to-stomach sutures, on the inside thereof, or for invaginating at least a part of the device in the stomach wall with stomach-to-stomach staplers, on the inside thereof.

The instrument could further comprise a special holding device, which could comprise a special holding device adapted to hold the stomach using vacuum or using mechanical holding members.

These objects and others are obtained by device described in the appended claims. Thus, by providing a device that comprises at least one operable stretching device implantable in an obese patient and adapted to stretch a portion of the patient's stomach wall, and an operation device for operating the stretching device when implanted to stretch the stomach wall portion such that satiety is created, a device for treating obesity is obtained. The present invention is based on the realization that by creating a stretching effect of the stomach wall a feeling of satiety is created. As a result, there is no need for providing a reduced permanent stoma in the stomach as required by AGB and VBG. Thus, the complications associated with such a reduced stoma are eliminated by the new device of the present invention, which is a simpler, safer and long term working device.

The stretching device may be kept in contact with the stomach wall by stomach-to-stomach sutures or staplers, in a position in which the stretching device is capable of stretching the stomach wall. Specifically, the stretching device may be invaginated by the stomach wall by means of stomach-to-stomach sutures or staplers.

The stretching device may be adapted to be placed in the stomach cavity. To this end, the stretching device may be adapted to be inserted into the stomach cavity via a gastroscope or intraluminar instrument, and be adapted to be attached to the stomach wall by surgery. Alternatively, the stretching device may be adapted to be placed on the outside of the stomach.

In an embodiment of the invention, the stretching device comprises a first engaging member adapted to engage a first part of the stomach wall and a second engaging member adapted to engage a second part of the stomach wall close to but spaced from the first stomach part. The operation device is adapted to operate the first and second engaging member to move away from each other to stretch the stomach wall portion between the first and second parts of the stomach such that satiety is created.

At least one of the first and second engaging members may be adapted to at least in part be invaginated by the stomach wall by stomach-to-stomach sutures or staplers holding the engaging member in place. In addition, at least one of the first and second engaging members may be adapted to be kept in place by sutures or staplers between the engaging member and the stomach wall. Suitably, at least one of the first and second engaging members comprises a tissue growth promoting structure, preferably a net like structure, adapted to be in contact with the stomach wall to secure long term attachment of the stretching device to the stomach wall.

In another embodiment of the invention, the stretching device comprises at least one expandable body adapted to be invaginated by a portion of the patient's stomach wall, and the operation device comprises a fluid reservoir, which is in fluid communication with a chamber of the body. The operation device is non-invasively operable to distribute fluid from the fluid reservoir to the chamber of the body to expand the body such that the stomach wall portion is stretched, when the body is invaginated. The fluid reservoir may be operated by manually pressing it. The operation device may comprise a reverse servo, wherein a small volume of fluid in the fluid reservoir is compressed with a higher force and the chamber of the body creates a movement of a larger total volume with less force per unit of volume. The fluid reservoir may be placed subcutaneously or in the abdomen, and may be regulated by moving a wall of the reservoir, for example by a motor. Alternatively, a pump may be provided for pumping fluid or air from the reservoir to the body's chamber.

The term "reversed servo means" encompasses the definition of a device that is controlled with a higher force and a small stroke i.e. for example movement of a small amount of fluid with a high force controls a larger amount of fluid moving by means of very smaller force, but may alternatively or additionally encompass the definition of a mechanism that transfers a strong force acting on a moving element having a short stroke into a small force acting on another moving element having a long stroke. The reversed servo means is preferably used when manual control of the device through intact skin is possible.

In another embodiment of the invention, the device comprises a large chamber in contact with one or more smaller chambers. The chambers are adapted to communicate with fluid or air being distributed between the chambers. A reversed servo for distributing fluid between the chambers may be provided, wherein a small volume of fluid in the large chamber is compressed with a higher force and the smaller chamber creates a movement of a larger total volume with less force per unit of volume. The large chamber may be adapted to be invaginated in the patient's fundus stomach wall to also treat reflux disease by restricting movement of the cardiac notch towards the diaphragm muscle of the patient, whereas the small chambers function as stretching devices to treat obesity. The large chamber may distribute fluid or air to the small chambers to cause them to expand and stretch the stomach fundus wall.

In another embodiment of the invention, the stretching device comprises a mechanical stretching device, wherein a motor for mechanically regulating the stretching device may be provided. The mechanically regulated stretching device may be adapted to engage a first part of the stomach wall and a second part of the stomach, wherein the mechanically regulated stretching device comprises a joint mechanism adapted to be moved by the operation device. Alternatively, the stretching device may comprise a first engaging member adapted to engage a first part of the stomach wall and a second engaging member adapted to engage a second part of the stomach wall close to but spaced from the first stomach part, wherein the mechanical stretching device regulates the distance between the first and second parts of the stomach wall.

As an alternative, the hydraulic means described above may be used for regulating such a mechanical stretching device by the hydraulic distribution of fluid or air.

The stretching device may be non-invasively adjustable postoperatively.

The operation device for operating the stretching device may in its simplest form comprise a subcutaneous switch adapted to be non-invasively operated by manually pressing the switch for the operation of the stretching device.

At least two operable stretching devices adapted to stretch at least two different portions of the stomach wall may be provided, wherein the device is adapted to be postoperatively and non-invasively regulated. Specifically, the device may be regulated from time to time such that at a first time one of the stretching devices stretches one of the portions of the stomach wall and at a second time the other of the stretching devices stretches the other portion of the stomach wall.

In another embodiment of the invention, the stretching device comprises a body adapted to fill out a volume defined by wall portions of the stomach. The body suitably has rounded contours without too sharp edges that would be damaging to the patient's stomach wall. Where the body is to be invaginated it may have varying circumference to better be kept in place invaginated by stomach wall portions of the patient. The body may be shaped like an egg or like a kidney.

Generally, any kind of mechanical construction may be used. Any mechanical construction driven mechanically or hydraulically or any pneumatic construction may be used. Any motor or any pump or moving material changing form when powered may be used to achieve the simple goal of stretching a part of the stomach wall by moving at least two parts of the stomach wall away from each other.

Any kind of hydraulic operation may be used. It will be appreciated that instead of hydraulic operation, pneumatic operation can be used, wherein air instead of hydraulic fluid is moved between a reservoir and a chamber formed by the stretching device. Preferably the reservoir has a locking position to keep it in the desired position if it is handled by the patient. To compress the reservoir it preferably stays compressed and releases after pressing again.

Any kind of hydraulic solution may be used for the stretching device. The hydraulic solution may be driven by both mechanically and powered with any motor or pump as well as manual.

Of course just expanding an invaginated part of the stomach also stretches away the stomach wall which also may be achieved both mechanically, hydraulically, pneumatically and both being powered with a motor or pump or by manual force.

According to one embodiment, a device for treating obesity of a patient is provided, the device comprises at least one operable stretching device implantable in the patient and adapted to stretch a portion of the patient's stomach wall. The device further comprises an implantable control unit for automatically controlling the operable stretching device, when the control unit and stretching device are implanted, to stretch the stomach wall portion in connection with the patient eating such that satiety is created.

According to another embodiment the device further comprises at least two stretching devices, a first stretching device and a second stretching device, or three or more stretching devices. According to yet another embodiment the device further comprises an operation device for operating the stretching device, wherein the control unit controls the operation device to stretch the stomach wall portion, when the control unit and stretching device are implanted.

According to yet another embodiment the device further comprising a sensing device including a sensor for sensing a physical parameter of the patient or a functional parameter of the stretching device, wherein the sensing device sends information relating to the parameter to the control unit, and the control unit controls the stretching device based on the information. The device could be adapted to control the stretching device to intermittently stretch the stomach wall, when the control unit and stretching device are implanted.

According to one embodiment the implantable control unit is adapted to control the amount of stretching performed by the stretching device on the stomach wall, according to one embodiment by vary over time, the amount of stretching of the stomach wall and/or to stretch the stomach during a predetermined time period.

According to one embodiment the implantable control unit is adapted to control the stretching device based on the patient's food intake, the implantable control unit could be programmable to include any of: a predetermined time period during which the stretching device is controlled to stretch the stomach wall, and the magnitude of stretching applied on the stomach wall. The operation device could be a mechanical operation device, hydraulic operation device, a hydraulically operated mechanical operation device or a mechanically operated hydraulic operation device.

According to one embodiment the sensor of the sensing device senses the patient's food intake directly or indirectly, and the implantable control unit controls the operation device to stretch the stomach wall in response to signals from the sensor.

According to yet another embodiment the implantable control unit is adapted to control the operation device to stretch the stomach wall using more than one stretching device. This could be done by the implantable control unit being adapted to control the first stretching device, during a first time period, to stretch a first portion of the stomach wall, and the second stretching device, during a second time period, to stretch a second portion of the stomach wall different from said first portion of the stomach, to allow longer relaxation of the stomach wall in between stretching periods.

According to one embodiment the sensor of the sensing device is adapted to sense a parameter related to the patients food intake such as esophagus movement, esophagus bending, esophagus motility, esophagus stretching, esophagus pressure, food passing esophagus, food in the stomach, neural activity, vagus activity, muscle activity, hormonal activity, stomach motility, stomach stretching, stomach pressure, stomach bending, stomach filling, and/or acidity in the stomach. The sensing device could also be adapted to senses motility, stretching, bending, pressure, movement, a hormone, neural activity, PH-level, acidity, volume, capacitance, resistance, volt, ampere, light absorption or visualization, ultrasound reflection or absorption, bending metal, bimetal and PH.

According to one embodiment the device further comprises an implantable reservoir, wherein the operation device is hydraulically controlled by the reservoir. The stretching device could be adapted to be controlled from outside the patient's body using a patient control which according to one embodiment could be adapted to override the control of the implantable control unit. The implantable control unit could be adapted to be controlled from outside the patient's body by the patient.

According to one embodiment the device further comprises an external control unit for controlling the implantable control unit from outside the patient's body e.g. by means of an implantable switch operable by the patient.

According to one embodiment the device comprises a wireless remote control for controlling and/or programming the implantable control unit from outside the patient's body. The control unit could comprise a force controller, and the mechanical operation device could be controlled by the force controller.

According to one embodiment the implantable control unit comprises a pressure controller, and the hydraulic operation device is controlled by the pressure controller.

Stretching Device

The stretching device of the device according to any of the embodiments could comprise a first and a second engaging part, the first part could be adapted to be engaged to a first area of the stomach wall, and the second part could be adapted to be engaged to a second area of the stomach wall. The stretching device is thereby adapted to stretch a portion of the stomach wall between the first area and the second area. The stretching device could comprise a motor, such as an implantable electrical motor, which in turn could operate at least one joint to move the joint to stretch the stomach wall portion.

According to another embodiment the device could comprise a chamber having a variable volume; the chamber could be adapted to receive a fluid. The device could further comprise a reservoir adapted to hold a fluid and to be in fluid connection with the chamber. The stretching device could further comprise a pumping device, which could be adapted to move the fluid from the reservoir to the chamber, and thereby stretching the portion of the stomach wall. According to another embodiment the device further comprises a second fluid connection adapted to enable the fluid to flow back from the chamber to the reservoir during a predetermined time period.

Hydraulic

According to one embodiment the stretching device comprises a chamber adapted to have a variable volume. The chamber could comprise at least one moveable wall portion, which could be an elastic wall portion. The chamber could have an essentially round shape and could be adapted to receive a fluid.

According to another embodiment the stretching device further comprises a reservoir adapted to hold a fluid and to be in fluid connection with the chamber, the stretching device could further comprise a pumping device, which could be adapted to move the fluid from the reservoir to the chamber via a first fluid connection interconnecting the reservoir and chamber, thereby stretching the portion of the stomach wall. It is also conceivable that the stretching device further comprises a second fluid connection interconnecting the chamber and reservoir and adapted to enable the fluid to flow back from the chamber to the reservoir during a predetermined time period.

The reservoir according to any of the embodiment could be adapted to be placed subcutaneously or in the abdomen and the reservoir could be controlled by moving a wall of the reservoir which could be done using a motor adapted therefore. The chamber could also comprise an electrical motor adapted to expand the volume of the chamber.

The device could further comprise a reverse servo, wherein a small volume in the reservoir is compressed with a higher force and the chamber creates a movement of a larger total area with less force per area unit.

Sensor

The sensor implanted in the patient according to any of the embodiments could be a functional parameter sensor sensing a functional parameter of the device, such as the transfer of energy for charging an internal energy source. In other embodiments the sensor is a physical parameter sensor sensing a physical parameter of the patient, such as the food intake of the patient. The sensor according to any of the embodiments could be at least one of body temperature sensors, pressure sensors, blood pressure sensors, blood flow sensors, heartbeat sensors, breathing sensors, electrical conductivity sensors, pH sensor, light sensitive sensors, gas detection sensors and sensors sensing mechanical strain, such as a sensor adapted to sense any of contraction and relaxation of the Cardia.

According to one embodiment the device further comprises a feedback device for sending information from inside the patient's body to the outside thereof to give feedback information related to the functional parameter.

Control Unit

According to one embodiment the device is controlled by a control unit adapted to control the stretching device. The control unit could be adapted to control the stretching device, or two or more stretching devices, in response to signals from the sensor.

According to one embodiment the control unit controls the stretching devices from time to time such that one of the stretching devices at a first time stretches a first portion of the stomach wall and another of the stretching devices at a second time stretches a second portion of the stomach wall. The control unit could be adapted to be controllable from outside of the patient's body, e.g. through a wireless remote control, which in turn could comprises at least one external signal transmitter, which could be adapted to transmit a wireless control signal comprising a frequency, amplitude, or phase modulated signal or a combination thereof. According to one embodiment the at least one transmitter is adapted to transmit a wireless control signal comprising a analogue or a digital signal, or a combination of an analogue and digital control signal, or a wireless control signal comprising an electric or magnetic field, or a combined electric and magnetic field.

The control unit according to any of the embodiments could be adapted to be implanted subcutaneously in the human patient, and could be adapted to control a hydraulic system.

The device could further comprise a transferring member for powering the control unit, the transferring member could comprise a fluid transferring member and/or an electrical lead.

According to another embodiment the device further comprises an external data communicator and an implantable internal data communicator communicating with the external data communicator. The internal communicator could be adapted to feed data related to the device for treating obesity or the patient back to the external data communicator or the external data communicator feeds data to the internal data communicator.

Energizing

For energizing the device the device could further comprise a wireless energy transmitter transmitting energy by at least one wireless energy signal, such as a wave signal, e.g. a sound wave signals, ultrasound wave signals, electromagnetic wave signals, infrared light signals, visible light signals, ultra violet light signals, laser light signals, micro wave signals, radio wave signals, x-ray radiation signals and a gamma radiation signals. The wireless energy signal could further comprise an electric or magnetic field, or a combined electric and magnetic field.

According to yet another embodiment the device comprises an energy source adapted to power the device, which could comprise an internal energy source which in turn could be adapted to receive energy from an external energy source transmitting energy in a wireless mode. The internal energy source could further comprise an accumulator, at least one voltage level guard and/or at least one constant current guard.

The device could further comprise an energy-transforming device adapted to transform energy from a first form into a second form.

Fixation

The device according to any of the embodiments could comprise a fixating member, which could be adapted to fixate the stretching device to the stomach wall of the patient. The fixating member could be adapted to be in contact with sutures or staplers for fixating the stretching device to the stomach wall of the patient. The fixating member could comprise a net like structure, which could be adapted to promote growth in of human tissue for long term fixation to the stomach wall.

System

The present invention also provides an obesity treatment system comprising a device for treating obesity as described above. The system may comprise a subcutaneous electric switch adapted to manually and non-invasively control a function of the device for treating obesity.

The system may comprise a hydraulic device having a hydraulic reservoir, wherein the device for treating obesity is adapted to non-invasively be regulated by manually pressing the hydraulic reservoir.

The system may comprise a wireless remote control for controlling a function of the device. The wireless remote control comprises at least one external signal transmitter and an internal signal receiver may be provided to be implanted in the patient. The wireless remote control is adapted to transmit at least one wireless control signal for controlling the device. The wireless control signal may comprise a frequency, amplitude, or phase modulated signal or a combination thereof, and an analogue or a digital signal, or a combination of an analogue and digital signal. Alternatively, the wireless control signal comprises an electric or magnetic field, or a combined electric and magnetic field. The remote control may transmit a carrier signal for carrying the wireless control signal. The carrier signal may comprise digital, analogue or a combination of digital and analog signals. The remote control may transmit an electromagnetic carrier wave signal for carrying the digital or analog control signal.

The system may comprise a wireless energy transmitter for non-invasively energizing the device with wireless energy. The energy transmitter transmits energy by at least one wireless energy signal. The wireless energy signal may comprise a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal comprises an electric or magnetic field, or a combined electric and magnetic field. The wireless energy transmitter may transmit a carrier signal for carrying the wireless energy signal. The carrier signal may comprise digital, analogue or a combination of digital and analog signals.

The system may comprise an energy-transforming device for transforming the wireless energy from a first form into a second form energy. The energy-transforming device may directly during energy transfer operate the device with the second form energy. The second form energy may comprise a direct current or pulsating direct current, or a combination of a direct current and pulsating direct current. The second form energy may comprise an alternating current or a combination of a direct and alternating current. An accumulator may be provided, wherein the second form energy is used at least partly to charge the accumulator. The energy of the first or second form may comprise magnetic energy, kinetic energy, sound energy, chemical energy, radiant energy, electromagnetic energy, photo energy, nuclear energy or thermal energy. One of the energy of the first form and the energy of the second form may be non-magnetic, non-kinetic, non-chemical, non-sonic, non-nuclear or non-thermal.

The system may comprise an energy source adapted to power the device. The energy source may comprise an internal energy source adapted to receive energy from an external energy source transmitting energy in a wireless mode. The internal energy source is charged by the energy in the wireless mode.

The system may comprise a feedback device for sending information from inside the patient's body to the outside thereof to give feedback information related to a functional parameter.

The system may comprise a sensor sensing a parameter, such as a functional parameter of the system, which is correlated to the transfer of energy for charging an internal energy source. An internal control unit may be provided for controlling the operation device of the device in response to the sensor sensing a functional parameter. Alternatively, sensor senses a physical parameter of the patient. The physical parameter may be one of body temperature, blood pressure, blood flow, heartbeats and breathing. The physical parameter sensor may be a pressure or motility sensor, or a sensor sensing measure, bending, stretching or food intake. The internal control unit may control the operation device in response to the sensor sensing the physical parameter. An internal control unit may be provided for receiving information from the sensor.

The operation device of the device may comprise a motor or a pump. Specifically, the operation device may comprise an electric motor. The operation device may be electrically powered, may be a hydraulic operation device or may be a pneumatic operation device. The transmitted energy, directly in its wireless form may affect the operation device to create kinetic energy to operate the stretching device of the device during energy transfer.

The system may comprise a feedback device for sending information from inside the patient's body to the outside thereof to give feedback information related to a functional parameter.

The system may comprise an external data communicator and an implantable internal data communicator communicating with the external data communicator, wherein the internal communicator is adapted to feed data related to the device for treating obesity or the patient back to the external data communicator or the external data communicator feeds data to the internal data communicator.

The system may comprise implantable electrical components including at least one voltage level guard and/or at least one constant current guard.

Methods

The present invention also provides methods as listed below:

a) A method for surgically treating an obese patient, the method comprising the steps of:
cutting an opening in the abdominal wall of the patient,
dissecting an area around the stomach,
placing a device for treating obesity as described above, engaging the stomach wall of the patient, and suturing the stomach wall.

The method may further comprise the additional step of: postoperatively regulating the stretching device to stretch a part of the stomach wall to affect the appetite of the patient, wherein the step of regulating the stretching device is controlled from outside the patient's body.

The method may further comprise the additional steps of: placing an additional device for treating obesity as described above, engaging the stomach wall of the patient, stretching a first part of the stomach wall by means of the device for treating obesity, and stretching a second part of the stomach wall by means of the additional device for treating obesity.

b) A method for surgically placing a device for treating obesity in a patient via a laparoscopic abdominal approach, the method comprising the steps of:
inserting a needle or a tube like instrument into the abdomen of the patient's body, using the needle or a tube like instrument to fill the patient's abdomen with gas thereby expanding the patient's abdominal cavity,
placing at least two laparoscopic trocars in the patient's body,
inserting a camera through one of the laparoscopic trocars into the patient's abdomen,
inserting at least one dissecting tool through one of the at least two laparoscopic trocars and dissecting an intended placement area of the patient, and
placing a device for treating obesity as described above, engaging the stomach wall.

c) A method of using the system for treating obesity as described above, comprising the step of regulating the stretching device postoperatively to stretch a portion of the stomach wall to affect the appetite of the patient, wherein the step of regulating the stretching device is performed non-invasively. The stretching device comprises a mechanical or hydraulic stretching device. The hydraulic stretching device may comprise a reservoir, for moving gel or gas or fluid to or from the stretching device. The reservoir may be placed subcutaneously for being reached by the patients hand for moving fluid manually to or from the stretching device. The stretching device may be powered by an internal energy source for stretching or releasing the stretching device, wherein by means of a control device controlling the power from an internal control unit or from the outside the patient's body. A wireless energy transmitter for wireless transfer of energy powers the operation device to get the stretching device to directly during energy transfer cause the stretching device to stretch the stomach wall. A wireless energy transmitter for wireless transfer of energy charges the internal energy source. A reversed servo may be provided, wherein moving, in a closed hydraulic system, a small amount of fluid, a larger movement of fluid is achieved in a second larger closed hydraulic system, wherein the small amount of fluid is moved with by a higher force per area unit than the large volume. An invaginated stretching device in the fundus stomach wall of the patient is adapted to be adjustable, wherein the stretching device placed invaginated in the stomach fundus wall is adapted to be adjusted and stretching the stomach fundus wall thereby creating satiety.

The method may further comprise sending feedback information from inside the body to the outside thereof to give feedback related to the functional parameters of the device. Alternatively, the method may further comprise sending feedback information from inside the body to the outside thereof to give feedback related to the physical parameters of the patient. The functional parameter of the device may be correlated to the transfer of energy for charging the internal energy source. The device is programmable from outside the patient's body.

The method may further comprise the steps of:
sensing a physical parameter of the patient or a functional parameter of the device, and
sending sensing information to a control unit adapted for regulating the stretching device.

The method may further comprise the steps of:
sensing a physical parameter of the patient or a functional parameter of the device, and
sending sensing information to a control unit adapted for regulating the charging of the internal energy source.

The method may further comprise subcutaneously placing a reversed servo having a small control reservoir and moving a small volume from the control reservoir with a higher force per area unit, creating a larger movement of the stretching device with less force per area unit.

The method may further comprise performing the non-invasive regulation by manually pressing a subcutaneous switch.

The method may further comprise performing the non-invasive regulation by a wireless remote control.

The method may further comprise performing the non-invasive regulation by a wireless energy transmitter.

The method may further comprise powering the device for treating obesity by an internal energy source.

The method may further comprise powering the device for treating obesity by an external energy source transmitting wireless energy, wherein the energy source comprises an external energy source transmitting wireless energy.

The method may further comprise transmitting wireless energy from an external energy source to charge a rechargeable internal energy source.

d) A method of using a device as described above, wherein the stretching device comprises a main body including a large chamber in contact with one or more smaller reservoirs chambers adapted to stretch the stomach wall, wherein the chambers are adapted to communicate with fluid or air being moved between the chambers.

e) A method of using a device as described above, wherein the large chamber are adapted to, with its main volume to be the stretching device's most important volume and wherein, the small chambers are as the stretching devices stretching the stomach wall to treat obesity, wherein the main chamber is communicating with fluid or gel to the small chambers causing the stretching effect in the stomach fundus wall thereby treating obesity.

f) A method of using a device as described above, comprising treating reflux disease by invaginating the large chamber with its main volume in the fundus stomach wall thereby restricting movement of the stomach notch towards the diaphragm muscle of the patient, and stretching the stomach fundus wall using the small chambers, communicating with fluid or air from the large chamber to the small chambers causing a stretching effect in the stomach fundus wall thereby treating obesity.

A stretching device, adapted to post-operatively be adjustable and comprising at least one expandable section, wherein the stretching device is adapted to be adjustable between a first collapsed state and a second expanded state. In the first collapsed state the expandable section is collapsed, and in the second expanded state, the expandable section is expanded. The outer surface of said expandable section does at least partly comprise a surface structure having elevated areas alternating with lowered areas. The expandable section is adapted to have, in at least one of said first collapsed and second expanded states a first distance between adjacent elevated areas sufficiently extended to prevent growth of fibrotic tissue from directly interconnecting adjacent elevated areas to an extent that compromises the adjustability between a first collapsed and a second expanded state of said stretching device. The expandable section further comprising connecting areas between adjacent elevated and lowered areas, further adapted to have, in at least one of said first collapsed and second expanded states, a second distance between adjacent connecting areas sufficiently extended to prevent growth of fibrotic tissue from directly interconnecting adjacent connecting areas to an extent that compromises the adjustability between a first collapsed and a second expanded state of said stretching device.

According to one embodiment the expandable section is hollow or comprises a hollow body.

According to another embodiment the stretching device is substantially completely hollow or comprises a hollow body extending along substantially the complete length and/or complete volume of said stretching device.

Fibrotic tissue can often have an extension or thickness of about 0.5 mm to about 1.5 mm and hence the distances between relevant surfaces of the elements of the surface structure are suitably greater than about 3 mm, hence greater than about 2×1.5 mm. But depending on the circumstances also distances greater than about 1.0 mm to about 3 mm may be sufficient. In cases where the fibrotic tissue can be expected to have an extension or thickness greater than about 1.5 mm the distances between relevant surfaces of the elements of the surface structure are adapted in a suitable manner.

The surface structure may comprise elevated and lowered areas and it may be suitable that also a distance between the different planes of the elevated and lowered areas is bigger than a certain threshold to facilitate the collapsible and/or expandable functionality of the stretching device. If said distance is too small, the collapsible and/or expandable functionality of the stretching device may be limited. A suitable interval for said distance is around 0.5 to 10 mm, more suitable around 2-8 mm and most suitable around 3-7 mm The surface structure may comprise different geometrical elements or shapes and any combination of such elements or shapes as long as the above mentioned conditions for the distances can be met. The surface structure may e.g. comprise ridges and grooves of different shapes. The ridges and grooves may each have a cross-section that is e.g. wedge-shaped, polygonal, square-formed, pyramidal-shaped, truncated pyramidal-shaped or. Further may the ridges and grooves have cross-sections of different shapes. The surface structure may as well in general comprise a bellows-shaped structure or a surface structure where geometrical objects of the same or different kind(s) are placed on a surface. The geometrical objects may be practically randomly placed on the surface or according to some scheme.

One type of stretching devices where this type of surface structure may be suitable, is stretching devices where the stretching device should have the ability to change shape and/or size substantially. Hence, this is a case where the presence of fibrotic tissue substantially could hinder or impede the function of the stretching device. But the surface structure may be used by any stretching device where the characteristics of the surface structure would be advantageous for the stretching device.

A stretching device, adapted to post-operatively be adjustable and comprising at least one expandable section, wherein the stretching device is adapted to be adjustable between a first collapsed state and a second expanded state. In the first collapsed state the expandable section is collapsed, and in the second expanded state, the expandable section is expanded. The outer surface of said expandable section does at least partly comprise a surface structure having elevated areas alternating with lowered areas. The expandable section is adapted to have, in at least one of said first collapsed and second expanded states a first distance between adjacent elevated areas sufficiently extended to prevent growth of fibrotic tissue from directly interconnecting adjacent elevated areas to an extent that compromises the adjustability between a first collapsed and a second expanded state of said stretching device. The expandable section further comprising connecting areas between adjacent elevated and lowered areas, further adapted to have, in at least one of said first collapsed and second expanded states, a second distance between adjacent connecting areas sufficiently extended to prevent growth of fibrotic tissue from directly interconnecting adjacent connecting areas to an extent that compromises the adjustability between a first collapsed and a second expanded state of said stretching device.

According to one embodiment the expandable section is hollow or comprises a hollow body.

According to another embodiment the stretching device is substantially completely hollow or comprises a hollow body extending along substantially the complete length and/or complete volume of said stretching device.

Fibrotic tissue can often have an extension or thickness of about 0.5 mm to about 1.5 mm and hence the distances between relevant surfaces of the elements of the surface structure are suitably greater than about 3 mm, hence greater than about 2×1.5 mm. But depending on the circumstances also distances greater than about 1.0 mm to about 3 mm may be sufficient. In cases where the fibrotic tissue can be expected to have an extension or thickness greater than about 1.5 mm the distances between relevant surfaces of the elements of the surface structure are adapted in a suitable manner.

The surface structure may comprise elevated and lowered areas and it may be suitable that also a distance between the different planes of the elevated and lowered areas is bigger than a certain threshold to facilitate the collapsible and/or expandable functionality of the stretching device. If said distance is too small, the collapsible and/or expandable functionality of the stretching device may be limited. A suitable interval for said distance is around 0.5 to 10 mm, more suitable around 2-8 mm and most suitable around 3-7 mm The surface structure may comprise different geometrical elements or shapes and any combination of such elements or shapes as long as the above mentioned conditions for the distances can be met. The surface structure may e.g. comprise ridges and grooves of different shapes. The ridges and grooves may each have a cross-section that is e.g. wedge-shaped, polygonal, square-formed, pyramidal-shaped, truncated pyramidal-shaped or. Further may the ridges and grooves have cross-sections of different shapes. The surface structure may as well in general comprise a bellows-shaped structure or a surface structure where geometrical objects of the same or different kind(s) are placed on a surface. The geometrical objects may be practically randomly placed on the surface or according to some scheme.

One type of stretching devices where this type of surface structure may be suitable, is stretching devices where the stretching device should have the ability to change shape and/or size substantially. Hence, this is a case where the presence of fibrotic tissue substantially could hinder or impede the function of the stretching device. But the surface structure may be used by any stretching device where the characteristics of the surface structure would be advantageous for the stretching device.

BRIEF DESCRIPTION OF THE DRAWINGS

The present invention will now be described in more detail by way of non-limiting examples and with reference to the accompanying drawings, in which:

FIG. 7 shows an embodiment wherein the stretching device is a mechanical stretching device, according to a first embodiment.

FIG. 8a-8b shows an embodiment wherein the stretching device is a mechanical stretching device, according to a second embodiment.

FIGS. 13-36c shows schematic figures describing different functions of the stretching device.

DETAILED DESCRIPTION

Figure 1:
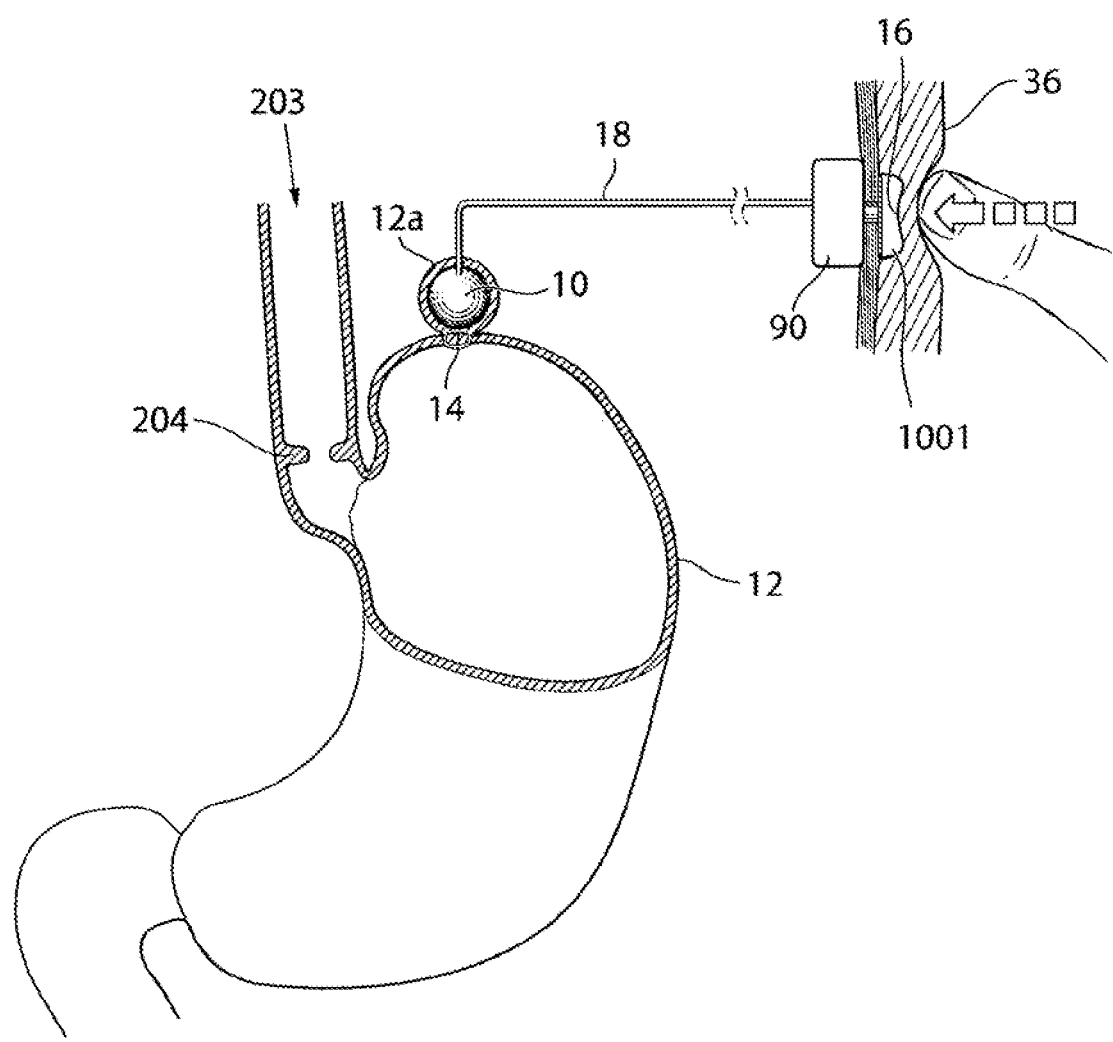
FIG. 1 shows a stretching device implanted in the stomach fundus wall of a patient, on the inside thereof.

Invaginated in the stomach wall is to be understood as an object being placed inside of a cavity made of stomach wall material. The invagination enables stomach to stomach sutures or staplers which enables the object of be enclosed by means of the human tissue healing.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

FIG. 1 shows a first embodiment of an obesity treatment device. The device comprises a stretching device 10 implanted in a human patient. In FIG. 1 the stretching device 10 is invaginated in the wall 12 of the patient's stomach 12 and the body of the stretching device 10 is shaped to rest against the wall 12 of the stomach 12 and further has an outer surface suitable to rest against this wall 12. This means that the stretching device 10 preferably has an essentially round shape to not damage the stomach wall. However, the stomach wall 12 is strong so many different shapes and forms may be used.

The stretching device 10 can be fixed to the wall 12*a* of the stomach 12 in a number of different ways. In the embodiment shown in FIG. 1, the stretching device 10 is invaginated in the stomach wall 12*a*. After in-vagination, a number of stomach-to-stomach sutures or staplers 14 are applied to keep the in-vagination in the short term. This allows growth of human tissue, keeping the in-vagination in the long term.

By enlarging the size of the stretching device, the stomach wall 12 surrounding the stretching device 10 is stretched since the circumference of the stretching device 10 is increased. By this stretching, receptors in the stomach wall indicate that the stomach is full, thereby creating a feeling of satiety to the patient. Correspondingly, when the stretching device 10 is contracted, the receptors indicate that the stomach is not full, thereby returning the feeling of hunger.

The expansion and contraction of the stretching device 10 can be performed under direct control of the patient. Alternatively, the expansion and contraction can be performed according to a pre-programmed schedule.

Returning to FIG. 1, this figure also shows a fluid operation device, i.e., a hydraulic or pneumatic operation device suited for operating the stretching device, which in the following will be described in detail.

The stretching device 10 forms a fluid chamber, in which fluid is allowed to flow. The stretching device 10 thus forms an expandable chamber that can change the volume it occupies in the stomach wall, thereby forming a hydraulically or pneumatically regulated stretching device 10.

A regulation reservoir 16 for fluids is connected to the stretching device 10 by means of a conduit 18 in the form of a tube. The stretching device 10 is thereby adapted to be regulated, preferably non-invasively, by moving liquid or air from the regulation reservoir 16 to the chamber formed by the stretching device.

The regulation reservoir 16 can be regulated in several ways. In the embodiment shown in FIG. 1, the regulation reservoir 16 is regulated by manually pressing the regulation reservoir 16. In other words, the regulation reservoir 16 is regulated by moving a wall of the reservoir. It is then preferred that the regulation reservoir 16 is placed subcutaneously and non-invasive regulation is thereby achieved.

When the regulation reservoir 16 is pressed, the volume thereof decreases and hydraulic fluid is moved from the reservoir to the chamber formed by the stretching device 10 via the conduit 18, enlarging or expanding the stretching device 10. For filling and calibrating the fluid level of the device an injection 1001 port is furthermore provided. The injection port preferably comprises self sealing membrane, such as a silicone membrane.

It will be appreciated that instead of hydraulic operation, pneumatic operation can be used, wherein air instead of hydraulic fluid is moved between the reservoir 16 and the chamber formed by the stretching device 10. Preferable the reservoir has a locking position to keep it in the desired position. If the patient compresses the reservoir 16 it preferably stays compressed and releases after pressing again.

Any kind of hydraulic solution may be used for the stretching device. The hydraulic solution may be driven by both mechanically and be powered with any motor or pump as well as manually.

FIG. 1 further shows a reversed servo system which comprises a regulation reservoir 16 and a servo reservoir 90. The servo reservoir 90 hydraulically controls a stretching device 10 via a conduit 18. The reverse servo function is described in greater detail in FIGS. 33-36

Figure 2A:
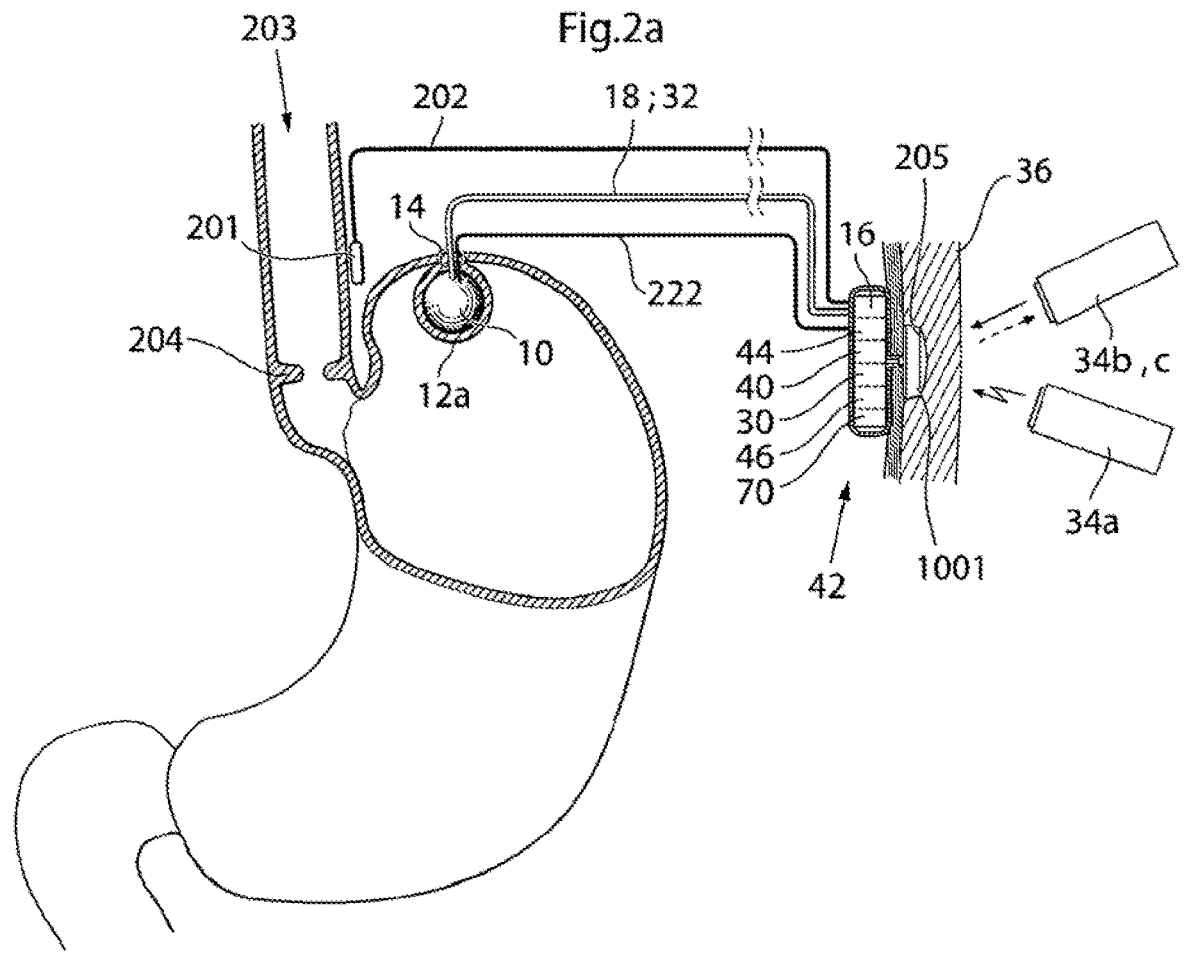
FIG. 2a shows a stretching device implanted in the stomach fundus wall of a patient, on the outside thereof.

FIG. 2*a* shows the device according to another embodiment in which a motor 40 is adapted to move a wall of the regulation reservoir 16. The powered regulation reservoir 16 is then preferably placed in the abdomen of the patient. In this embodiment, a wireless external remote control unit 34*b,c* and an external energy transmission device 34*a* can be provided to perform non-invasive regulation of the motor via an energy transforming device 30, which is adapted to supply an energy consuming operation device, in the present example the motor 40, with energy.

The remote control may comprise a wireless energy transmitter, 34*a* which also can act as a regulation device for non-invasively regulating the stretching device. When the regulation is performed by means of a remote control 34 an internal power source 70 for powering the regulating device is provided. The internal energy source 70 can for example be a chargeable implanted battery or a capacitor or a device for receiving wireless energy transmitted from outside the body of the patient. Different ways of regulating the stretching device 10 will be described below with reference to FIGS. 13-29.

The device as shown in FIG. 2*a* further comprises a sensor 201 sensing a parameter of the patient or the device preferably connected to the food intake of the patient. The sensor is connected to a control assembly 42 by means of a sensor signal transferring member 202. The sensor can be used to regulate said device in a completely automatic way, i.e. the device responds to a sensor signal connected to the food intake of the patient, thereby affecting the control assembly to operate the stretching device 10 to stretch the stomach wall 12 and thereby creating a feeling of satiety in the patient. The sensor could be adapted to measure the food intake of the patient through any of temperature, blood pressure, blood flow, heartbeats, breathing and pressure and can be placed in the stomach 12, esophagus 203 or in connection with the cardia 204. According to one embodiment said sensor is a strain gauge measuring contraction and/or relaxation of the cardia 204.

The device as shown in FIG. 2*a* further comprises a second conduit 222 for backflow of hydraulic fluid. The backflow is adapted to create the desired feeling of satiety for a predetermined time whereafter the hydraulic fluid has flowed back in a quantity large enough for the stretching device not to stretch the stomach wall anymore and thereby the feeling of hunger returns to the patient. A suitable time for the process is between 1 and 6 hours. According to other embodiments the backflow takes place in the main conduit 18 by means of a valve system connected to said conduit 18.

For filling and calibrating the fluid level of the device an injection 1001 port is furthermore provided. The injection port 1001 preferably comprises self sealing membrane, such as a silicone membrane.

Figure 2B:
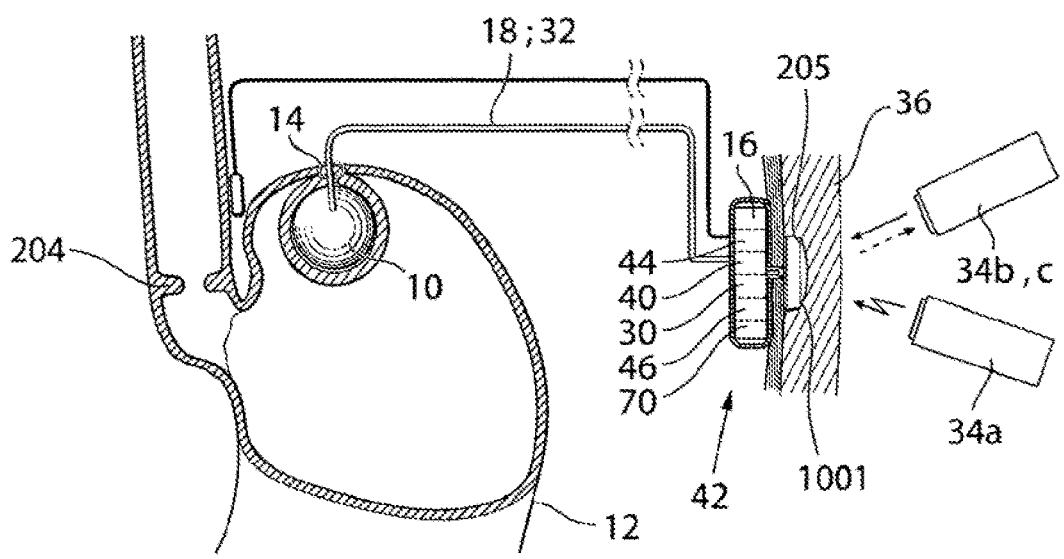
FIG. 2b shows a stretching device implanted in the stomach fundus wall of a patient, on the outside thereof in a second state.

FIG. 2b shows the device according to the embodiment of FIG. 2a, in a second state in which the stretching device 10 is expanded and thereby stretches the stomach wall 12.

Figure 3A:
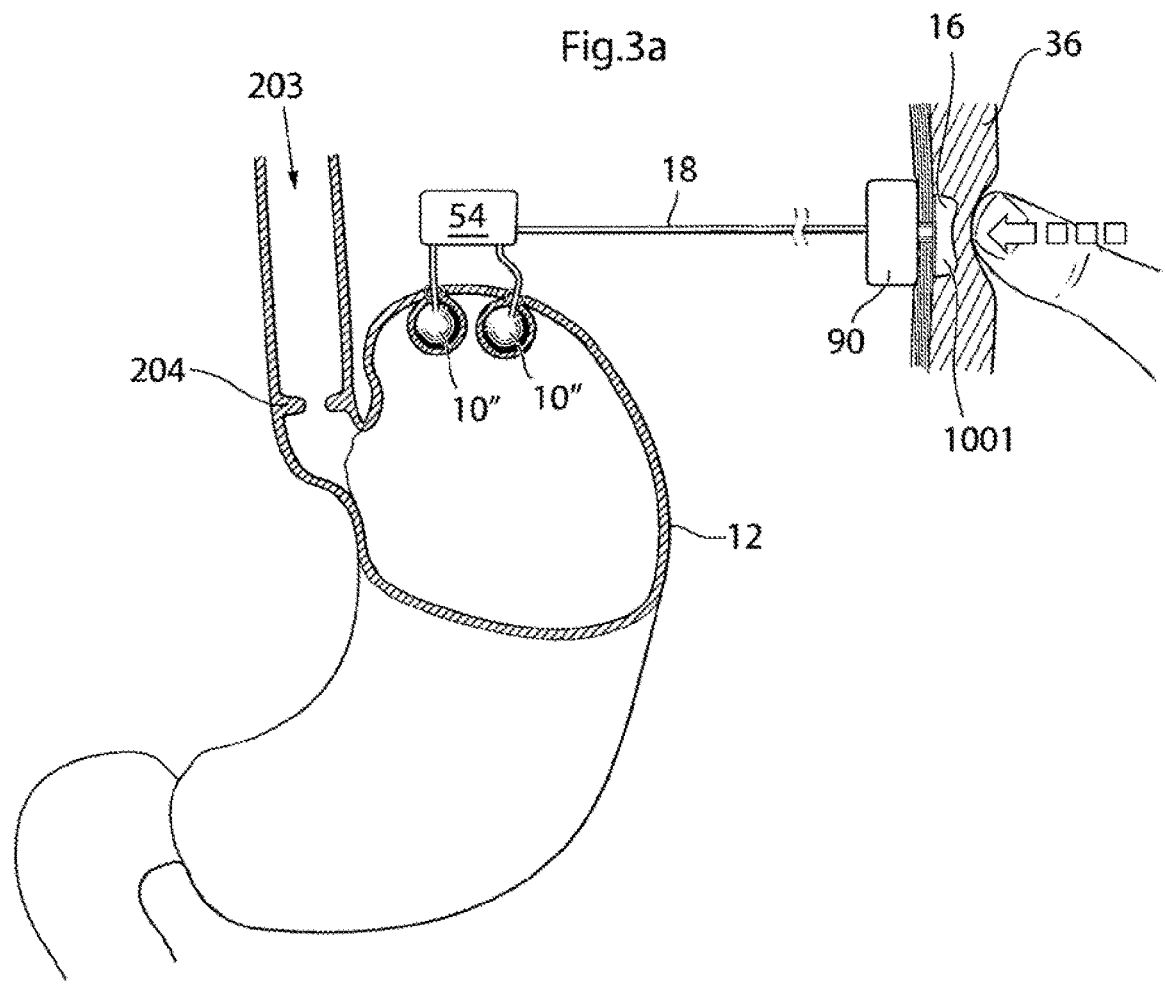
FIG. 3a shows an embodiment where the stretching device comprises two stretching devices, according to a first embodiment.

FIG. 3a shows an embodiment, wherein two stretching devices 10″ are provided. Both stretching devices 10″ work according to the principles described above with reference to FIG. 1. They can be adapted to postoperatively and non-invasively be regulated and adapted to from time to time regulate different stretching devices to at a first time stretch a first part of the stomach wall and at a second time stretch a second part of the stomach wall.

Such a stretching device 10 may be used for keeping electronics and/or an energy source and/or hydraulic fluid. Hydraulic fluid from that device may be distributed to several smaller stretching device areas to vary the stretching area from time to time avoiding any possible more permanent stretching effect of the stomach wall. Even mechanically several stretching areas may be used. The embodiment according to FIG. 3a further comprises a hydraulic valve shifting device 54, implanted in the patient, for shifting between operating the first and the second stretching device 10″. The alternating creates a more sustainable device since the receptors in the stomach wall is stimulated gets a longer time of recovery between the stretches.

Figure 3B:
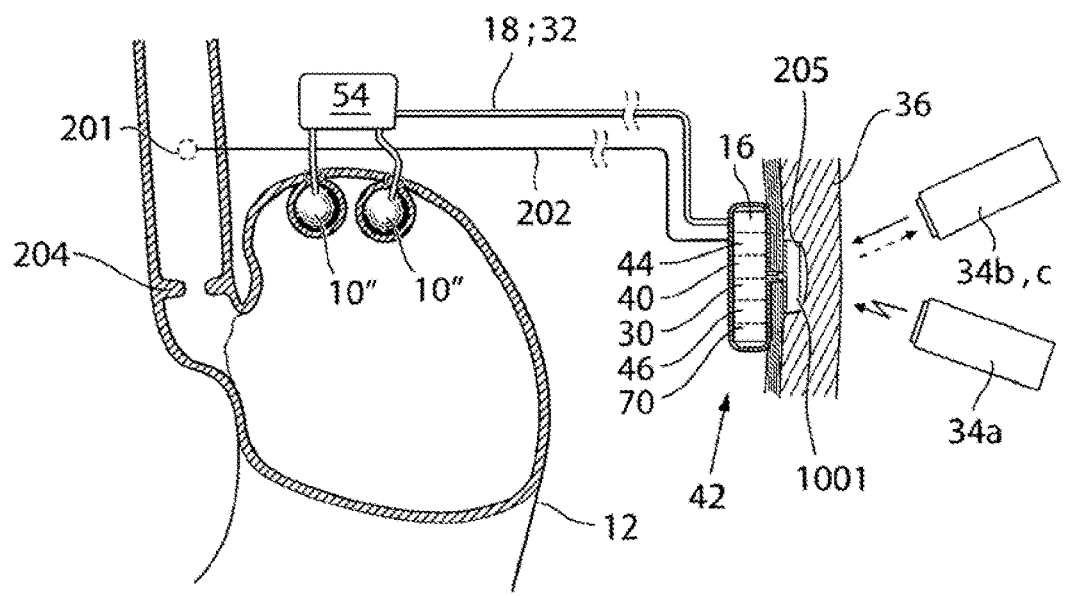
FIG. 3b shows an embodiment where the stretching device comprises two stretching devices, according to second embodiment.

In FIG. 3a the system is a manual system controlled by the patient as described before with reference to FIG. 1, whereas in FIG. 3b the system is energized using wireless energy as described before with reference to FIG. 2a.

Figure 4A:
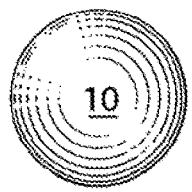
FIGS. 4a-i shows the stretching device according to different embodiments.
Figure 4E:
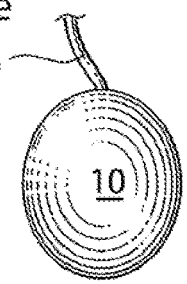
Figure 4B:
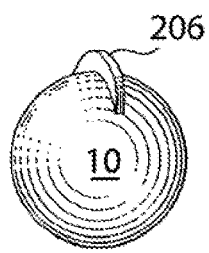
Figures 4F, 4G:
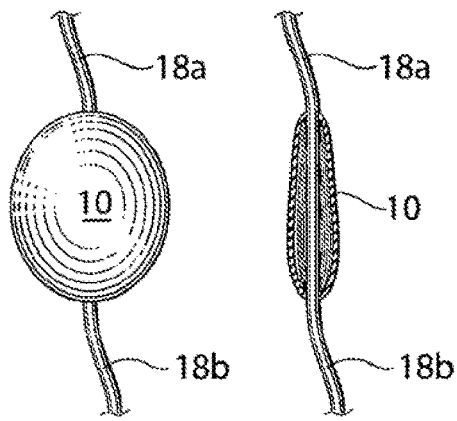
Figure 4C:
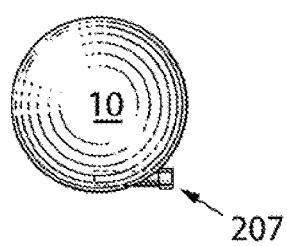
Figure 4H:
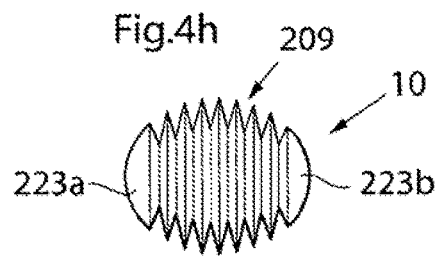
Figure 4D:
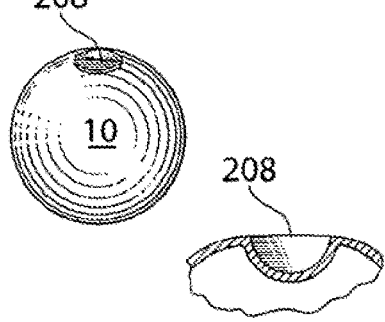
Figure 4I:
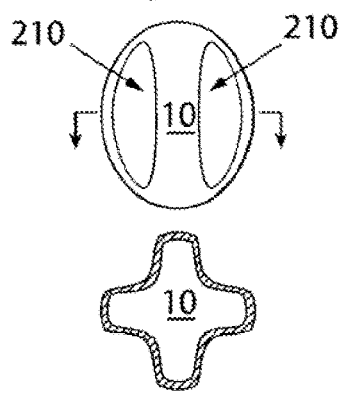

FIG. 4a-e shows different embodiments of the stretching device 10 adapted to be implanted in a patient. The stretching device 10 comprises a surface adapted to be in contact with the stomach wall 12 when the device is invaginated in the stomach wall. FIG. 4b shows an embodiment of the stretching device in which the stretching device comprises a fixating member 206 for suturing or stapling the stretching device to the stomach wall. The fixating member 206 could comprise holes for receiving said sutures or staplers 14, or the fixation device 206 could be penetrable such that the sutures or staplers can penetrate the stomach wall and the fixation device 206. 4c shows the stretching device 10 according to an embodiment in which the stretching device 10 comprises an inlet member 207 for filling said device with a fluid. Said inlet member is preferably connected to a hydraulic conduit 18 adapted to be invaginated in the stomach wall 12. FIG. 4d shows the stretching device 10 according to an embodiment in which the stretching device 10 comprises a holding member 208 adapted to connect to an insertion device when said stretching device 10 is inserted into an invaginated pouch of the stomach wall 12. FIG. 4e shows the stretching device 10 according to an embodiment in which the stretching device has a slightly oval or egg-shaped shape. FIG. 4e furthermore shows the hydraulic conduit 18 attached to said stretching device 10. FIG. 4f shows the stretching device 10 according to an embodiment in which the stretching device is inflatable by a fluid transported through the conduit 18. According to one embodiment shown in FIG. 4f the conduit comprises two sections 18a,b wherein the first section 18a is used to pull the stretching device 10 into place, and to fill the device 10 with a suitable fluid, whereas the second section 18b is used for the operation of said device 10. FIG. 4g shows the stretching device 10 according to the embodiment of FIG. 4f in a deflated state. The stretching device 10 is inserted through a hole in the stomach wall 12 in its deflated state whereafter the device 10 is filled with a suitable fluid for operation. FIG. 4h shows the stretching device 10 according to an embodiment in which the stretching device 10 comprises two movable wall portion 223a,b, which are moveable by means of a bellows structure 209 made of a flexible material. FIG. 4i shows the stretching device according to an embodiment where the stretching device is expandable by means of four expandable sections 210 symmetrically placed on four places along the surface of the stretching device, as shown in the section image of FIG. 4i. The expandable sections 210 are made of a flexible material for allowing said sections 210 to expand when said stretching device 10 is filled with a hydraulic fluid.

Figure 5:
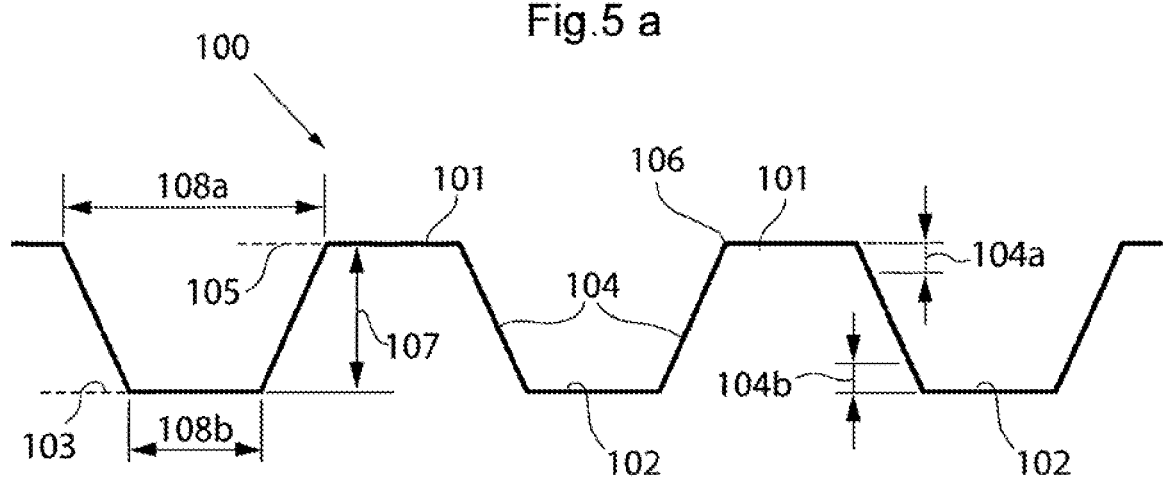
FIG. 5a is a sectional view of a surface structure 700 of the stretching device 10.
FIG. 5b is a sectional view similar to that of FIG. 5a but with a slightly different surface structure 700.
FIGS. 5c-e are drawings showing sections of examples of the surface structure 700 described herein, FIG. 5f schematically shows an embodiment of a stretching device 10 having a surface structure 700.
FIGS. 5g and 5h show examples of different cross sections for a prosthesis.
FIGS. 5i-5k are drawings showing examples of different surface structures.
Figure 5:
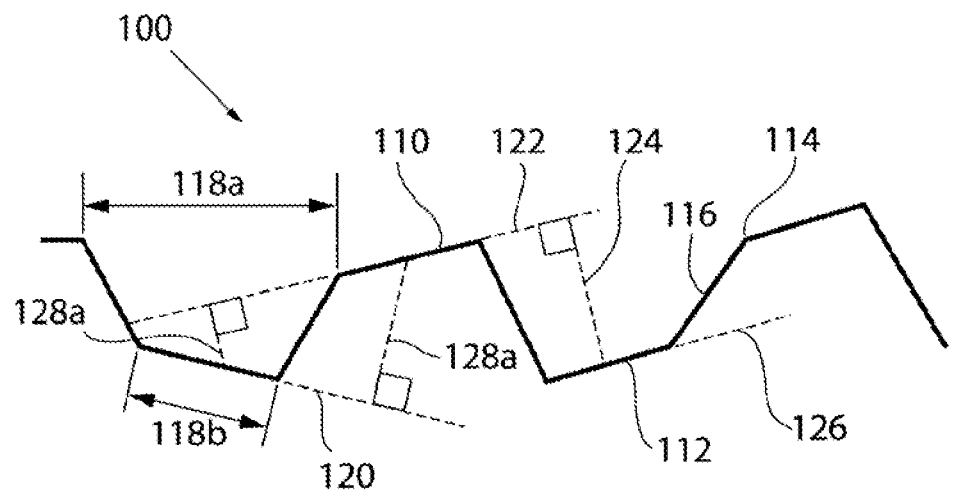
Figure 5C:
Figure 5D:
Figure 5E:

A first distance 708a between two elevated areas 701, see FIG. 5a, is long enough so as to prevent growth of fibrotic tissue directly connecting two adjacent elevated areas 707. That is, it may be possible that fibrotic tissue grows on the surface of the elevated and lowered areas 701, 702 and the connecting areas 704. However, thanks to the extension of the first distance 708a, fibrotic tissue is prevented from growing directly from one elevated area 701 to another adjacent elevated area 701.

With the expression "growing directly from one elevated area 701 to another elevated area 701" it is e.g. meant that fibrotic tissue grows from one elevated area 701 to another while not or only to a small extent growing on a connecting area 704. As indicated at 704a in FIG. 5i, the first distance 708a may be measured within an interval 704a from the level of an elevated area 701. The expression "growing directly from one elevated area 701 to another elevated area 701" also includes the situation that fibrotic tissue grows on adjacent areas, e.g. two adjacent connecting areas 704, with such a thickness that the fibrotic tissue from each adjacent area meet and bridge the distance or space between two elevated areas 701. In such a situation the space between two elevated areas 701 may be partly or completely filled with fibrotic tissue.

It may be advantageous that also a second distance 708b corresponding to the extension of a lowered area 702 has an extension great enough so as to prevent fibrotic tissue from growing directly from one connecting area 704 to another connecting area 704. With the expression "growing directly from one connecting area 704 to another connecting area 704" it is meant that fibrotic tissue grows from one connecting area 704 to another while not or only to a small extent growing on a lowered area 702.

In FIG. 5a surface structure comprising elevated and lowered areas has been shown, but apart from elevated and lowered areas also many other geometrical structures may be used where it is possible to fulfill the above mentioned prevention of growth of fibrotic tissue. In particular, the above mentioned prevention of growth of fibrotic tissue between elevated areas and between connecting areas.

Figure 5F:
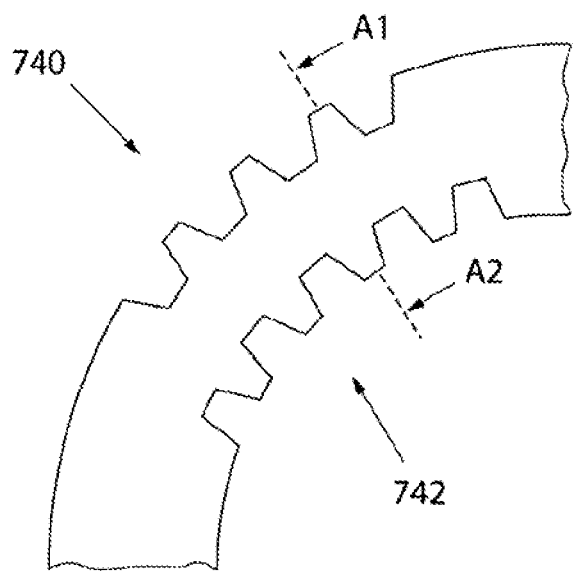
Figure 5G:
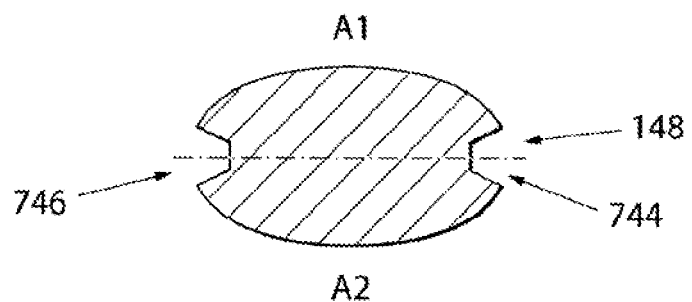
Figure 5H:
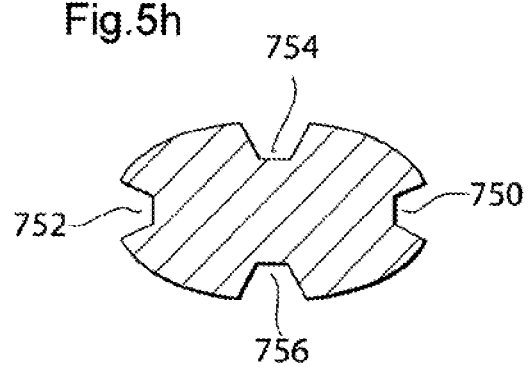
Figure 5I:
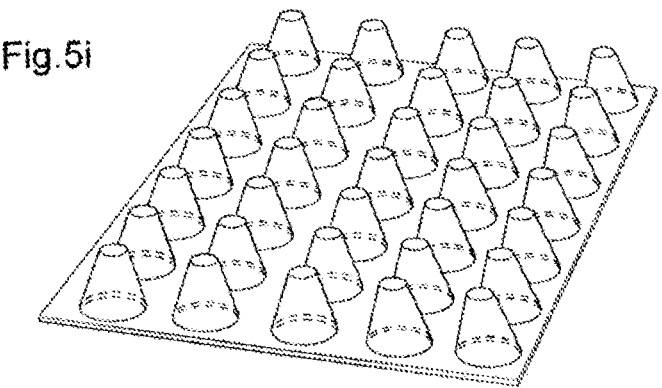
Figure 5J:
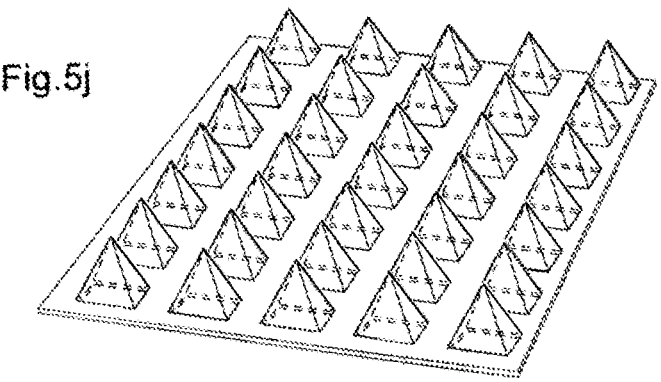
Figure 5K:
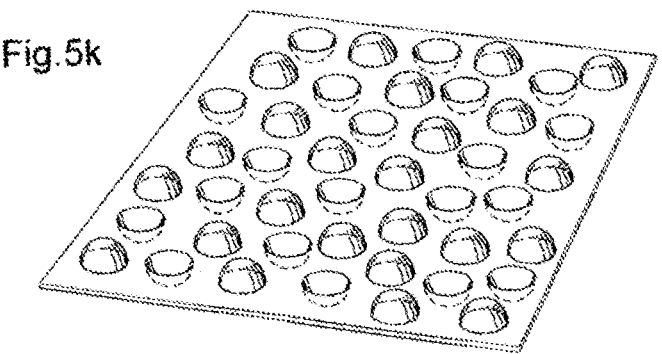

Some examples of such other geometrical structures are shown in FIGS. 5i-5k. In a surface structure comprising ridges and grooves, the ridges and grooves may also have different sections, some examples are shown in FIGS. 5a-5e.

Referring mainly to FIGS. 5a and 5b some expressions and aspects will now be explained. In this application the concept of a first distance 708a, 718a between adjacent elevated areas 701, 710 is used. With such a first distance 708a, 718a it is meant a distance that is measured substantially from the edge 706, 714 of one elevated area 701, 710 to the edge 706, 714 of an adjacent elevated area 701, 710. Measured substantially from the edge means that the measurement may be done within a first interval 704a from the level of an elevated area 701, 710, the first interval 704a extending from the level of an elevated area 701, 710 towards the level of an adjacent lowered area 702, 712.

In this application also the concept of a second distance 708b. 718b between adjacent connecting areas 704, 716 is used. With such a second distance 708b, 718b it is meant a distance that is measured substantially from the connection point between a connecting area 704, 716 and a lowered area 702, 712 to another connection point involving an adjacent connecting area 704, 716. Measured substantially from the connection point means that the measurement may be done within a second interval 704b from the level of a lowered area 702, 712, the second interval 704b extending from the level of a lowered area 702, towards the level of an adjacent elevated area 701, 710.

With elevated and lowered areas it is meant areas that lie in different planes 703, 705, 720, 722 where the planes are separated by a distance 707, 724, 728. The planes may be parallel or substantially parallel but may also be non-parallel. If the planes are parallel, defining a distance between them is trivial. If the planes are non-parallel (as in FIG. 5b) a distance between the planes may be defined by a normal 724, 728 to one of the planes 720, 722 where the normal extend to a point on an area in another plane 722, 726 and the distance between the planes is equal to the extension of the normal 724, 728. As seen in FIG. 5b the normal 724, 728 extends from a plane 720, 722 to a point which is approximately equally distant from the edges of an area. There are two possible ways to define the normal or distance between the planes. Taking normal 728 as example, one may define the normal as in 728a or in 728b. It may be suitable to define the distance between two planes as the extension of the longest normal, the distance between the planes 720 and 722 would then be equal to the extension of normal 728a. This definition will be used hereafter.

The elevated and lowered areas may have different shapes, they may be plane or substantially plane but they may also have some kind of curved shape.

The elevated areas 701, 710 connect to adjacent lowered areas 702, 712 by means of connecting areas 704, 716. The connection between elevated/lowered areas and connecting areas 704, 716 may comprise a radius of different sizes, bigger or smaller radii. When the radius is very small there will substantially be an edge 706, 714 connecting the areas.

The expression "expandable section" implies that said section also is collapsible.

Suitably the stretching device 10 at least partly comprises materials which have a high degree of biocompatibility, such materials may be called physiologically inert, biologically inert or biocompatible.

Referring in particular to FIGS. 5a and 5b, in the surface structure 700 there may advantageously be a specified first distance 708a, 718a between adjacent elevated areas 701, 710. The distance between adjacent elevated areas 701, 710 is chosen so that fibrotic tissue cannot bridge the first distance 708a, 718a between adjacent elevated areas 701, 710. Hence, the first distance 708a, 718a between adjacent elevated areas 701, 710 is advantageously big enough to prevent the formation of fibrotic tissue that bridges adjacent elevated areas 701, 710.

As mentioned before, there may advantageously be a specified second distance 708b, 718b between adjacent connecting areas 704, 716. The second distance 708b, 718b between adjacent connecting areas 704, 716 is chosen so that fibrotic tissue can not bridge the second distance 708b, 718b between adjacent connecting areas 704, 716. Hence, the second distance 708b, 718b between adjacent connecting areas 704, 716 is advantageously big enough to prevent the formation of fibrotic tissue that bridges adjacent connecting areas 704, 716.

It may also be advantageous that a third distance 707, 724, 728a between the different planes 703, 705, 720, 722, 726 of the elevated and lowered areas is bigger than a certain threshold to facilitate the collapsible and/or expandable functionality of the stretching device. If the third distance 707, 724, 728a is too small the collapsible and/or expandable functionality of the stretching device may be limited. A suitable interval for the third distance 707, 724, 728a is 0.5 to 10 mm, more suitable 2-8 mm and most suitable 3-7 mm. Also regarding the aspect that the fibrotic tissue should not impede the collapsible/expandable functionality of the stretching device it is advantageous that the distance 707, 724, 728a is not too small, but suitably in the interval/s as mentioned previously.

The surface structure 700 may include objects or elements of different geometrical shapes, for example ridges of different shapes, embossments of different shapes and other objects which enable a surface structure as described herein. The area of the elevated areas 701, 710 may be very small while still resulting in a surface structure that has the desired functionality. The area of the elevated areas 701, 710 may even be almost zero, as exemplified in FIG. 5e. Whereas FIGS. 5a and 5b-5e show cross sections of examples of surface structures 700, FIGS. 5i-5k show examples of different surface structures 700 in perspective. The objects or elements in the surface structure 700 may be placed in rows, ordered in some other way, or may be more or less randomly distributed over the surface of the stretching device. Different types of objects may also be used together in the surface structure 700, e.g. a combination of pyramid shaped and cone shaped objects together with ridges of some shape.

In FIGS. 5f-5h an embodiment of a stretching device 10 is shown where a surface structure 700 is used, the stretching device 10 is not shown in full. FIG. 3 shows a longitudinal section of the stretching device 10 where 740 denotes the surface structure on the upper side of the stretching device 10 and 742 denotes the surface structure on the under side of the stretching device 10. As shown in FIG. 5f the surface structure 742 on the under side may have a greater extension than the surface structure 740 on the upper side of the penile prosthesis. This gives the stretching device 10 an up-bent position when the stretching device 10 is expanded. The surface structures 140 and 142 are one example of a bending portion. FIG. 5g shows a cross section of the stretching device 10 where the stretching device 10 includes a waist portion 744, where the waist portion comprises waist surface structures 746 and 748. The waist portion with the waist surface structures 746 and 748 make the stretching device 10 expandable also in the radial direction. The stretching device 10 may also have a cross section as shown in FIG. 10 comprising a waist portion 744 having four waist surface structures 750, 752, 754, 756 further facilitating the ability of the stretching device 10 to be expandable also in the radial direction. The cross section in FIG. 5g is taken along the line A1-A2 in FIG. 5f.

Figure 6A:
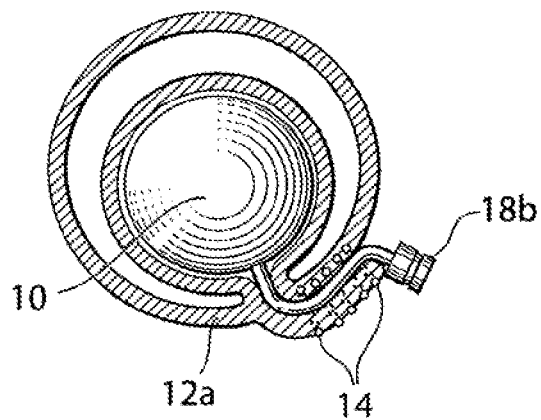
FIGS. 6a-c shows the stretching device invaginated in the stomach wall.

FIG. 6a illustrates a stretching device 10 provided with an inlet port 18b. The stretching device 10 is invaginated in the stomach wall 12 and the inlet port 18b is available for connection to a tube or the like from the abdominal area of the patient. The tube or conduit 18 can preferably be connected to the control unit 42 or an injection port 1001.

Figure 6B:
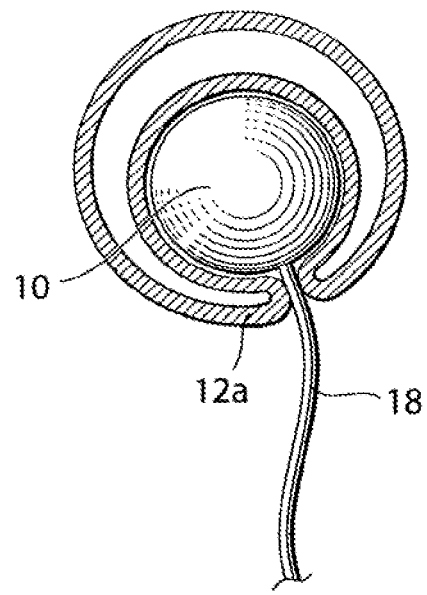

FIG. 6b illustrates an invaginated stretching device 10 wherein, instead of an inlet port, a conduit 18 or electrical lead extends into the abdominal area of the patient.

Figure 6C:
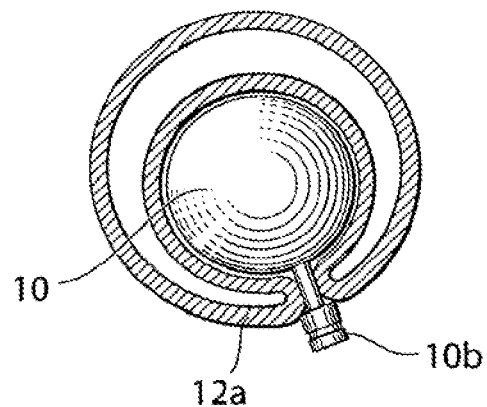

FIG. 6c shows a section of the stretching device 10 and part of the stomach in which the stretching device 10 is invaginated. The conduit 18 or electric lead is invaginated in the stomach wall 12 by means of stomach to stomach sutures or staplers 14 which creates an entirely sealed pouch of stomach wall tissue in which the stretching device 10 is placed. The conduit 18 or electric lead is thereby tunneled in the stomach wall 12 between the inlet port 18b and the volume filling device 10.

It has been shown that the shape of the stretching device 10 can take many different forms. It will be appreciated that also the material of the stretching device 10 can vary. It is preferred that the stretching device 10 is provided with a coating, such as a Parylene, polytetrafluoroethylene (PTFE), or polyurethane coating, or a combination of such coatings, i.e., a multi-layer coating. This coating or multi-layer coating improves the properties of the stretching device, such as its resistance to wear.

In another embodiment shown in FIG. 7, the stretching device 110 works according to a different principle from that described above with reference to FIGS. 1-6. The stretching device 10 here comprises a first fixation portion 110a adapted to have a first fixation at a first position on the stomach wall 12 and a second fixation portion 110b adapted to have a second fixation at a second position on the stomach wall 12. These fixation portions 110a,b, which preferably have an essentially round shape and preferably are adapted to be invaginated in the stomach wall 12, are attached to the distal end of a respective leg 211, which in turn are attached at their respective proximal end to an operation device, such as a motor 40. According to the embodiment shown in FIG. 7 the motor is a hydraulic motor, comprising a hydraulic piston, which is connected to a manual operation device described previously with reference to FIG. 1. The hydraulic piston affects the legs through their connection with a joint 212 placed in the extremity of the leg. The stretching device 10 is enclosed in a housing 214 protecting the device from the in growth of fibrotic tissue which potentially could damage the function of said device 110. However it is equally conceivable that the motor is another hydraulic motor, a pneumatic motor or an electrical motor.

The stretching device 110 is adapted to increase the distance between the first position and the second position on the stomach wall 12, thereby stretching the stomach wall 12. The first and/or second fixation portions 110a, 110b are adapted to at least partly be invaginated in the stomach wall 12 with stomach-to-stomach sutures or staplers 14 holding the fixation portions 110a,b in place in suspension in relation to the stomach wall 12.

Of course the first and second positions may be sutured or fixated to the stomach wall in many possible ways and the invention covers all possibilities to distend the stomach wall by moving two portions of the stomach wall away from each other and thereby first fixating the device to at least two positions on the stomach wall. However, the soft suspended connection to the stomach wall 12 where fibrotic stomach-to-stomach tissue helps to give a long term stable position is to prefer.

Of course just expanding an invaginated part of the stomach also stretches away the stomach wall 12, which also may be achieved both mechanically, hydraulically, pneumatically and both being powered with a motor or pump or by manual force.

Any kind of mechanical construction may be used and the mechanical embodiment disclosed is one example. Any mechanical construction driven by mechanically or hydraulically or any pneumatic construction may be used. Any motor or any pump or moving material changing form when powered may be used to achieve the simple goal of stretching a part of the stomach wall by moving at least two portions of the stomach wall away from each other.

FIG. 8 shows the stretching device 10 according to an embodiment in which the stretching device is controlled from an implantable control assembly 42 to which sensor input, as described earlier, in received. The stretching device is then regulated through the conduit 18 using a pump 44, connected to at least one fluid reservoir 16, 46, and powered from a energy transforming member 30 connected to an receiver of wireless energy 205, placed under the skin 36, or an implantable energy source 70, such as a rechargeable battery.

Figure 9A:
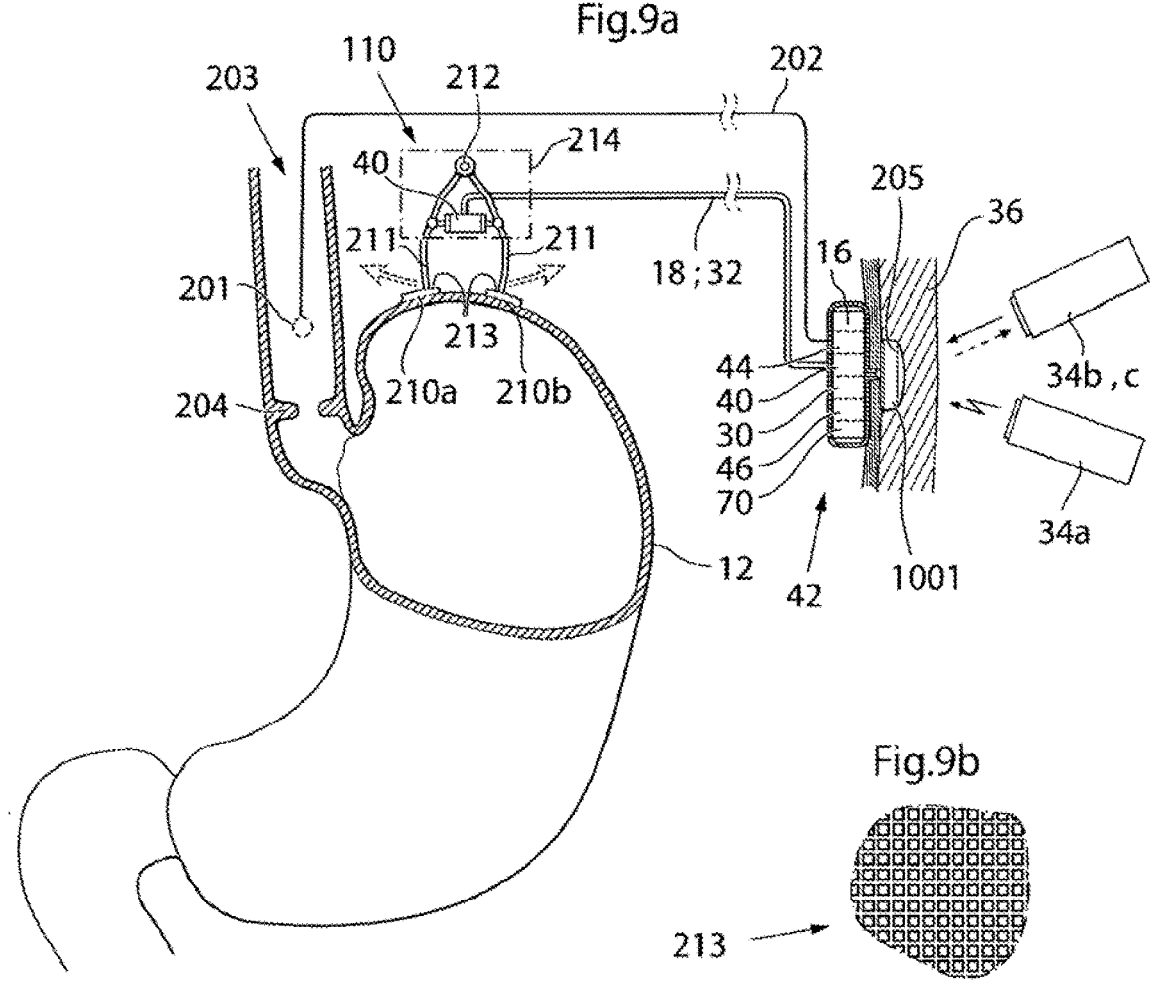
FIG. 9a shows an embodiment wherein the stretching device is a mechanical stretching device, according to a third embodiment.
Figure 9B:
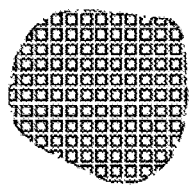
FIG. 9b shows a mesh adapted to assist in the fixation of the stretching device.

In a variant, shown in FIG. 9a, the first and/or second fixation portions 210a, 210b, respectively, exhibit a structure adapted to be in contact with the stomach wall 12 to promote growth in of human tissue to secure the long term placement of the stretching device 110 attached to the stomach wall 12. This structure preferably comprises a net like structure 213. The fixation portions 210a, 210b may be adapted to keep the stretching device 110 in place by sutures or staplers between the fixation portion and the stomach wall 12 to secure the short term placement of the stretching device 110. In turns of mechanical operation the stretching device 110 according to the embodiment shown in FIG. 9a functions in accordance with the device described with reference to FIG. 7. FIG. 9b shows a fixation device 213 comprising a net like structure adapted to propagate the growth-in of fibrotic tissue to fixate the two fixating portions to the stomach wall 12.

Figure 9C:
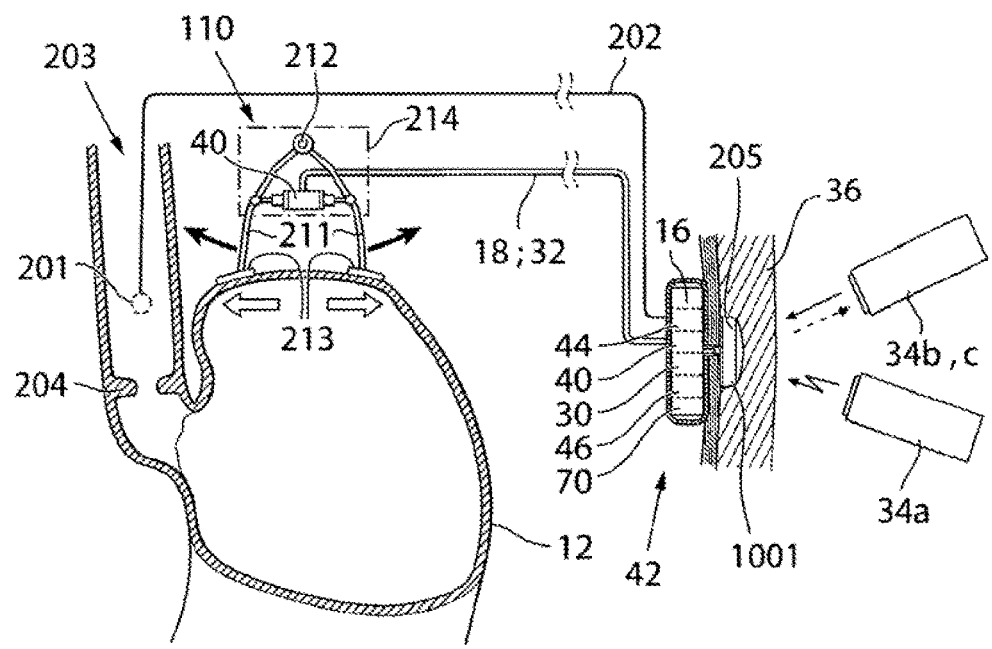
FIG. 9c shows an embodiment wherein the stretching device is a mechanical stretching device, according to a fourth embodiment.

FIG. 9c shows the stretching device according to the embodiment of FIG. 9a in a second state, in which the two fixating portions have been separated from each other and the stomach 12 has been stretched.

Figure 10A:
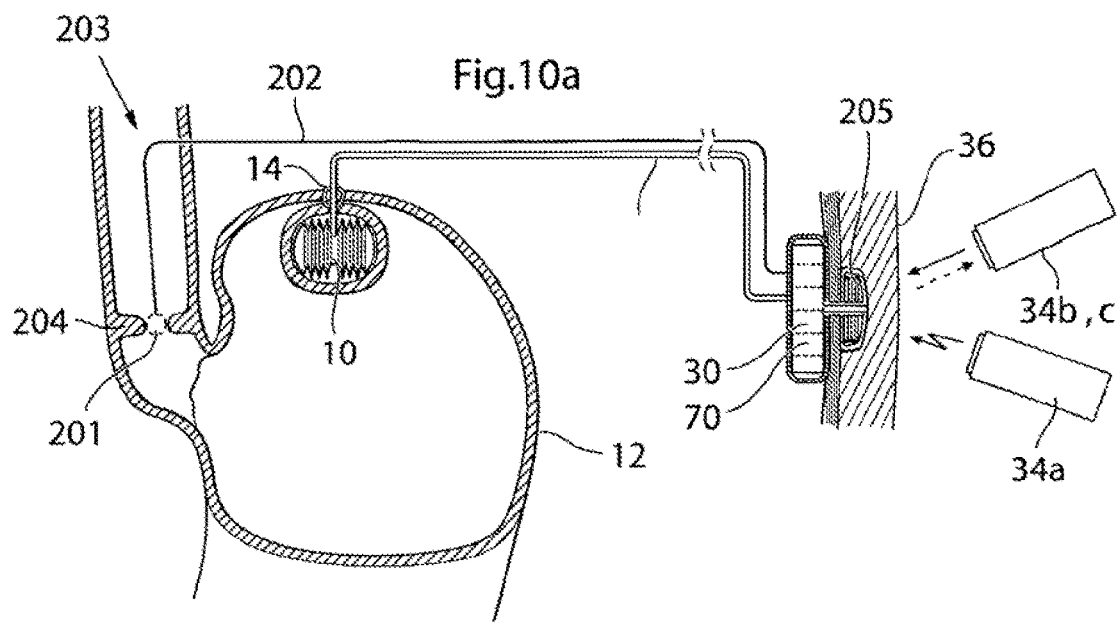
FIG. 10a shows an embodiment wherein the stretching device is a mechanical stretching device, according to a fifth embodiment.

FIG. 10a shows the stretching device according to an embodiment in which the stretching device is an electrical mechanical stretching device connected to a control assembly 42 through a power supply line 32'. The power supply line 32 is connected to a power transforming device 30 in contact with a receiver of wireless energy 205, such as a coil, which receives energy from a transmitter of wireless energy 34a. The control assembly may furthermore comprise a battery 70 for storing energy received from the wireless energy transmission device 34a. The control assembly receives input from a sensor 201, which according to this embodiment is a strain gauge measuring the contraction and/or relaxation of the cardia 204.

Figure 10B:
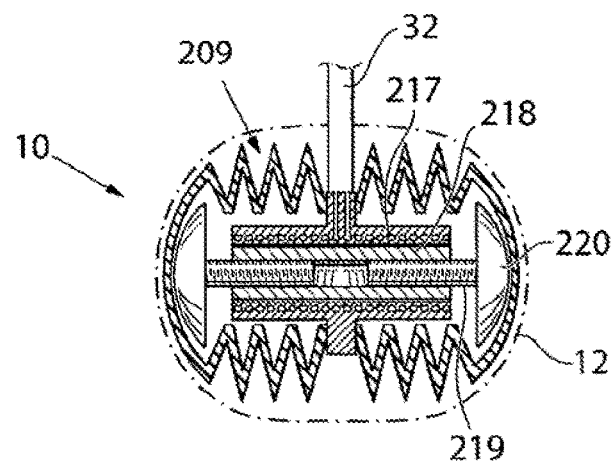
FIG. 10b shows an embodiment wherein the stretching device is a mechanical stretching device, according to a fifth embodiment, in greater detail, in a first state.

FIG. 10b shows the stretching device 10 in further detail. The stretching device 10 comprises a housing having a bellows structure 209 made of a flexible material so as to enable the wall portions to move. The power supply line 32 is connected to a stator 217 of an electrical motor, said motor further comprising a rotor 218 which comprises a thread that interacts with a displaceable member 219 comprising a corresponding thread. The displacing member is rotatably fixated to a housing contacting member 220 which pushes against the housing for affecting the volume of the stretching device and thereby stretching the stomach 12.

Figure 10C:
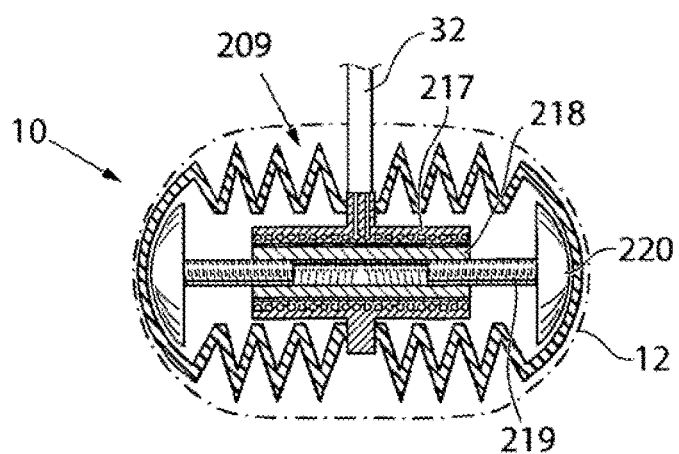
FIG. 10c shows an embodiment wherein the stretching device is a mechanical stretching device, according to a fifth embodiment, in greater detail, in a second state.

FIG. 10c shows the stretching device according to FIG. 10b in a second state, in which the stretching device is expanded and thereby stretches the stomach wall 12.

Figure 11A:
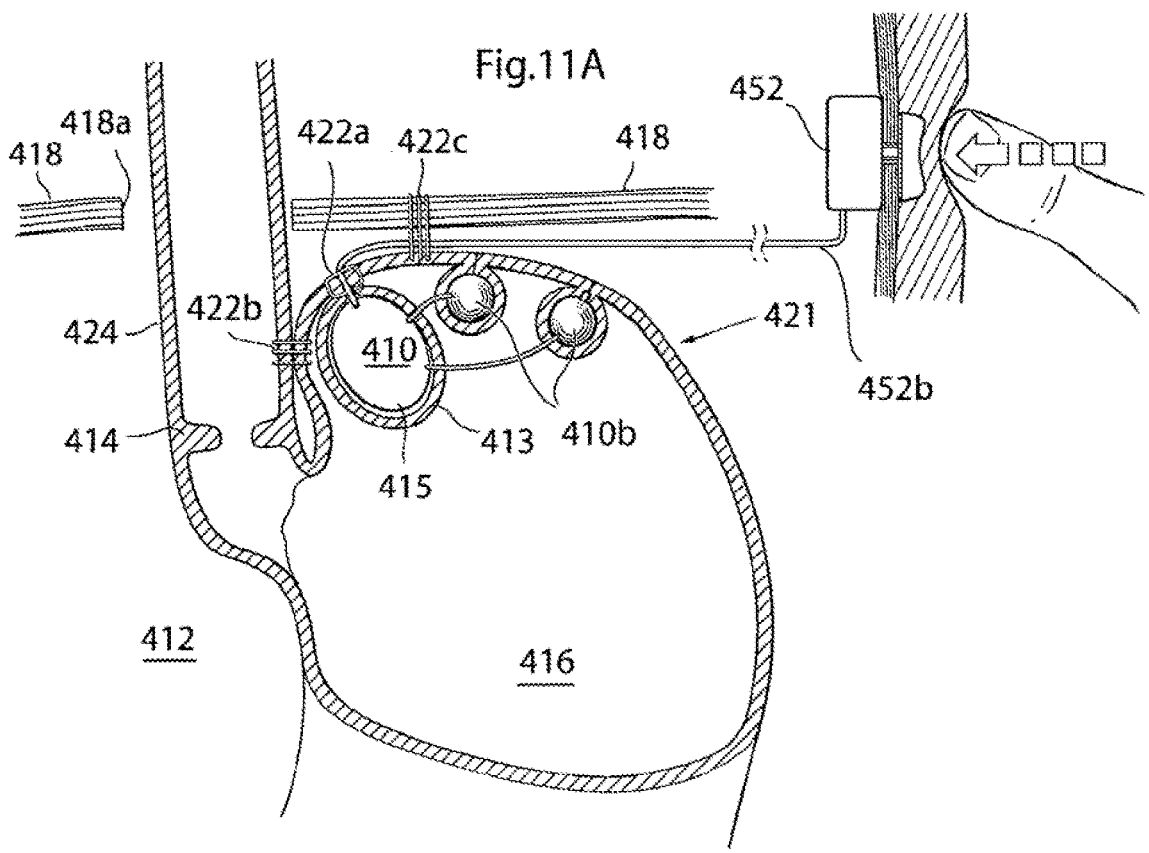
FIG. 11a shows an embodiment where the stretching device is combined with a device for treating reflux decease, according to a first embodiment.

FIG. 11a shows an embodiment in which a device adapted to treat reflux disease is combined with the stretching device according to any of the embodiments above. After invagination of the device 410 in the fundus 416, a fixation consisting of a number of stomach-to-stomach sutures or staples 422a is applied to keep the invagination intact in the short term. A second fixation consisting of a number of sutures or staples 422b is provided to hold the device 410 in position above the cardia 414. The sutures or staples 422b are applied between the wall of the fundus 416 and the wall of the esophagus 424. Additionally, a third fixation in the form of sutures or staples 422c may be provided between the wall of the fundus 416 and the diaphragm 418, again, to hold the device 410 in position above the cardia 414.

In this fourth embodiment depicted in FIG. 11a, the size of the reflux disease treatment device 410 can be regulated while being implanted. The reflux disease treatment device 410 is associated with a subcutaneous hydraulic reservoir 452 connected to the reflux disease treatment device 410, by a lead 452b whereby a non-invasive regulation can be performed by manually pressing the reservoir 452. Pressing the reservoir 452 displaces hydraulic fluid from the reservoir 452 to the smaller chambers 410b via the lead 452b. The reflux disease treatment device 410 is, in turn, connected to one or more smaller chambers 410b. In this manner, the patient may adjust the size of the reflux treatment device 410 in a manner adapted to the treatment.

Furthermore, the embodiment above may alternatively be used to also treat obesity. The device may, in this embodiment, be adapted to treat obesity by using the volume of the reflux disease body to contain a fluid, and further using one or several smaller chambers 410b connected to the device body with a pump to be filled with fluid to expand and thereby stretch the fundus wall to create satiety. The small chambers 410b are also adapted to be invaginated to in the fundus stomach wall, and when filled with fluid, an expansion of the stomach occurs that results in human sensor feedback creating satiety. The subcutaneous hydraulic reservoir/pump enables the patient to conveniently pump hydraulic fluid to fill the small chambers 410b to create a feeling of satiety as he or she wishes.

Figure 11B:
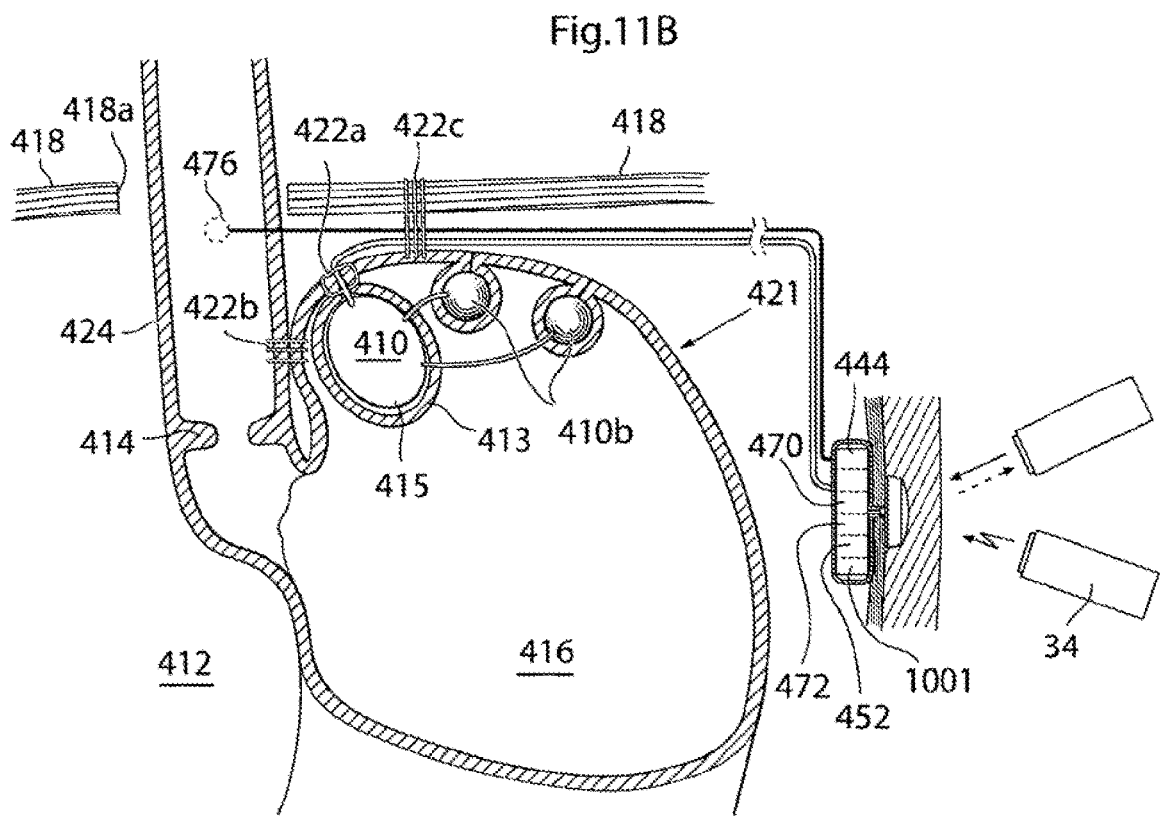
FIG. 11b shows an embodiment where the stretching device is combined with a device for treating reflux decease, according to a second embodiment.

An alternative embodiment is shown in FIG. 11b. This embodiment is substantially similar to the one shown in FIG. 11a but differs in how the reflux treatment device 410 and chambers 410b are controlled. Here, the chambers 410b are not controlled by a subcutaneous pump but a powered internal control unit 456. The internal control unit 456 comprises means for the patient to control the device 410 in how it shall be used regarding treatment of reflux and/or obesity. It may also comprise means of supplying power to the device.

The internal control unit 456 may comprise a battery 470, an electric switch 472, a motor/pump 444, a reservoir 452, an injection port 1001. An energy transmission device 34 with a remote control is adapted for controlling and powering the device. The items being selected depending on the circumstances. e.g. if the device is electrically, hydraulically, pneumatically or mechanically operated.

The device 410 may be used for keeping electronics and/or an energy source and/or hydraulic fluid.

Figure 12A:
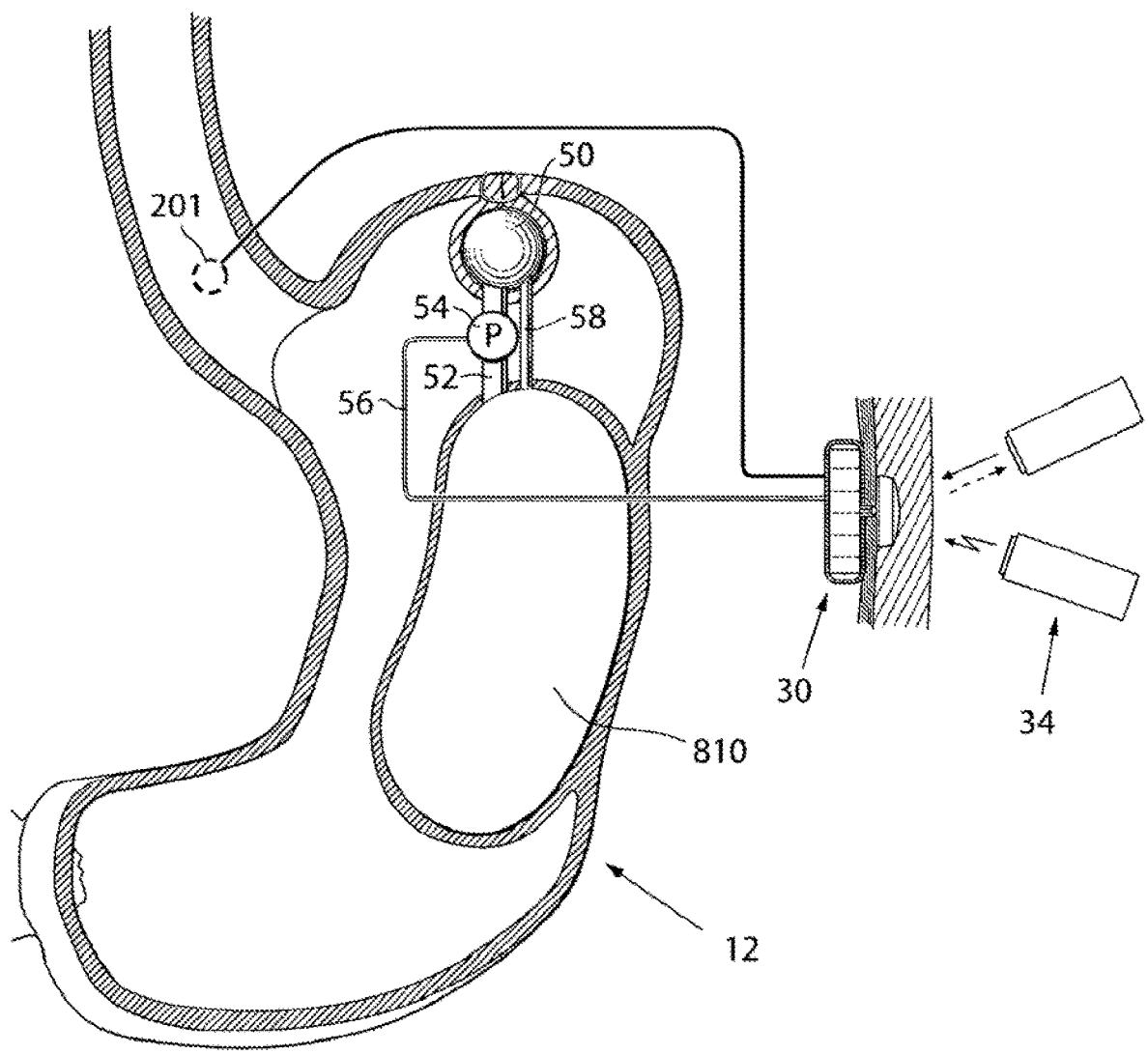
FIG. 12a shows an embodiment where the stretching device is combined with a volume filling device.

FIG. 12a shows an adjustable volume filling device 810, which is invaginated in the stomach wall of a patient's stomach 12. The volume filling device 810 is adapted to take up space in the stomach and thereby reduce the volume in which food can be placed. Additionally, an adjustable stretching device 10 according to any of the embodiments is invaginated in the stomach fundus wall of the patient. It is preferred that the volume filling device 810 is substantially larger than the stretching device 10.

The volume filling device 810 and the stretching device 10 are in fluid communication with each other via a first fluid tube 52, in which a pump 54 is provided. The pump 54 is under the control from an energy transforming device 30, which is adapted to supply the pump 54 with energy via a power supply line 56. The energy transforming device 30 is also connected to a sensor 201 provided in the esophagus of the patient so that food intake can be detected.

The volume filling device 810 and the stretching device 10 are also in fluid communication with each other via a second fluid tube 58, which preferably has a smaller cross-sectional area than the first fluid tube 52.

The operation of this arrangement is as follows. The volume filling device 810 functions as in the above described embodiments, i.e., it reduces the size of the food cavity of the patient's stomach 12. Additionally, when the stretching device 10 is enlarged by pumping fluid from the volume filling device 810 and to the stretching device 10 by means of the pump 54, the stomach fundus wall is stretched, creating a feeling of satiety for the patient. Thus, for example when food intake is detected by means of the sensor 201, fluid is automatically pumped into the stretching device 10 to increase the feeling of satiety and thereby limit the food intake.

When fluid has been injected into the stretching device 10, the internal pressure therein is higher than the internal pressure in the volume filling device 810. This difference in pressure will create a flow of fluid in the second, preferably narrower tube 58 from the stretching device 10 to the volume filling device 810. The flow rate will be determined by among other things the difference in pressure and the cross-sectional area of the second tube 58. It is preferred that the second tube is so dimensioned, that the pressures in the volume filling device 810 and the stretching device 10 will return to equilibrium after 3 hours after fluid has been injected into the stretching device 10 to create the feeling of satiety.

In this embodiment, the function of the second tube 58 is to allow fluid to return from the stretching device 10 to the volume filling device 810. It will be appreciated that this function also can be performed by the pump 54 in the first tube 52 and that the second tube 58 then can be omitted.

Figure 12B:
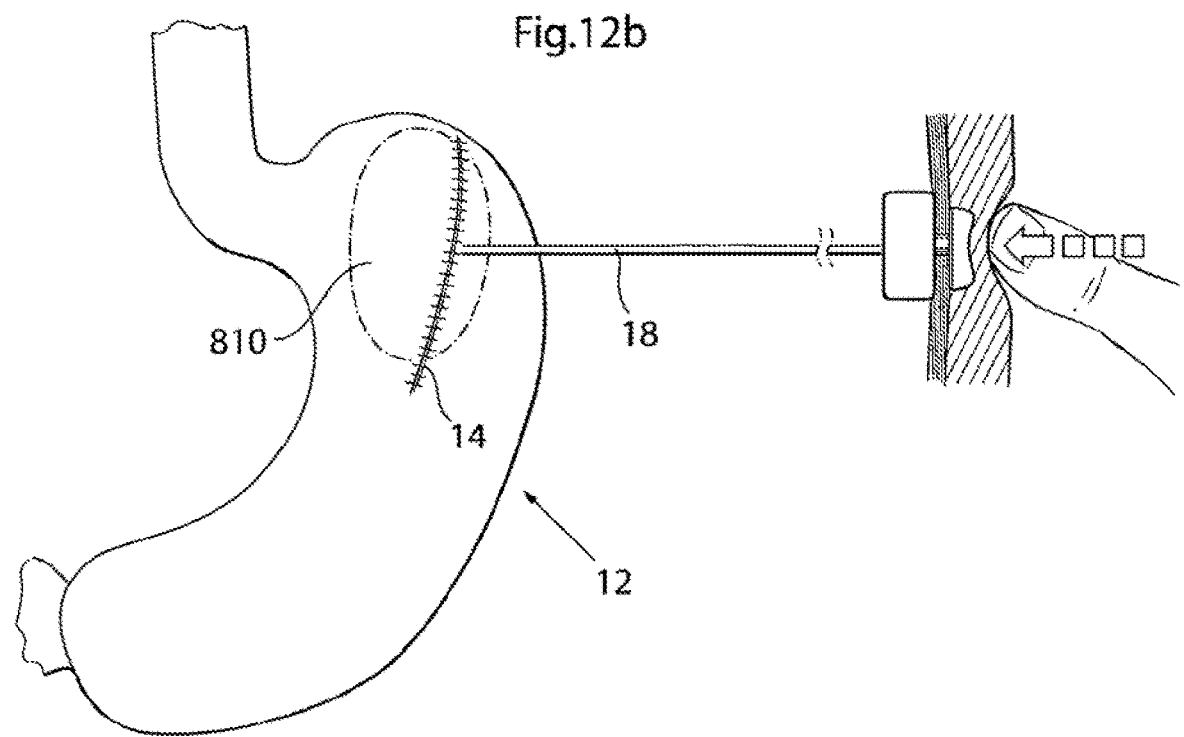
FIG. 12b shows yet another embodiment of the stretching device, in a manual version.

Yet an alternative embodiment of a device for treating obesity will now be described with reference to FIG. 12b, which shows a stomach 12 of a patient who is treated for obesity. The device comprises a volume filling device 810 in the form of an inflatable device 10 which is invaginated in the wall 12a of the patient's stomach 12. However, in this case the invagination has been performed in the fundus, i.e., the upper portion of the stomach, where the number of receptors in the stomach wall is large, and the inflatable device functions as a stretching device for part of the stomach fundus wall.

A regulation reservoir for fluids is connected to the inflatable device by means of a conduit 18 in the form of a tube. The inflatable device 810 is thereby adapted to be regulated, preferably non-invasively, by moving liquid or air from the regulation reservoir to the chamber formed by the inflatable device 810. The regulation of the inflatable device 810 preferably comprises a reversed servo, i.e., a small volume is actuated for example by the patient's finger and this small volume is in connection with a larger volume, i.e., the regulation reservoir.

Thus, the inflatable device 810 is placed outside the stomach wall and is adapted to stretch a part of the stomach fundus wall, thereby affecting the patient's appetite. By enlarging the size of the stretching device, the stomach fundus wall surrounding the inflatable stretching device 810 is stretched since the circumference of the inflatable stretching device 810 is increased. By this stretching, the receptors in the stomach wall indicate that the stomach is full, thereby creating a feeling of satiety to the patient. Correspondingly, when the stretching device 810 is contracted, the receptors indicate that the stomach is not full, thereby returning the feeling of hunger. It will be appreciated that this embodiment combines the effects of both reducing the volume of the stomach food cavity and stretching part of the stomach wall 12, thereby increasing the treatment effect.

The expansion and contraction of the stretching device 810 can be performed under direct control of the patient. Alternatively, the expansion and contraction can be performed according to a pre-programmed schedule.

Figure 12C:
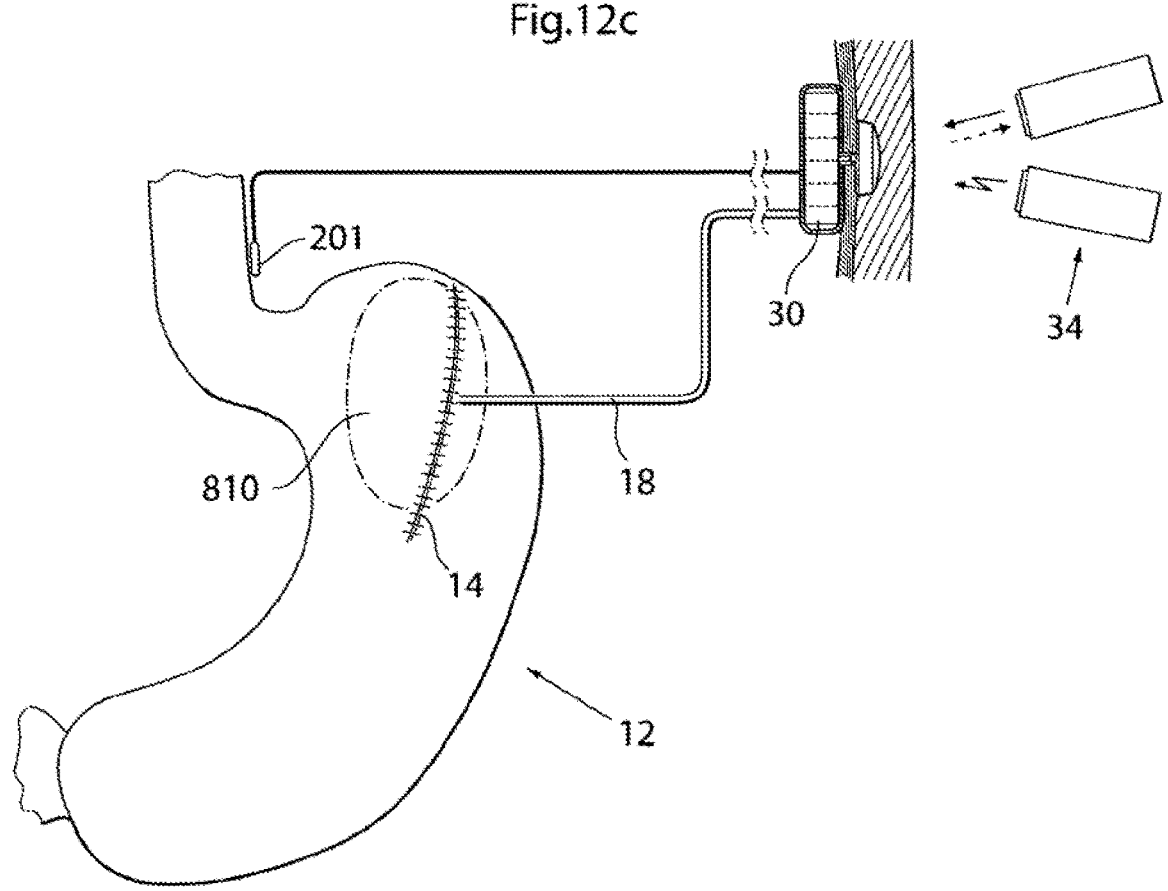
FIG. 12c shows yet another embodiment of the stretching device, in an automatic version.

In a preferred embodiment, shown in FIG. 12*c*, a sensor 201 is provided at a suitable position, such as at the esophagus. The volume filling device 810 in the form of the inflatable stretching device is similar to the one shown in FIG. 12*b*. By providing one or more sensors, the device for treating obesity can be automated in that the size of the volume filling device 810 in the form of the inflatable stretching device is adjusted depending on the amount of food entering the food cavity of the stomach. The fluid is thereby moved between the inflatable volume filling device 810 and a fluid reservoir.

System

A obesity treatment system, generally designated 28 and comprising a stretching device as described above will now be described with reference to FIGS. 13-29

The system of FIG. 8 comprises a stretching device 10 placed in the abdomen of the patient. An internal energy source in the form of an implanted energy transforming device 30 is adapted to supply energy consuming components of the obesity treatment system with energy via a power supply line 32. An external energy transmission device 34 includes a wireless remote control transmitting a wireless signal, which is received by a signal receiver, which may be incorporated in the implanted energy transforming device 30 or be separated therefrom. The implanted energy transforming device 30 transforms energy from the signal into electric energy which is supplied via the power supply line 32.

The system of FIG. 8 is shown in a more generalized block diagram form in FIG. 15, wherein the patient's skin 36, generally shown by a vertical line, separates the interior of the patient to the right of the line from the exterior to the left of the line.

FIG. 13 shows a simplified block diagram showing the stretching device 10, the energy transforming device 30 powering the stretching device via power supply line 32, and the external energy transmission device 34.

Figure 17:
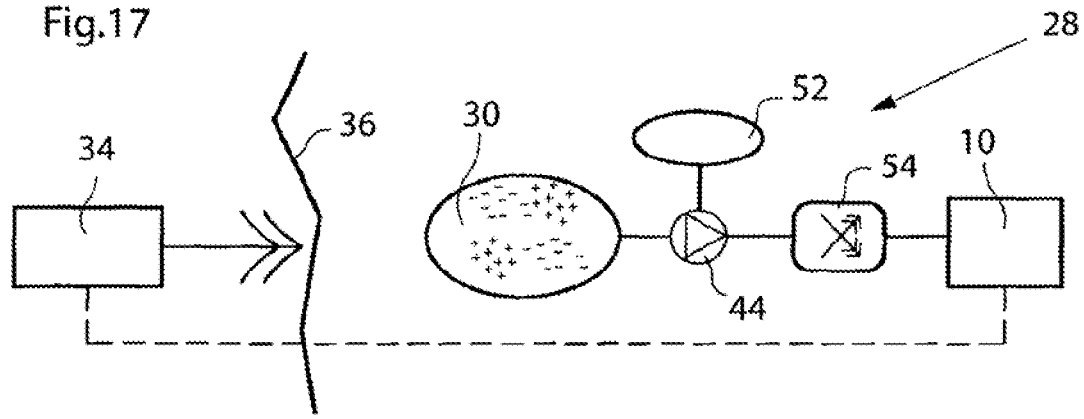

FIG. 14 shows an embodiment of the invention identical to that of FIG. 17, except that a reversing device in the form of an electric switch 38 operable by polarized energy also is implanted in the patient for reversing the stretching device 10. The wireless remote control of the external energy transmission device 34 transmits a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the stretching device 10.

FIG. 15 shows an embodiment of the invention identical to that of FIG. 13, except that an operation device 40 implanted in the patient for regulating the stretching device 10 is provided between the implanted energy transforming device 30 and the stretching device 10. This operation device can be in the form of a motor 40, such as an electric servomotor. The motor 40 is powered with energy from the implanted energy transforming device 30, as the remote control of the external energy transmission device 34 transmits a wireless signal to the receiver of the implanted energy transforming device 30.

FIG. 16 shows an embodiment of the invention identical to that of FIG. 17, except that it also comprises an operation device is in the form of an assembly 42 including a motor/pump unit 78 and a fluid reservoir 46 is implanted in the patient. In this case the stretching device 10 is hydraulically operated, i.e. hydraulic fluid is pumped by the motor/pump unit 44 from the fluid reservoir 46 through a conduit 48 to the stretching device 10 to operate the stretching device, and hydraulic fluid is pumped by the motor/pump unit 44 back from the stretching device 10 to the fluid reservoir 46 to return the stretching device to a starting position. The implanted energy transforming device 30 transforms wireless energy into a current, for example a polarized current, for powering the motor/pump unit 44 via an electric power supply line 50.

Instead of a hydraulically operated stretching device 10, it is also envisaged that the operation device comprises a pneumatic operation device. In this case, pressurized air can be used for regulation and the fluid reservoir is replaced by an air chamber and the fluid is replaced by air.

In all of these embodiments the energy transforming device 30 may include a rechargeable accumulator like a battery or a capacitor to be charged by the wireless energy and supplies energy for any energy consuming part of the device.

The external energy transmission device 34 is preferably wireless and may include a remotely controlled control device for controlling the device from outside the human body.

Such a control device may include a wireless remote control as well as a manual control of any implanted part to make contact with by the patient's hand most likely indirect for example a button to press placed under the skin.

FIG. 17 shows an embodiment of the invention comprising the external energy transmission device 34 with its wireless remote control, the stretching device 10, in this case hydraulically operated, and the implanted energy transforming device 30, and further comprising a hydraulic fluid reservoir 52, a motor/pump unit 44 and an reversing device in the form of a hydraulic valve shifting device 54, all implanted in the patient. Of course the hydraulic operation could easily be performed by just changing the pumping direction and the hydraulic valve may therefore be omitted. The remote control may be a device separated from the external energy transmission or included in the same. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the stretching device 10. The remote control of the external energy transmission device 34 controls the hydraulic valve shifting device 54 to shift the hydraulic fluid flow direction between one direction in which the fluid is pumped by the motor/pump unit 44 from the hydraulic fluid reservoir 52 to the stretching device 10 to operate the stretching device, and another opposite direction in which the fluid is pumped by the motor/pump unit 44 back from the stretching device 10 to the hydraulic fluid reservoir 52 to return the stretching device to a starting position.

Figure 18:
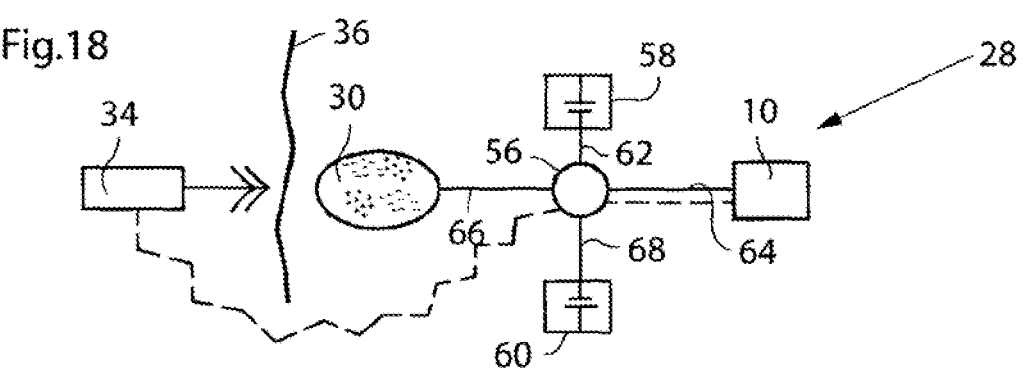

FIG. 18 shows an embodiment of the invention identical to that of FIG. 17, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the stretching device 10. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the stretching device 10.

The internal control unit is preferably programmable from outside the patient's body. In a preferred embodiment, the internal control unit is programmed to regulate the stretching device 10 to stretch the stomach according to a pre-programmed time-schedule or to input from any sensor sensing any possible physical parameter of the patient or any functional parameter of the device.

In accordance with an alternative, the capacitor 60 in the embodiment of FIG. 18 may be omitted. In accordance with another alternative, the accumulator 58 in this embodiment may be omitted.

Figure 19:
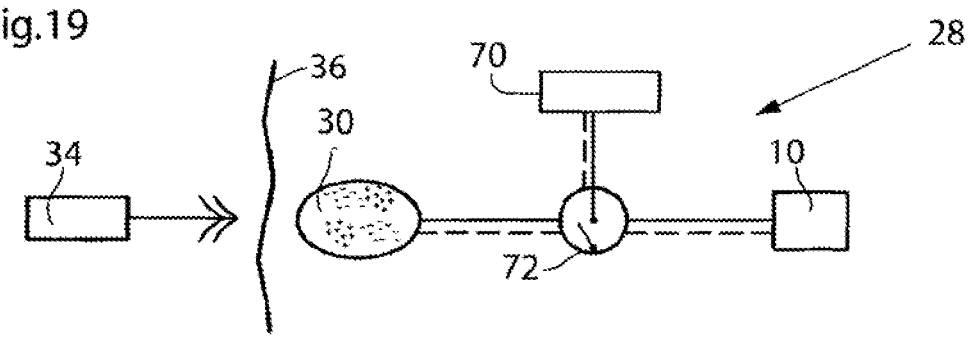

FIG. 19 shows an embodiment of the invention identical to that of FIG. 13, except that a battery 70 for supplying energy for the operation of the stretching device 10 and an electric switch 72 for switching the operation of the stretching device 10 also is implanted in the patient. The electric switch 72 is operated by the energy supplied by the implanted energy transforming device 30 to switch from an off mode, in which the battery 70 is not in use, to an on mode, in which the battery 70 supplies energy for the operation of the stretching device 10.

Figure 20:
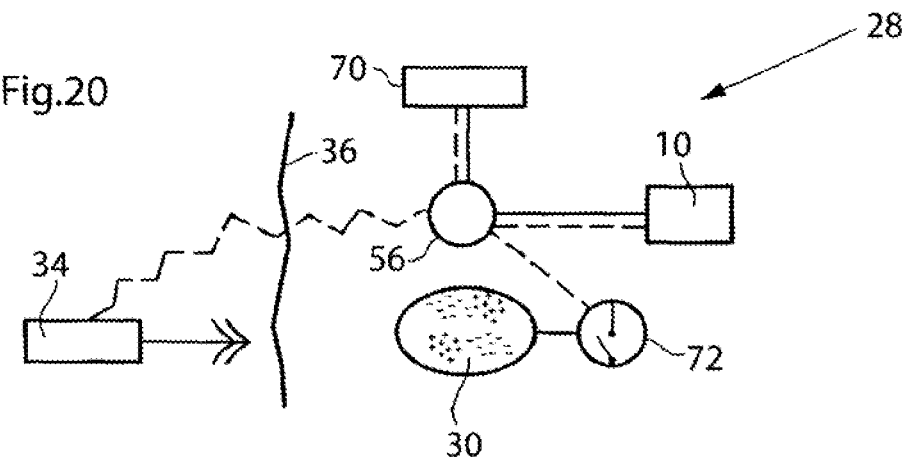

FIG. 20 shows an embodiment of the invention identical to that of FIG. 19, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the stretching device 10.

FIG. 21 shows an embodiment of the invention identical to that of FIG. 20, except that an accumulator 58 is substituted for the battery 70 and the implanted components are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the stretching device 10.

FIG. 22 shows an embodiment of the invention identical to that of FIG. 21, except that a battery 70 also is implanted in the patient and the implanted components are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the stretching device 10.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the stretching device 10.

It should be understood that the switch should be interpreted in its broadest embodiment. This means an FPGA or a DA converter or any other electronic component or circuit may switch power on and off preferably being controlled from outside the body or by an internal control unit.

FIG. 23 shows an embodiment of the invention identical to that of FIG. 19, except that a motor 40, a mechanical reversing device in the form of a gear box 74, and an internal control unit 56 for controlling the gear box 74 also is implanted in the patient. The internal control unit 56 controls the gear box 74 to reverse the function performed by the stretching device 10 (mechanically operated). Even simpler is to switch the direction of the motor electronically.

FIG. 24 shows an embodiment of the invention identical to that of FIG. 22 except that the implanted components are interconnected differently. Thus, in this case the internal control unit 56 is powered by the battery 70 when the accumulator 58, suitably a capacitor, activates the electric switch 72 to switch to an on mode. When the electric switch 72 is in its on mode the internal control unit 56 is permitted to control the battery 70 to supply, or not supply, energy for the operation of the stretching device 10.

Figure 25:
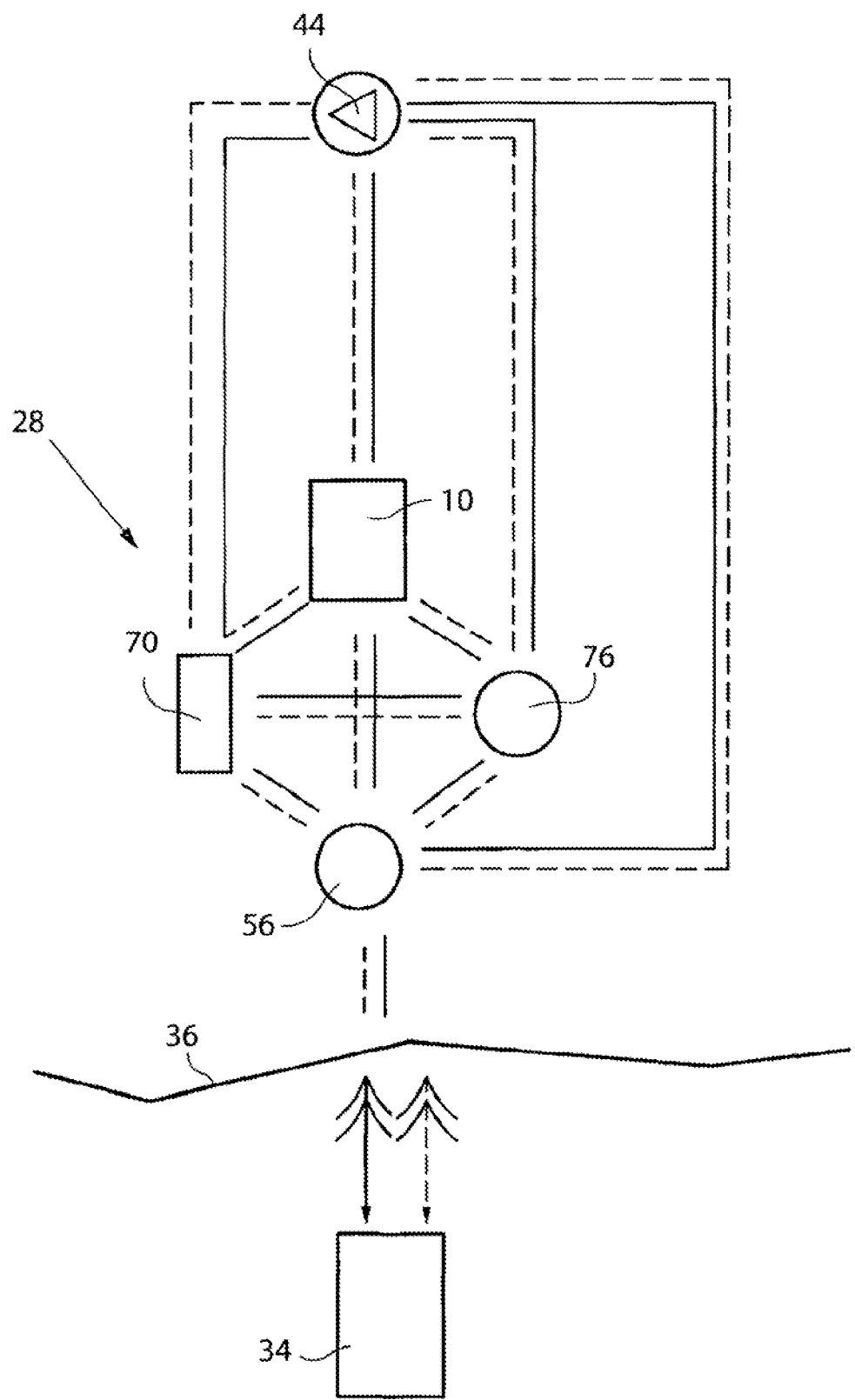

FIG. 25 schematically shows conceivable combinations of implanted components of the device for achieving various communication options. Basically, there are the stretching device 10, the internal control unit 56, motor or pump unit 44, and the external energy transmission device 34 including the external wireless remote control. As already described above the wireless remote control transmits a control signal which is received by the internal control unit 56, which in turn controls the various implanted components of the device.

A feedback device, preferably in the form of a sensor 76, may be implanted in the patient for sensing a physical parameter of the patient, such as a contraction wave in the esophagus 203 informing the patient is eating. The internal control unit 56, or alternatively the external wireless remote control of the external energy transmission device 34, may control the stretching device 10 in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the stretching device 10 from inside the patient's body to the outside thereof.

Alternatively, the sensor 76 may be arranged to sense a functional parameter of the stretching device 10.

Where the motor/pump unit 44 and battery 70 for powering the motor/pump unit 44 are implanted, the battery 70 may be equipped with a transceiver for sending information on the condition of the battery 70. To be more precise, when charging a battery or accumulator with energy feedback information related to said charging process is sent and the energy supply is changed accordingly.

Figure 26:
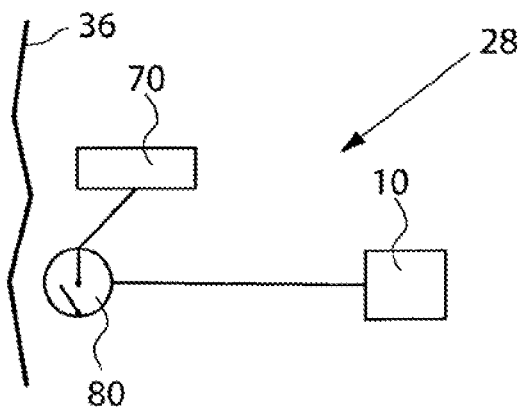

FIG. 26 shows an alternative embodiment wherein the stretching device 10 is regulated from outside the patient's body. The obesity treatment system 28 comprises a stretching device 10 connected to a battery 70 via a subcutaneous switch 80. Thus, the regulation of the stretching device 10 is performed non-invasively by manually pressing the subcutaneous switch, whereby the operation of the stretching device 10 is switched on and off. It will be appreciated that the shown embodiment is a simplification and that additional components, such as an internal control unit or any other part disclosed in the present application can be added to the obesity treatment system.

Figure 27:
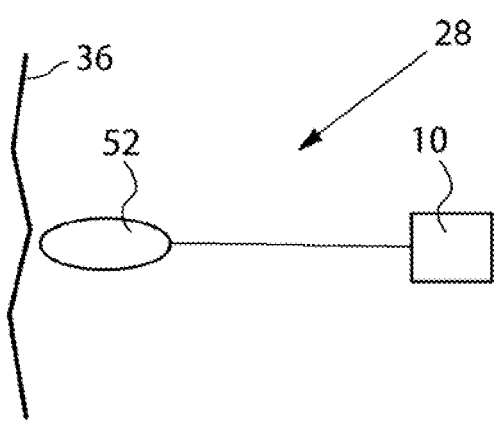

FIG. 27 shows an alternative embodiment, wherein the obesity treatment system 28 comprises a stretching device 10 in fluid connection with a hydraulic fluid reservoir 52. Non-invasive regulation is performed by manually pressing the hydraulic reservoir connected to the stretching device 10.

A further embodiment of a system according to the invention comprises a feedback device for sending information from inside the patient's body to the outside thereof to give feedback information related to at least one functional parameter of the stretching device or system or a physical parameter of the patient, thereby optimizing the performance of the system.

One preferred functional parameter of the device is correlated to the transfer of energy for charging the internal energy source.

Figure 28:
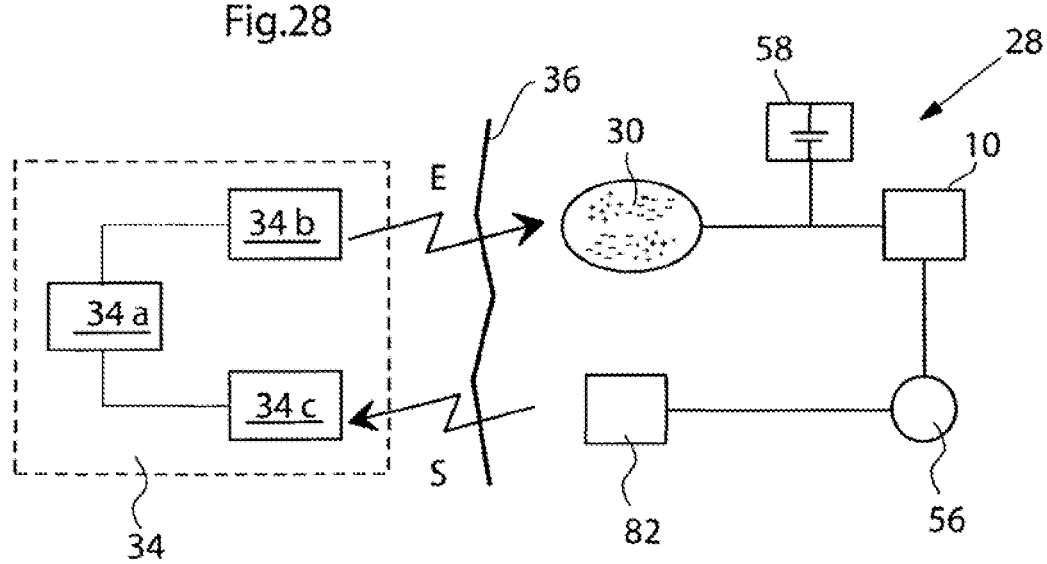

In FIG. 28, an arrangement is schematically illustrated for supplying an accurate amount of energy to a obesity treatment system 28 implanted in a patient, whose skin 36 is indicated by a vertical line. A stretching device 10 is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The implanted energy transforming device 30 is adapted to receive wireless energy E transmitted from an external energy source 34a provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34a and an adjacent secondary coil arranged in the implanted energy transforming device 30. When an electric current is fed through the primary coil, energy in the form of a voltage is induced in the secondary coil which can be used to operate a stretching device, e.g. after storing the incoming energy in an energy storing device or accumulator, such as a battery or a capacitor. However, the present invention is generally not limited to any particular energy transfer technique, TET devices or energy storing devices, and any kind of wireless energy may be used.

The amount of energy received inside the body to the device may be compared with the energy used by the device. The term used by the device is then understood to include also energy stored by the device. The amount of transferred energy can be regulated by means of an external control unit 34b controlling the external energy source 34a based on the determined energy balance, as described above. In order to transfer the correct amount of energy, the energy balance and the required amount of energy can be determined by means of an internal control unit 56 connected to the stretching device 10. The internal control unit 56 may thus be arranged to receive various measurements obtained by suitable sensors or the like, not shown, measuring certain characteristics of the stretching device 10, somehow reflecting the required amount of energy needed for proper operation of the stretching device 10. Moreover, the current condition of the patient may also be detected by means of suitable measuring devices or sensors, in order to provide parameters reflecting the patient's condition. Hence, such characteristics and/or parameters may be related to the current state of the stretching device 10, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the stretching device 10. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the stretching device 10, and also to avoid excessive heating, it is clearly understood that the battery should be charged optimally by receiving a correct amount of energy from the implanted energy transforming device 30, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy) based on measurements made by the above-mentioned sensors or measuring devices on the stretching device 10, or the patient, or an energy storing device if used, or any combination thereof. The internal control unit 56 is further connected to an internal signal transmitter 82, arranged to transmit a control signal reflecting the determined required amount of energy, to an external signal receiver 34c connected to the external control unit 34b. The amount of energy transmitted from the external energy source 34a may then be regulated in response to the received control signal.

Alternatively, sensor measurements can be transmitted directly to the external control unit 34b wherein the energy balance and/or the currently required amount of energy can be determined by the external control unit 34b, thus integrating the above-described function of the internal control unit 56 in the external control unit 34b. In that case, the internal control unit 56 can be omitted and the sensor measurements are supplied directly to the internal signal transmitter 82 which sends the measurements over to the external signal receiver 34c and the external control unit 34b. The energy balance and the currently required amount of energy can then be determined by the external control unit 34b based on those sensor measurements.

Hence, the present solution employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by the stretching device. The stretching device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the stretching device.

The internal signal transmitter 82 and the external signal receiver 34c may be implemented as separate units using suitable signal transfer means, such as radio, IR (Infrared) or ultrasonic signals. Alternatively, the internal signal transmitter 82 and the external signal receiver 34c may be integrated in the implanted energy transforming device 30 and the external energy source 34a, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 28 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34c. Alternatively, the energy balance can be determined by the external control unit 34b instead depending on the implementation, as mentioned above. In that case, the control signal may carry measurement results from various sensors. The amount of energy emitted from the external energy source 34a can then be regulated by the external control unit 34b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34a, such as voltage, current, amplitude, wave frequency and pulse characteristics.

A method is thus provided for controlling transmission of wireless energy supplied to an electrically operable stretching device implanted in a patient. The wireless energy E is transmitted from an external energy source located outside the patient and is received by an internal energy receiver located inside the patient, the internal energy receiver being connected to the stretching device for directly or indirectly supplying received energy thereto. An energy balance is determined between the energy received by the internal energy receiver and the energy used for the stretching device. The transmission of wireless energy E from the external energy source is then controlled based on the determined energy balance.

A system is also provided for controlling transmission of wireless energy supplied to an electrically operable stretching device implanted in a patient. The system is adapted to transmit the wireless energy E from an external energy source located outside the patient which is received by an implanted energy transforming device located inside the patient, the implanted energy transforming device being connected to the stretching device for directly or indirectly supplying received energy thereto. The system is further adapted to determine an energy balance between the energy received by the implanted energy transforming device and the energy used for the stretching device, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the stretching device.

In another embodiment, the external source of energy is controlling from outside the patient's body to release non-magnetic wireless energy, and released non-magnetic wireless energy is used for operating the stretching device.

Those skilled in the art will realize that the above various embodiments according to FIGS. 17-29 could be combined in many different ways. For example, the electric switch 38 operated by polarized energy could be incorporated in any of the embodiments of FIGS. 11, 18-24, the hydraulic valve shifting device 54 could be incorporated in the embodiment of FIG. 16, and the gear box 74 could be incorporated in the embodiment of FIG. 15. Please observe that the switch simply could mean any electronic circuit or component.

Figure 29:
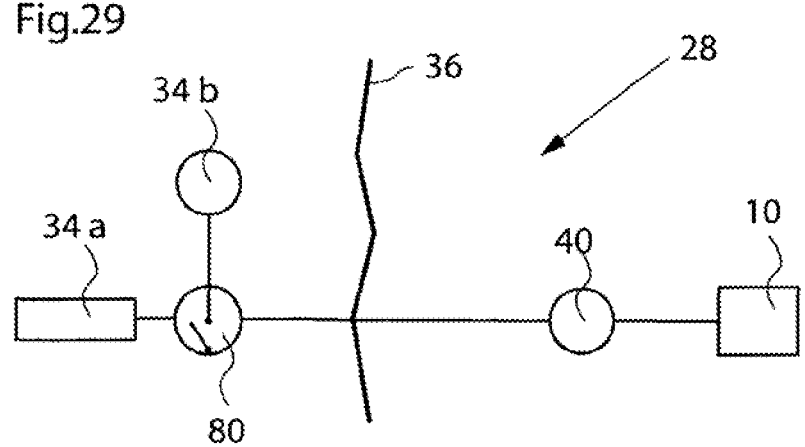

Wireless transfer of energy for operating the stretching device has been described to enable non-invasive operation. It will be appreciated that the stretching device can be operated with wire bound energy as well. One such example is shown in FIG. 29, wherein an external switch 84 is interconnected between the external energy source 34a and an operation device, such as an electric motor regulating the stretching device 10, by means of power lines 86 and 88. An external control unit 34b controls the operation of the external switch to effect proper operation of the stretching device 10.

Hydraulic or Pneumatic Powering

FIGS. 30-33 show in more detail block diagrams of four different ways of hydraulically or pneumatically powering a device for treating obesity according to the invention.

Figure 30:
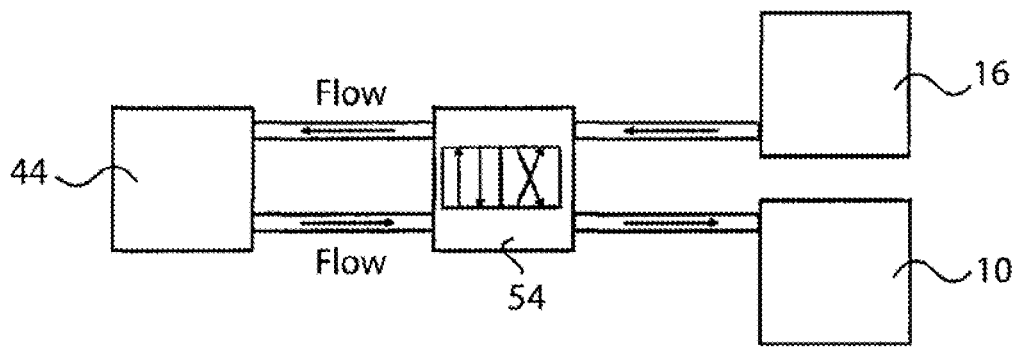

FIG. 30 shows a device for treating obesity as described above with reference to any of FIGS. 1-6. The device comprises a stretching device 10 and further a separate regulation reservoir 16, a one way pump 44 and an alternate valve 54.

Figure 31:
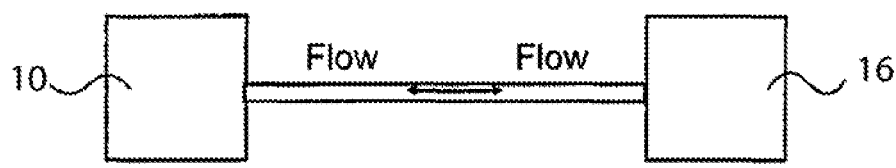

FIG. 31 shows the stretching device 10 and a fluid reservoir 16. By moving the wall of the regulation reservoir or changing the size of the same in any other different way, the adjustment of the stretching device may be performed without any valve, just free passage of fluid any time by moving the reservoir wall.

Figure 32:
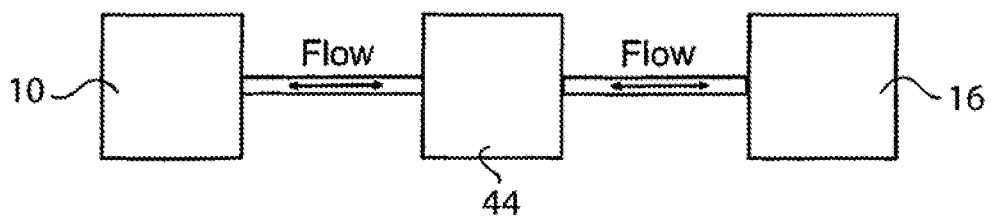

FIG. 32 shows the stretching device 10, a two way pump 44 and the regulation reservoir 16.

Figure 33:
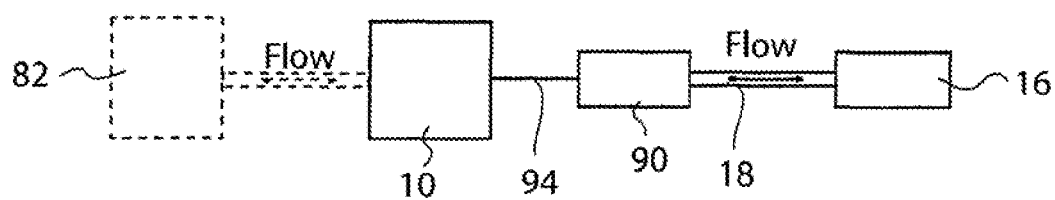
Figure 34:
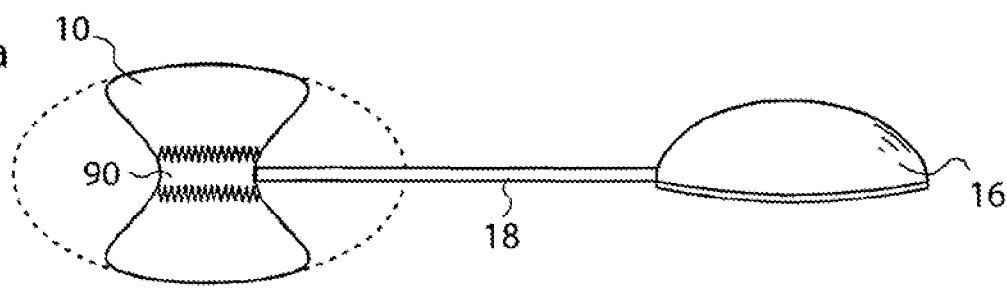
Figure 34:
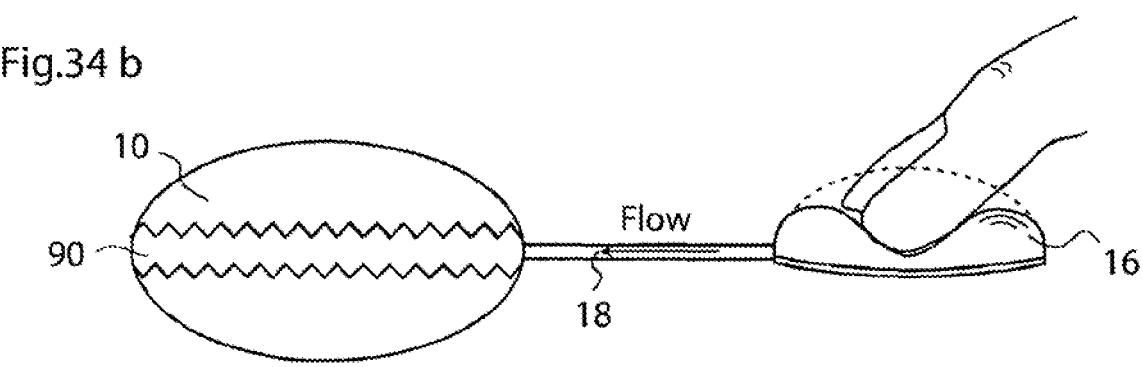
Figure 34:
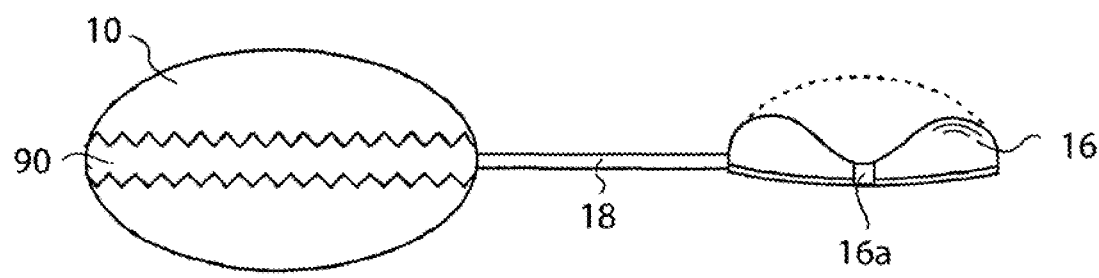
Figure 35:
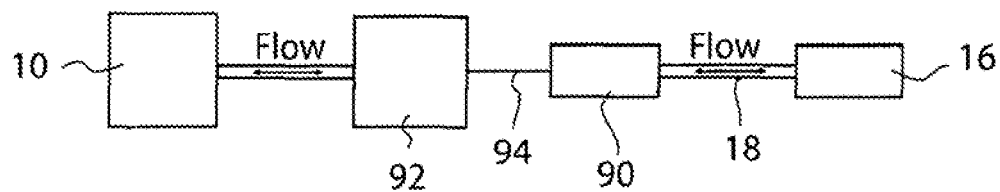
Figure 36:
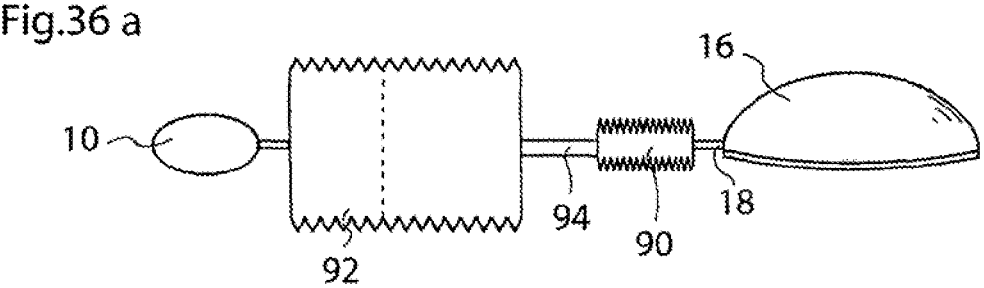
Figure 36:
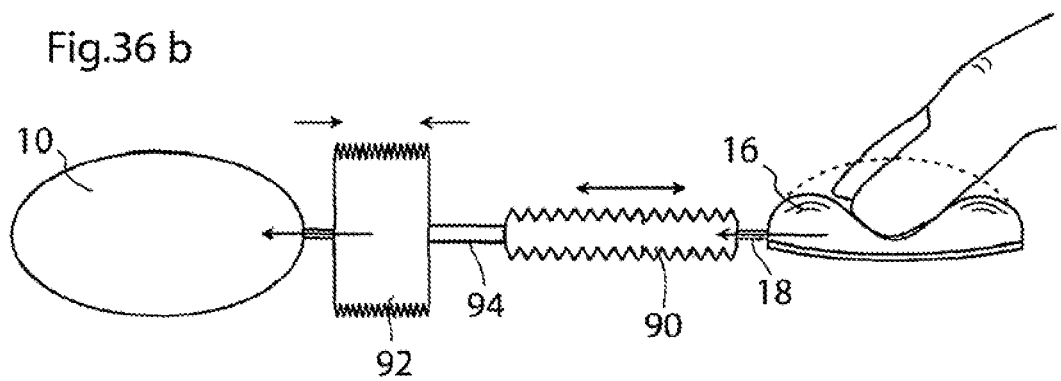
Figure 36:
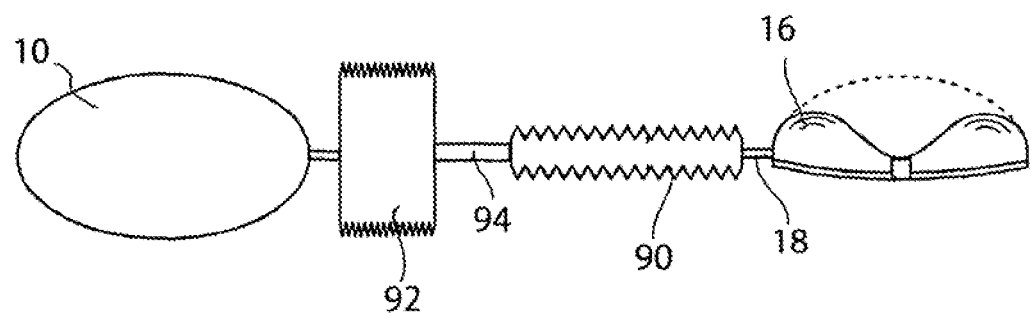

FIG. 33 shows a block diagram of a reversed servo system with a first closed system controlling a second closed system. The servo system comprises a regulation reservoir 16 and a servo reservoir 90. The servo reservoir 90 mechanically controls a stretching device 10 via a mechanical interconnection 94, the stretching device having an expandable/contactable cavity. This cavity is preferably expanded or contracted by supplying hydraulic fluid from the larger adjustable reservoir 92 in fluid connection with the stretching device 10. Alternatively, the cavity contains compressible gas, which can be compressed and expanded under the control of the servo reservoir 90.

The servo reservoir 90 can also be part of the stretching device itself.

In one embodiment, the regulation reservoir is placed subcutaneous under the patient's skin 36 and is operated by pushing the outer surface thereof by means of a finger. This obesity treatment system is illustrated in FIGS. 34*a-c*. In FIG. 34*a*, a flexible subcutaneous regulation reservoir 16 is shown connected to a bulge shaped servo reservoir 90 by means of a conduit 18. This bellow shaped servo reservoir 90 is comprised in a flexible stretching device 10. In the state shown in FIG. 34*a*, the servo reservoir 90 contains a minimum of fluid and most fluid is found in the regulation reservoir 16. Due to the mechanical interconnection between the servo reservoir 90 and the stretching device 10, the outer shape of the stretching device 10 is contracted. i.e., it occupies less than its maximum volume. This maximum volume is shown with dashed lines in the figure.

FIG. 34*b* shows a state wherein a user, such as the patient in with the stretching device is implanted, presses the regulation reservoir 16 so that fluid contained therein is brought to flow through the conduit 18 and into the servo reservoir 90, which, thanks to its bellow shape, expands longitudinally. This expansion in turn expands the stretching device 10 so that it occupies its maximum volume, thereby stretching the stomach wall (not shown) which it contacts.

The regulation reservoir 16 is preferably provided with means for keeping its shape after compression. This means, which is schematically shown as 16*a* in the figure, will thus keep the stretching device 10 in a stretched position also when the user releases the regulation reservoir. In this way, the regulation reservoir essentially operates as an on/off switch for the obesity treatment system.

An alternative embodiment of hydraulic or pneumatic operation will now be described with reference to FIGS. 35 and 36*a-c*. The block diagram shown in FIG. 35 comprises with a first closed system controlling a second closed system. The first system comprises a regulation reservoir 16 and a servo reservoir 90. The servo reservoir 90 mechanically controls a larger adjustable reservoir 92 via a mechanical interconnection 94. A stretching device 10 having an expandable/contactable cavity is in turn controlled by the larger adjustable reservoir 92 by supply of hydraulic fluid from the larger adjustable reservoir 92 in fluid connection with the stretching device 10.

An example of this embodiment will now be described with reference to FIG. 36*a-c*. Like in the previous embodiment, the regulation reservoir is placed subcutaneous under the patient's skin and is operated by pushing the outer surface thereof by means of a finger. The regulation reservoir 16 is in fluid connection with a bellow shaped servo reservoir 90 by means of a conduit 18. In the first closed system 16, 18, 90 shown in FIG. 34*a*, the servo reservoir 90 contains a minimum of fluid and most fluid is found in the regulation reservoir 16.

The servo reservoir 90 is mechanically connected to a larger adjustable reservoir 92, in this example also having a bellow shape but with a larger diameter than the servo reservoir 90. The larger adjustable reservoir 92 is in fluid connection with the stretching device 10. This means that when a user pushes the regulation reservoir 16, thereby displacing fluid from the regulation reservoir 16 to the servo reservoir 90, the expansion of the servo reservoir 90 will displace a larger volume of fluid from the larger adjustable reservoir 92 to the stretching device 10. In other words, in this reversed servo, a small volume in the regulation reservoir is compressed with a higher force and this creates a movement of a larger total area with less force per area unit.

Like in the previous embodiment described above with reference to FIGS. 34*a-c*, the regulation reservoir 16 is preferably provided with means for keeping its shape after compression. This means, which is schematically shown as 16*a* in the figure, will thus keep the stretching device 10 in a stretched position also when the user releases the regulation reservoir. In this way, the regulation reservoir essentially operates as an on/off switch for the obesity treatment system.

Method

A method for surgically treating an obese patient, the method comprising the steps of cutting an opening in the abdominal wall of the patient, dissecting an area around the stomach, placing a device for treating to a part of the stomach wall of the patient, and suturing the stomach wall.

The device for treating obesity is preferably placed in a patient via a laparoscopic abdominal approach, comprising the steps of: inserting a needle or a tube like instrument into the abdomen of the patient's body, using the needle or a tube like instrument to fill the patient's abdomen with gas thereby expanding the patient's abdominal cavity, placing at least two laparoscopic trocars in the patient's body, inserting a camera through one of the laparoscopic trocars into the patient's abdomen, inserting at least one dissecting tool through one of said at least two laparoscopic trocars and dissecting an intended placement area of the patient, and placing a device for treating obesity in connection with the stomach wall.

The methods could further comprise the step of postoperatively regulating the at least one stretching device to: stretch a part of the stomach wall and regulate the stretching device from outside the patient's body to affect the appetite of the patient.

Instruments

An intraluminar method of invaginating a stretching device 10 on the outside of the stomach wall 12 will now be described with reference to FIGS. 5*a-i*. Initially, an instrument 600, preferably a gastroscopic instrument, is inserted into the mouth of the patient, see FIG. 5*a*. The instrument comprises an injection device 601, 602 for injecting either fluid or a device into the stomach of the patient. The instrument 600 further comprises a control unit 606 adapted for controlling the operation of the instrument. To this end, the control unit 606 comprises one or more steering devices, in the embodiment shown in the figure in the form of two joysticks 603 and two control buttons 604. A display 605 is provided for displaying the image provided by an optical device for viewing inside the stomach, such as a camera (not shown) arranged at the outer end of the elongated member 607, see FIGS. 5*e-i*. The camera, which may comprise connecting electrical wires extending along the elongated member, may be assisted by a light source (not shown) placed distally on the elongated member for illuminating the inside of the stomach. The optical device may also comprise optical fibers placed along the elongated member and leading out from the patient's body for external viewing of the inside of the stomach.

Figure 37A:
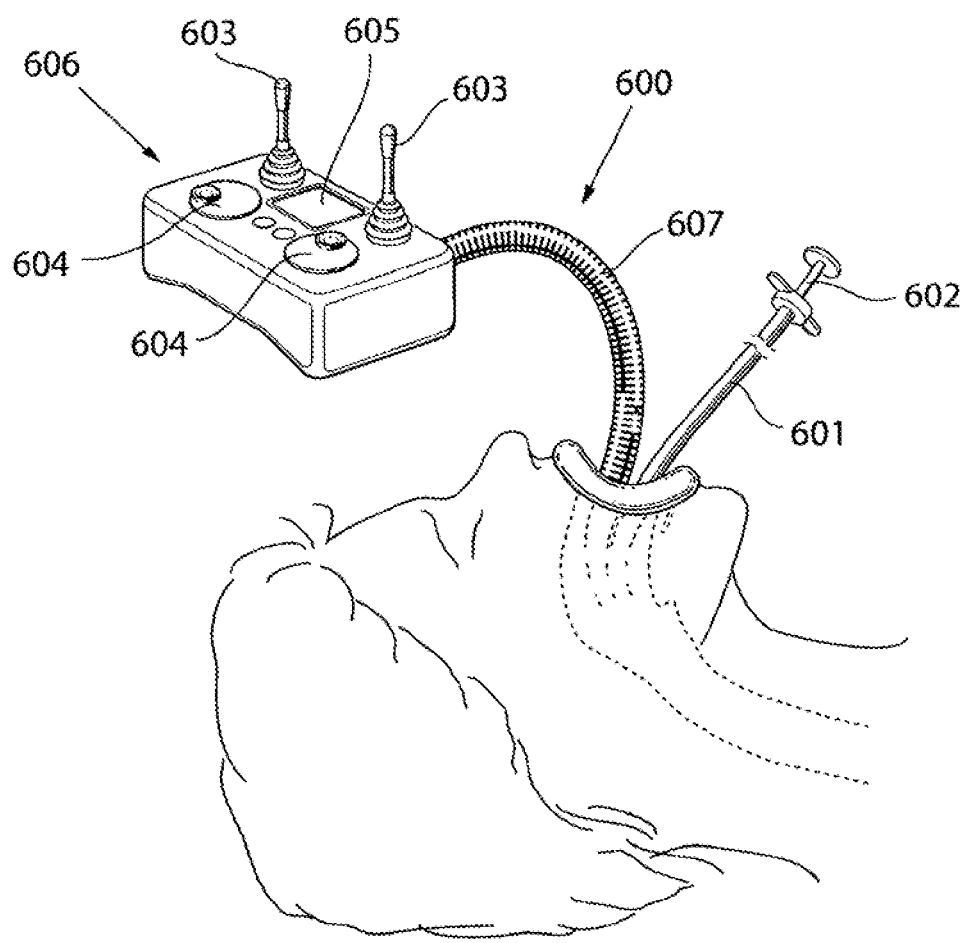
FIG. 37a shows the control unit of a gastroscopic instrument.
Figure 37B:
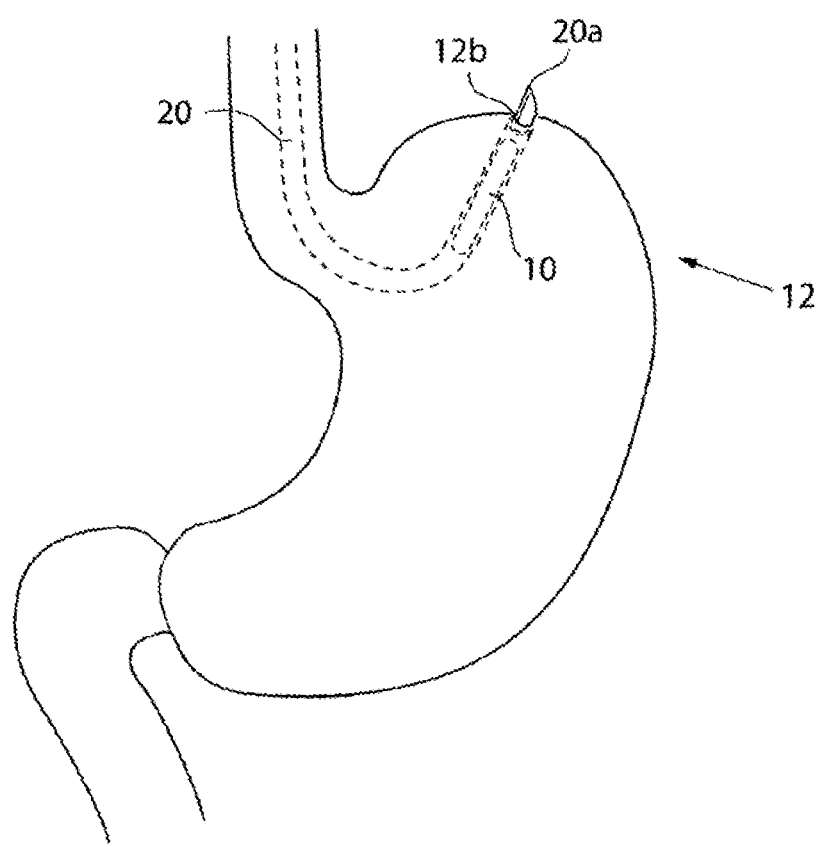
FIG. 37b shows the gastroscopic instrument when placed in the stomach.

The instrument is further inserted into the esophagus and into the stomach of the patient, sees FIG. 37*b*. By means of the instrument 600, a hole 12*b* is created in the wall of the stomach 12. To this end, the instrument is provided with one or more cutters 615 at the distal end thereof. These cutters can of course be designed in different ways, such as a toothed drum cutter rotating about the center axis of the tube-like instrument.

Figure 37C:
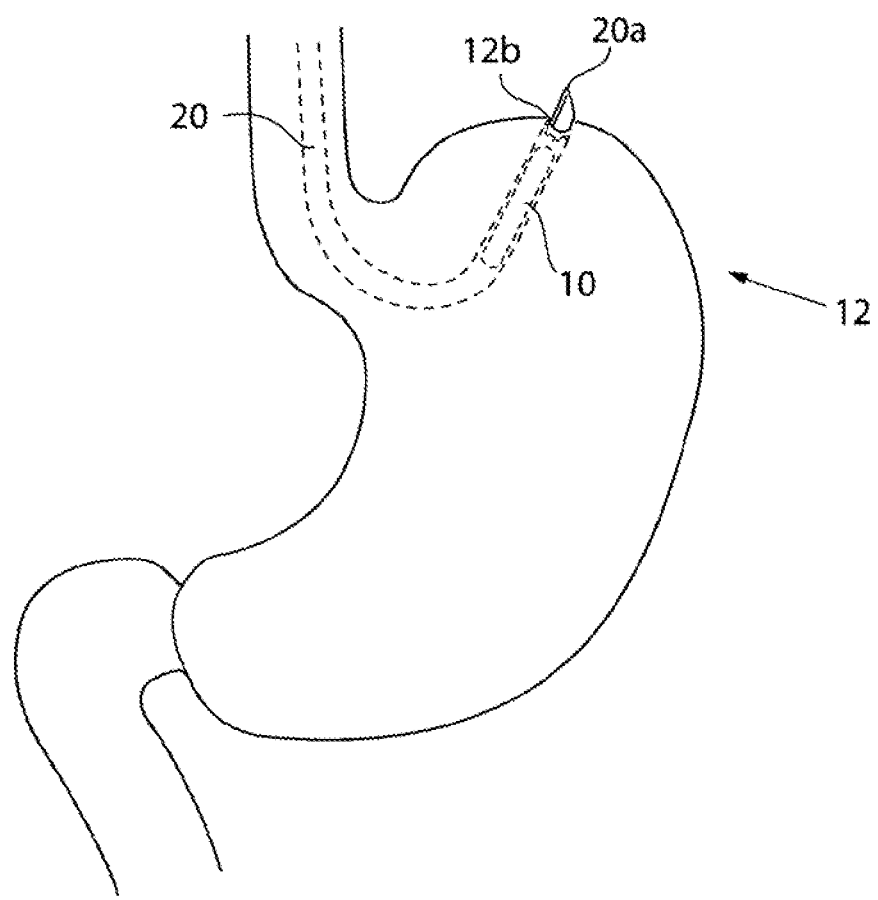
FIG. 37c shows the gastroscopic instrument when penetrating the stomach wall.
Figure 37D:
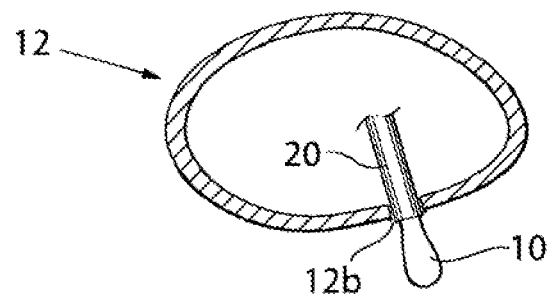
FIG. 37d shows the gastroscopic instrument when penetrating the stomach wall, in greater detail.
Figure 37E:
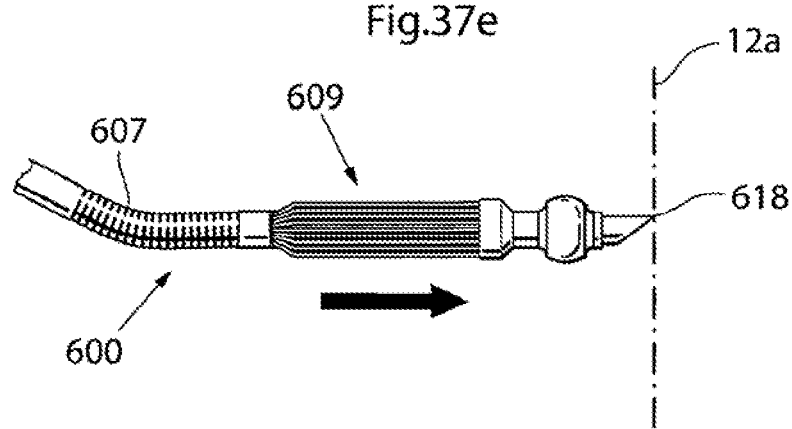
FIG. 37e shows a gastroscopic or laparoscopic instrument according to one embodiment.
Figure 37F:
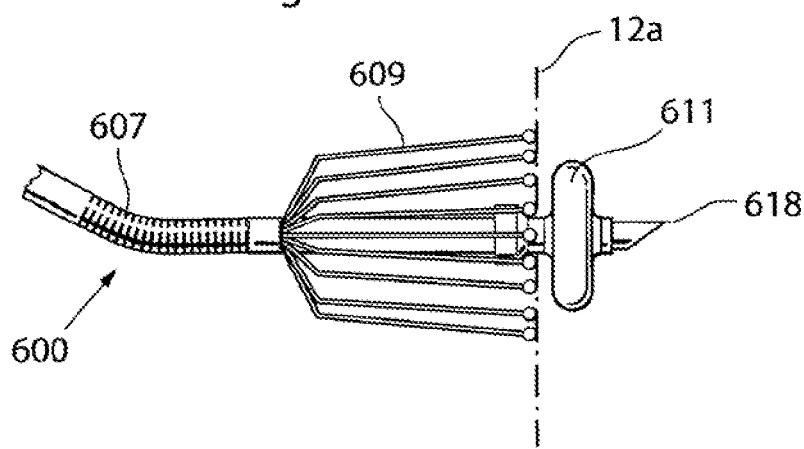
FIG. 37f shows a gastroscopic or laparoscopic instrument according to one embodiment, in a second state.

After cutting a hole in the stomach wall, the distal end of the instrument 600 is inserted into and through the hole 2*b* so that it ends up outside the stomach wall 12a. This is shown in FIG. 37c, showing a side view of the stomach 12, and FIG. 37d, which is a sectional view through the stomach of FIG. 37c taken along the lines Vd-Vd.

The instrument 600 is adapted to create a "cavity" or "pouch" on the outside of the stomach around the hole 12b in the stomach wall 12. Such an instrument and the method of providing the pouch will now be described.

FIGS. 37e-i show a gastroscopic or laparoscopic instrument for invaginating a stretching device 100 in the stomach wall 12 of the patient by creating a pouch of stomach wall 12 material in which the stretching device 10 is placed. The instrument, generally designated 600, and which may comprise the features described above with reference to FIGS. 4a-d, comprises an elongated member 607 having a proximal end and a distal end, the elongated member 607 having a diameter less than that of the patient's esophagus and being flexible such as to allow introduction of the flexible elongated member 607 with its distal end first through the patient's throat, esophagus and into the stomach 12 to the stomach wall 12a.

The stomach penetration device or cutter 615 is provided on the elongated member 607 at the distal en thereof for penetrating the stomach wall 12a so as to create a hole in the stomach wall 12a, to allow introduction of the elongated member 607 through the hole. The stomach penetration device 615 could be adapted to be operable for retracting said stomach penetration device 615 after the stomach fundus wall 12a has been penetrated, for not further damaging tissue within the body. The instrument further comprises a special holding device 609 provided on the elongated member 607 on the proximal side to the penetration device 615.

The elongated member further comprises an expandable member 611 which is adapted to be expanded after the elongated member has penetrated the stomach wall 12a and thereby assist in the creation of a cavity or pouch adapted to hold the volume filling device 610. The expandable member 611 may comprise an inflatable circular balloon provided circumferentially around the distal end portion of the flexible elongated member 607.

The method steps when invaginating the volume filling device will now be described in detail. After the instrument 600 has been inserted into the stomach 12, the stomach penetration device 615 is placed into contact with the stomach wall 12, see FIG. 37e. The stomach penetration device or cutter 615 is then brought to create the hole 12b in the stomach wall, whereafter at least the expandable member 611 is brought through the hole 12b in the stomach wall. The special holding device 609 is in this step brought to a holding state wherein it expands radially so as to form an essentially circular abutment surface to the stomach wall 12, see FIG. 37f. In this way, the insertion of the stomach penetration device 615 and the expandable member 611 through the hole 12 in the stomach wall is limited to the position shown in FIG. 37f.

The expandable member 611 is then expanded. In the case the expandable member comprises a balloon or the like, air or other fluid is injected into it.

Figure 37G:
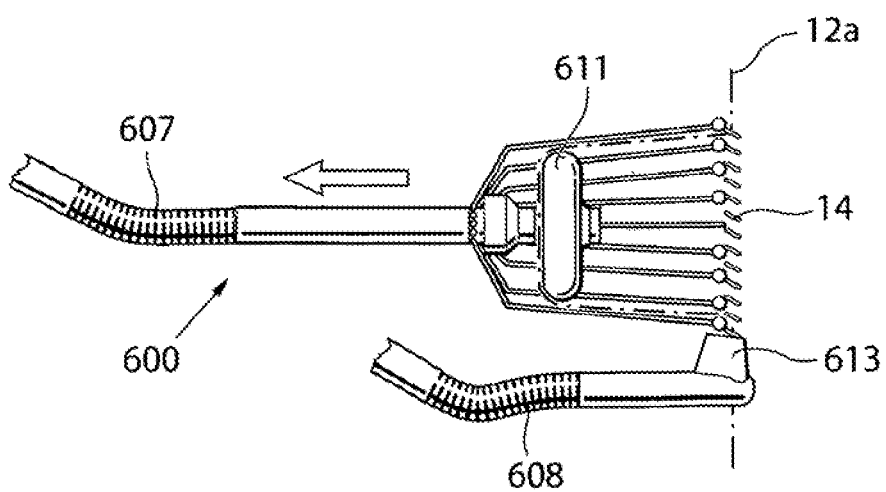
FIG. 37g shows a gastroscopic or laparoscopic instrument according to one embodiment, in a third state.

The part of the elongated member 607 comprising the expandable member 611 is then retracted in the proximal direction, as indicated by the arrow in FIG. 37g, thereby pulling the stomach wall 612 into a basket or cup like structure created by the special holding device 609.

A suturing or stapling device 608 is further provided, either as a device connected to the elongated member 607 or as a separate instrument. The suturing or stapling member comprises a suturing or stapling end 613 which is adapted to close the cavity or pouch by means of stomach to stomach sutures or staples 14.

Figure 37H:
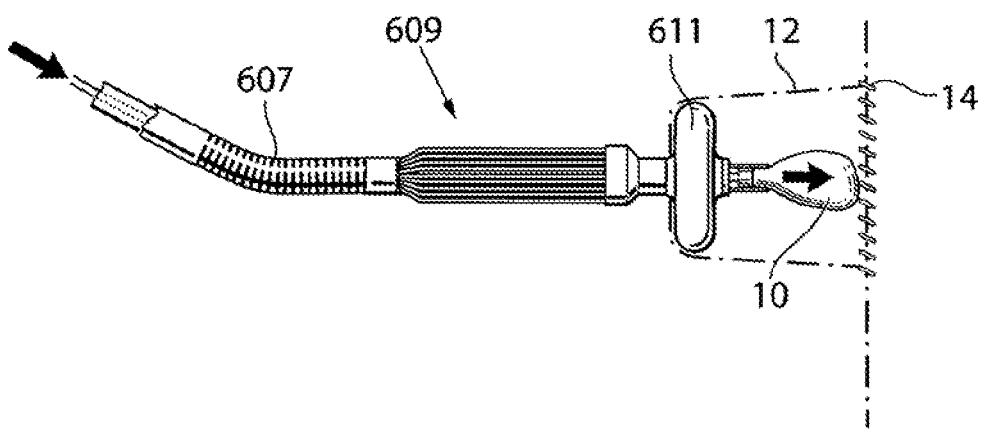
FIG. 37h shows a gastroscopic or laparoscopic instrument according to one embodiment, in a fourth state.
Figure 37I:
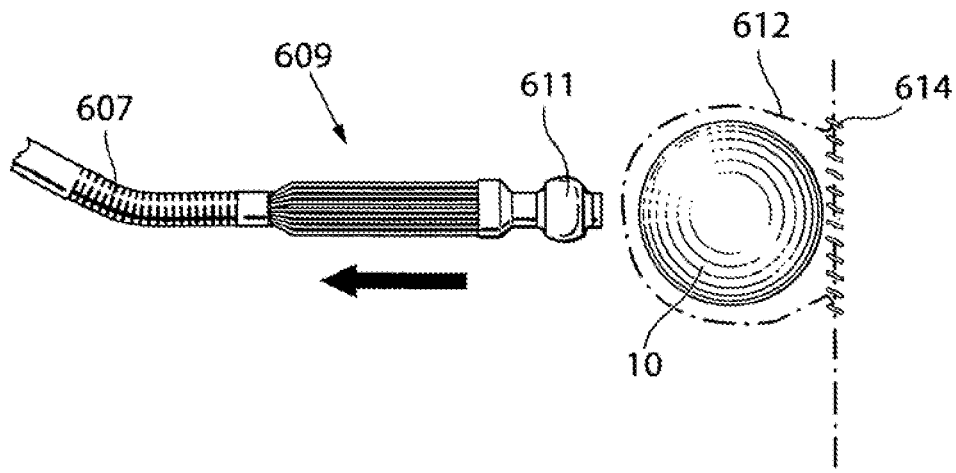
FIG. 37i shows a gastroscopic or laparoscopic instrument according to one embodiment, in a fifth state.

In a further step, illustrated in FIG. 37h, an inflatable stretching device 10 is placed in its deflated state in the cup like structure. The stretching device 10 is then inflated to its inflated or expanded state, see FIG. 37i. This inflation of the stretching device 10 can be accomplished by injecting a fluid or a gel into the deflated stretching device. It can also be accomplished by injecting a material which is allowed to cure, thereby forming a solid device 10. Thus, the stretching device 10 shown in FIGS. 37h and 37i can illustrate either a balloon-like device which is subsequently filled with fluid or gel or alternatively a material which is simply injected into the cup like structure formed by the stomach wall 12.

The fluid which is used to fill the stretching device 10 could be any suitable fluid suitable to fill the stretching device 10, such as a salt solution. In another embodiment, when this fluid is a fluid which is adapted to be transformed into solid state, the fluid could be liquid polyurethane.

In order to minimize or entirely eliminate leakage, the fluid is iso-tonic, i.e., it has the same osmolarity as human body fluids. Another way of preventing diffusion is to provide a fluid which comprises large molecules, such as iodine molecules.

The stomach-to-stomach sutures or staples 14 are preferably provided with fixation portions exhibiting a structure, such as a net like structure, adapted to be in contact with the stomach wall 12 to promote growth in of human tissue to secure the long term placement of the stretching device attached to the stomach wall.

Thereby is the inflatable stretching device 10 in its inflated or expanded state invaginated by a stomach wall portion of the patient on the outside of the stomach wall 12.

During one or more of the above described steps, the stomach may be inflated with gas, preferably by means of the gastroscopic instrument.

The stretching device 10 described above with reference to FIGS. 37a-i has been described as an inflatable stretching device. It will be appreciated that it also can be an elastic stretching device with an elasticity allowing compression so as to be inserted into a gastroscopic instrument and which expands to an expanded state after leaving the instrument.

In one embodiment, the stretching device 10 comprises an inflatable stretching device 10 expandable to an expanded state. In this case, the inflatable stretching device 10 is provided with an inlet port 18b for a fluid and is adapted to be connected to a gastroscopic instrument. This embodiment will now be described in detail with reference to FIGS. 38a-38d.

Figure 38A:
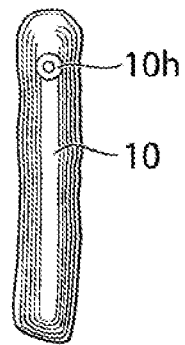
FIG. 38a-d shows a gastroscopic or laparoscopic instrument in greater detail.
Figure 38B:
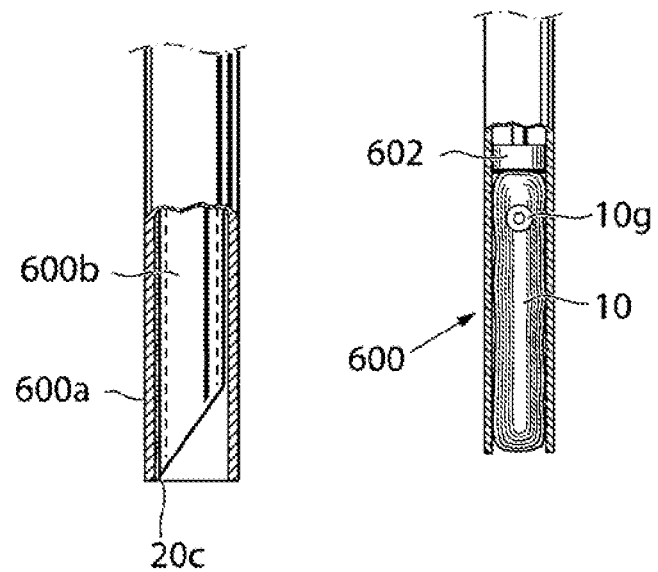

An inflatable stretching device in its non-expanded state is shown in FIG. 38a. It is essentially a balloon-like, deflated stretching device 10 having an inlet port 18b. In this state, the inflatable stretching device 10 has a diameter of a few millimeters at the most, allowing it to be inserted into the stomach through the esophagus of the patient by means of a gastroscopic, tube-like instrument 600, or through a laparoscopic trocar in an abdominal laparoscopic method using a tube like instrument 600 depicted in FIG. 38b. The instrument comprises an outer sleeve 600a and an inner sleeve 600b which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

Figure 38C:
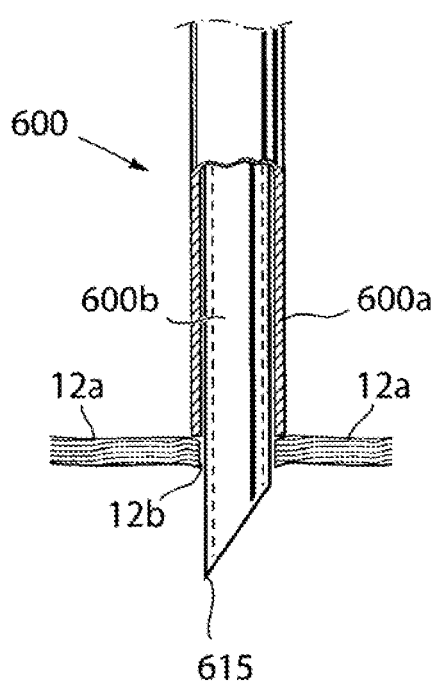
Figure 38D:
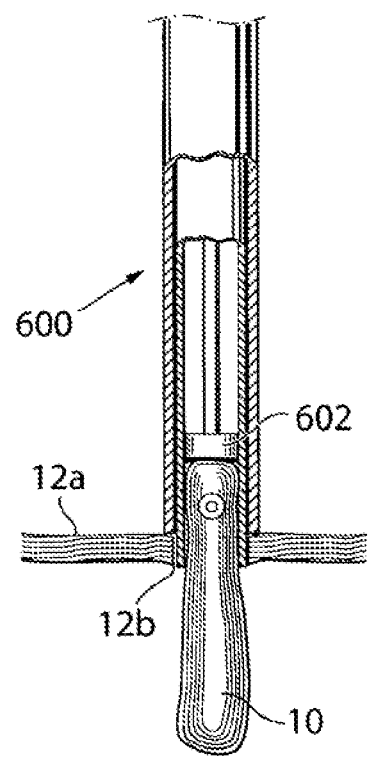

When the instrument reaches a stomach wall, from the inside or outside thereof, see FIG. 38c, the inner sleeve is brought forward from its position in the outer sleeve and into contact with the stomach wall 12a. The cutting edge 615 of the inner sleeve then cuts a hole in the stomach wall so as to allow subsequent insertion of the volume filling device 10 into and through this hole, see FIG. 38d. In order to push the stretching device through the hole, a piston 602 may be provided in the instrument. Thus, the instrument further comprises a piston 602 adapted for pushing a deflated stretching device 10 out from a position in the inner sleeve, this position being shown in FIG. 38b, to a position outside of the inner sleeve, this being shown in FIG. 38d. In order to protect the deflated stretching device 10 from the cutting edge 615 of the inner sleeve, a further protective sleeve (not shown) can be provided around the stretching device.

Figure 39A:
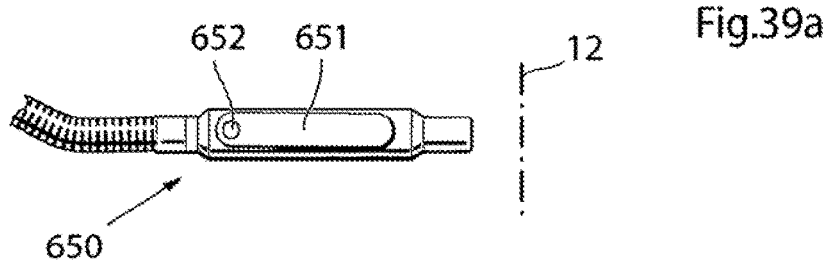
FIG. 39a-j shows a gastroscopic or laparoscopic instrument creating a cavity or pocket in the stomach wall and inserting a stretching device.
Figure 39B:
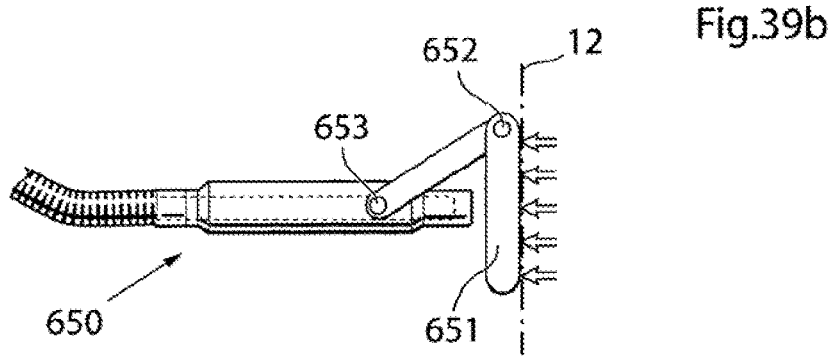
Figure 39C:
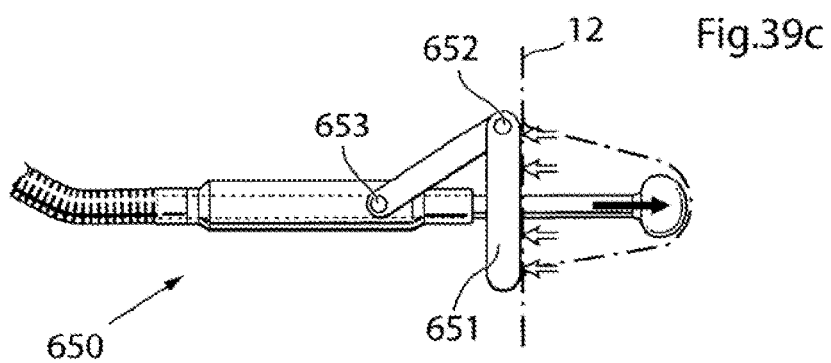
Figure 39D:
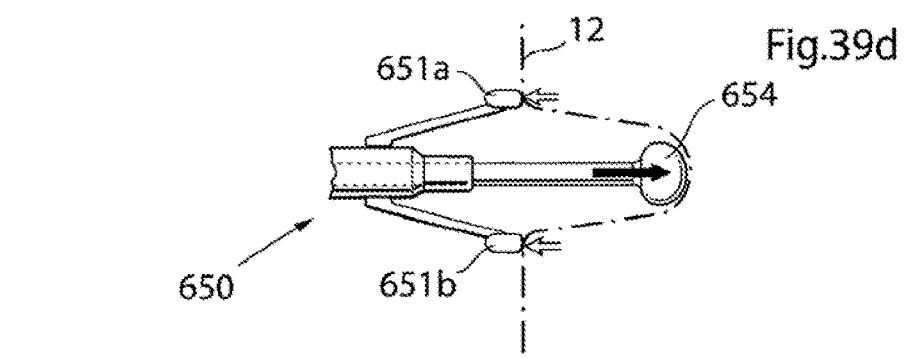
Figure 39E:
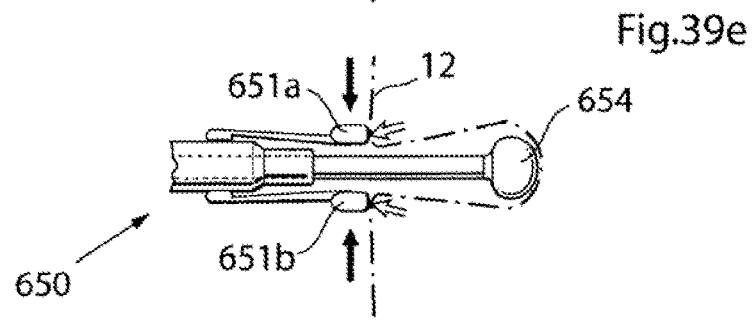

FIG. 39a-j shows an instrument for use in a method of engaging a stretching device 10 to the stomach wall 12 of a patient. The instrument is adapted to be inserted through a narrow tube shaped object such as a gastroscope, used in an intraluminal procedure, or a laparoscopic trocar used in a laparoscopic procedure. The instrument comprises an elongated member 650 which is adapted to be flexible by means of a construction comprising multiple ring shaped members, however it is equally conceivable that said elongated member 650 is adapted to be flexible by means of said elongated member 650 being made of a flexible or adjustable material. The elongated member 650 is inserted into the body and placed in proximity to the stomach wall 12 of the patient, from the outside or inside thereof. The elongated member 650 has a special holding device 651 adapted to hold the stomach by means of mechanical grabbing members or vacuum. The special holding device 651 comprises a first joint 652 and a second joint 653, which enables the special holding device 651 be operable in relation to the elongated member 650 and thereby place the part of the holding device 651 comprising the mechanical grabbing members or vacuum elements in contact with the stomach wall 12 of the patient. FIG. 39b shows the special holding device 651 when placed in contact with the stomach wall 12 of the human patient, after which the special holding member 651 connects to the stomach wall 12, for holding the stomach wall 12. FIG. 39c shows the instrument when the step of advancing a pushing rod 654 from the elongated member 650 is performed. The pushing rod 654 pushes the stomach wall 12 to create a cavity or pouch thereof. FIG. 39d shows the instrument turned 90° in relation to FIGS. 39a-c. This view shows the special holding members 651a,b operably attached to two sides of the elongated member 650 and being in contact with the stomach wall 12, holding the stomach wall 12 as the pushing rod 654 pushes to create a cavity or pouch. When the pushing rod 654 has pushed the stomach wall 12 to a desired position the special holding devices 651a,b moves towards the pushing rod 654 and thereby closes the cavity or pouch.

Figure 39F:
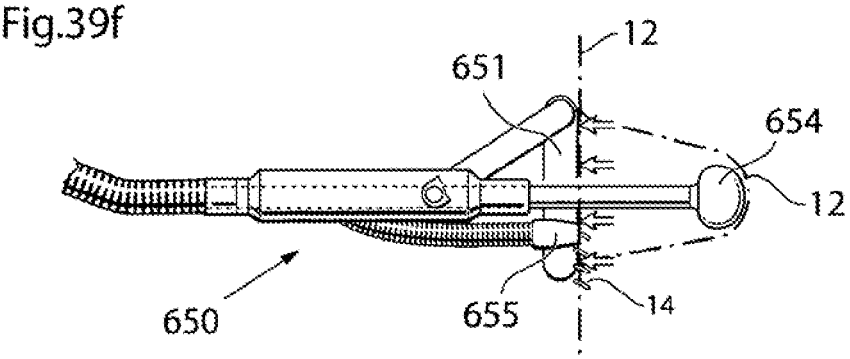
Figure 39G:
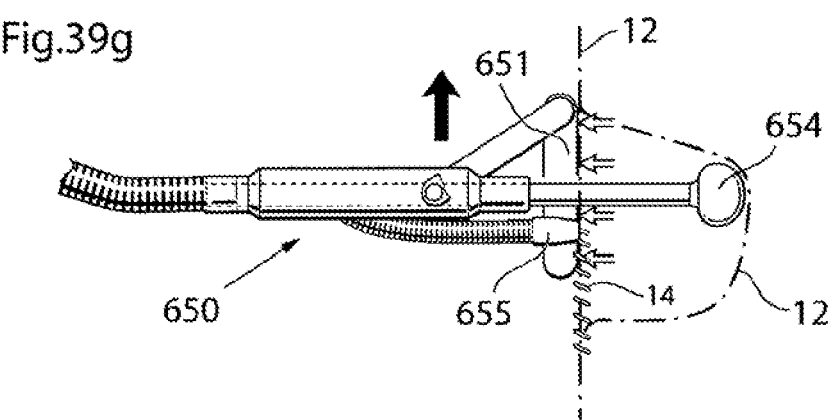
Figure 39H:
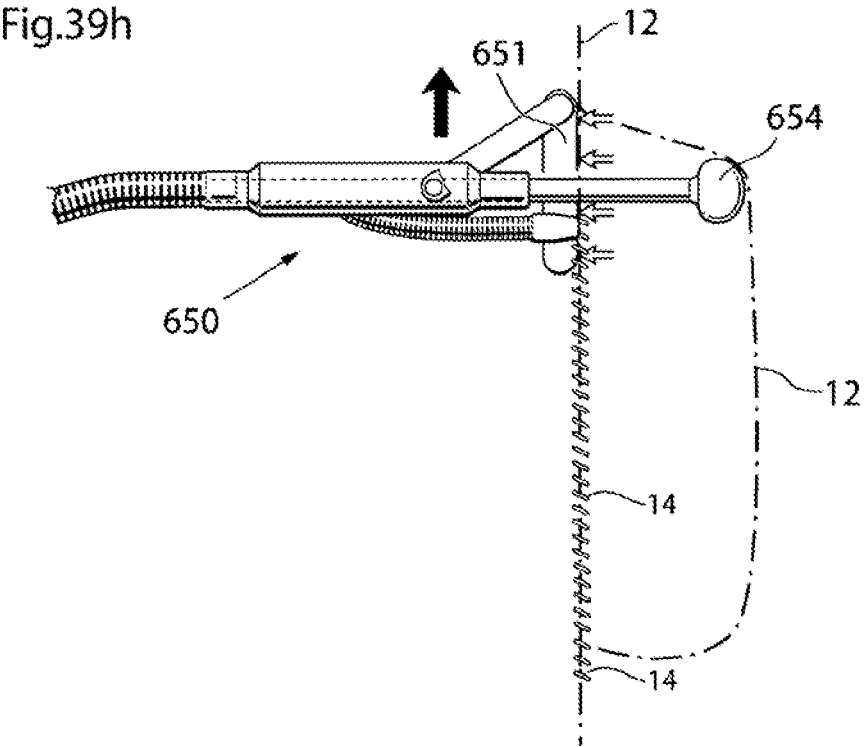
Figure 39I:
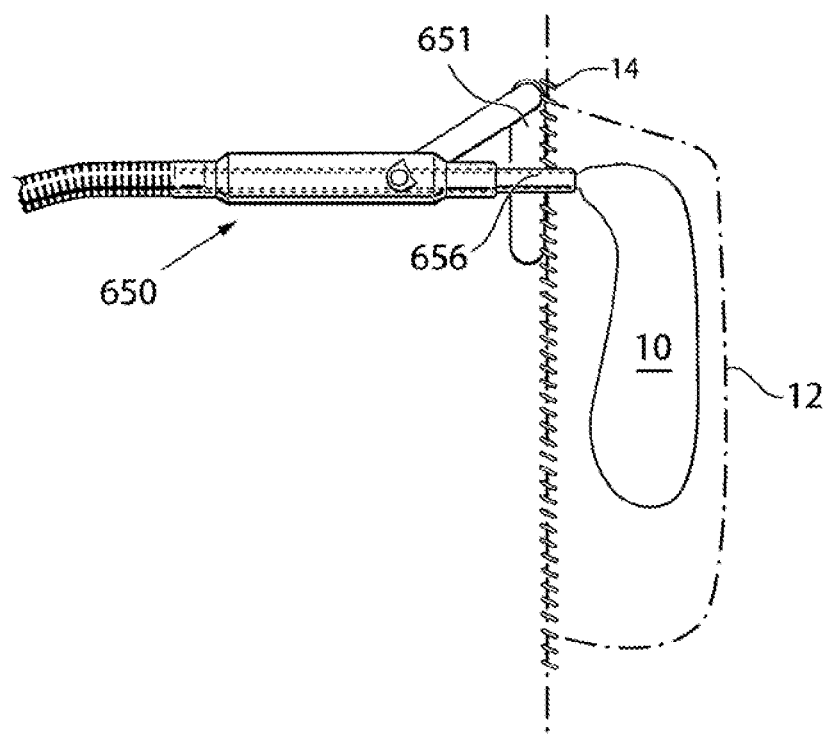
Figure 39J:
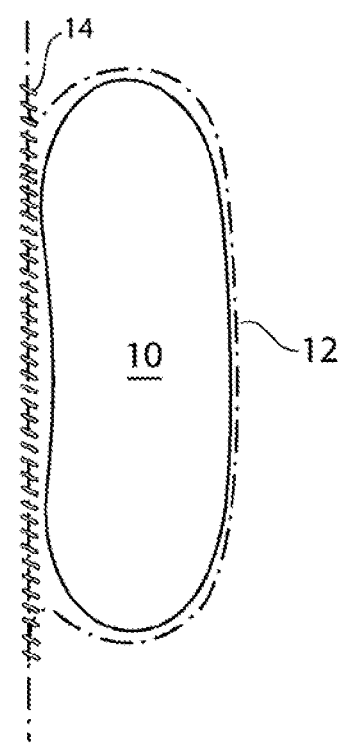

After the cavity or pouch has been created it needs to be sealed. FIG. 39f shows the advancement of a suturing or stapling device 655 from the elongated member 650. The suturing or stapling device 655 is positioned in connection with the stomach wall after which the suturing or stapling device commences with the suturing or stapling of the stomach wall 12, creating a seal of stomach to stomach sutures or staplers 14. The instrument is moved along the stomach wall 12 of the patient and thereby a cavity or pouch is created and sealed using the instrument, as shown in FIGS. 39g and 39h. When a cavity or pouch or desired size has been created and sealed an inserting member 656 is advanced from the elongated member 650. The inserting member 656 is adapted to insert a stretching device 10 being inflatable, as described earlier in this application. After the inserting member 656 has been positioned in the cavity or pouch the stretching device 10 is inserted through the inserting member 656 and into the cavity or pouch by means of a pressurized fluid or gas, or a mechanical advancement member pushing said inflatable stretching device 10 into the cavity or pouch. The insertion member then inflates the inflatable stretching device with a fluid or gas and seals of the final section of the pouch using stomach to stomach sutures or staplers 14. The embodiment described explains the process of inserting an inflatable stretching device, however it is equally conceivable that the stretching device 10 is expandable by means of the stretching device 10 being made of an elastic material.

Figure 40A:
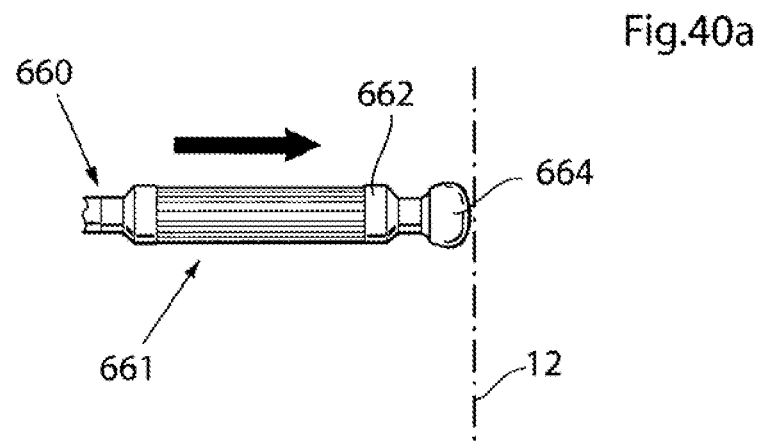
FIG. 40a-f shows a gastroscopic or laparoscopic instrument creating a cavity or pocket in the stomach wall and inserting a stretching device.
Figure 40B:
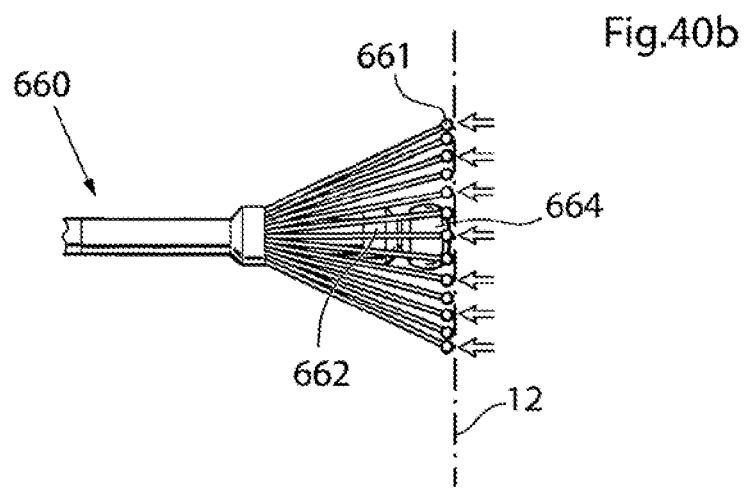
Figure 40C:
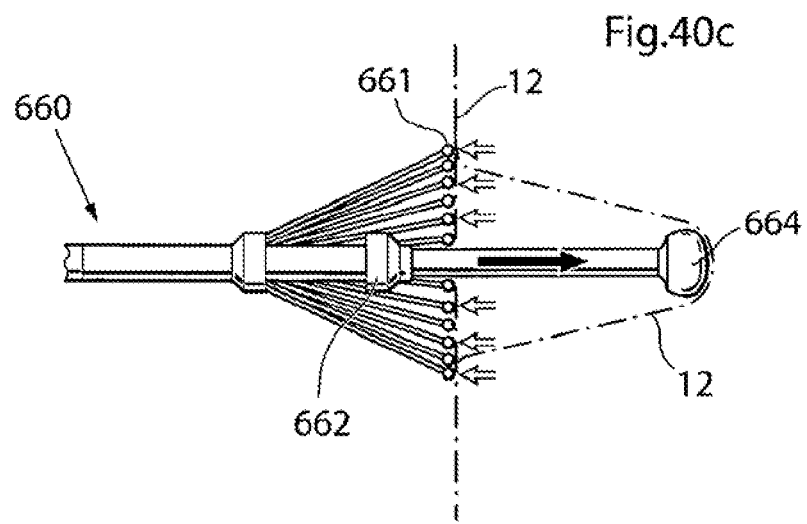

FIG. 40a-f shows an instrument for use in a method of engaging a stretching device 10 to the stomach wall 12 of a patient. The instrument is adapted to be inserted through a narrow tube shaped object such as a gastroscope, used in an intraluminal procedure, or a laparoscopic trocar used in a laparoscopic procedure. The instrument comprises an elongated member 660 which is adapted to be flexible by means of a construction comprising multiple ring shaped members, however it is equally conceivable that said elongated member 660 is adapted to be flexible by means of said elongated member 660 being made of a flexible or adjustable material. The elongated member 660 is inserted into the body and placed in proximity to the stomach wall 12 of the patient, from the outside or inside thereof. The elongated member 660 has multiple special holding devices 661 adapted to hold the stomach by means of mechanical grabbing members or vacuum. The special holding devices 661 are locked in a position alongside the elongated member 660 by means of a locking ring 662. The special holding devices are made of a flexible material end pre-bent to expand into a funnel-shaped device when said locking ring 662 is removed. The special holding device in its funnel shaped expandable state is shown in FIG. 40b. FIG. 40b further shows the special holding device 661 when placed in contact with the stomach wall 12 of the human patient, after which the special holding member 661 connects to the stomach wall 12, for holding the stomach wall 12. FIG. 40c shows the instrument when the step of advancing a pushing rod 664 from the elongated member 660 is performed. The pushing rod 664 pushes the stomach wall 12 to create a cavity or pouch thereof. When the pushing rod 664 has pushed the stomach wall 12 to a desired position the special holding devices 661 moves towards the pushing rod 664 and thereby closes the cavity or pouch.

Figure 40D:
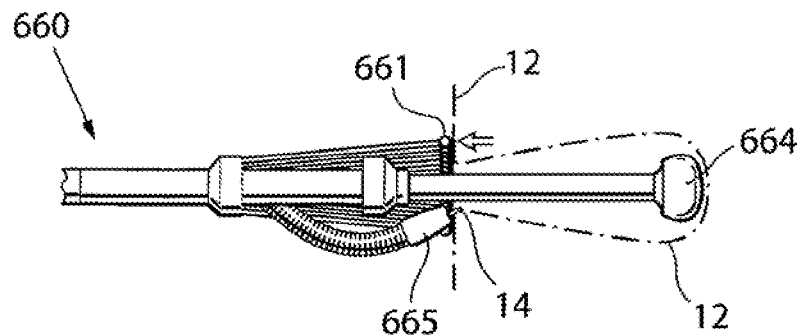
Figure 40E:
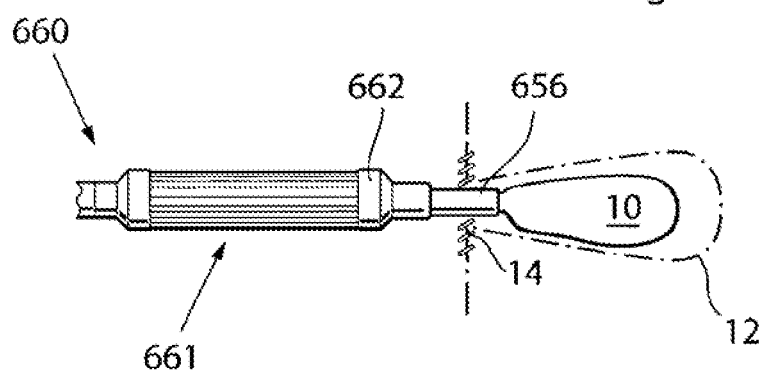
Figure 40F:
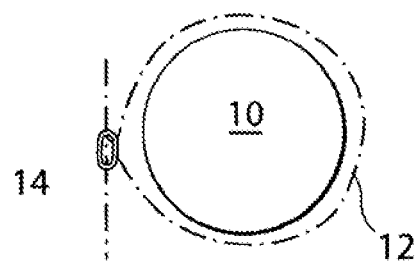

After the cavity or pouch has been created it needs to be sealed. FIG. 40d shows the advancement of a suturing or stapling device 665 from the elongated member 660. The suturing or stapling device 665 is positioned in connection with the stomach wall 12 after which the suturing or stapling device 665 commences with the suturing or stapling of the stomach wall 12, creating a seal of stomach to stomach sutures or staplers 14. Thereafter an inserting member 666 is advanced from the elongated member 660 and the special holding devices 661 are retracted. The inserting member 666 is adapted to insert a stretching device 10 being inflatable, as described earlier in this application. After the inserting member 666 has been positioned in the cavity or pouch the stretching device 10 is inserted through the inserting member 666 and into the cavity or pouch by means of a pressurized fluid or gas, or a mechanical advancement member pushing said inflatable stretching device 10 into the cavity or pouch. The insertion member 656 then inflates the inflatable stretching device with a fluid or gas and seals of the final section of the pouch using stomach to stomach sutures or staplers 14. The embodiment described explains the process of inserting an inflatable stretching device 10, however it is equally conceivable that the stretching device 10 is expandable by means of the stretching device 10 being made of an elastic material. FIG. 40 *f* shows the stretching device 10 as the stretching device 10 is invaginated in the stomach wall 12, in a cavity or pouch sealed with stomach to stomach sutures or staplers 14.

Figure 41A:
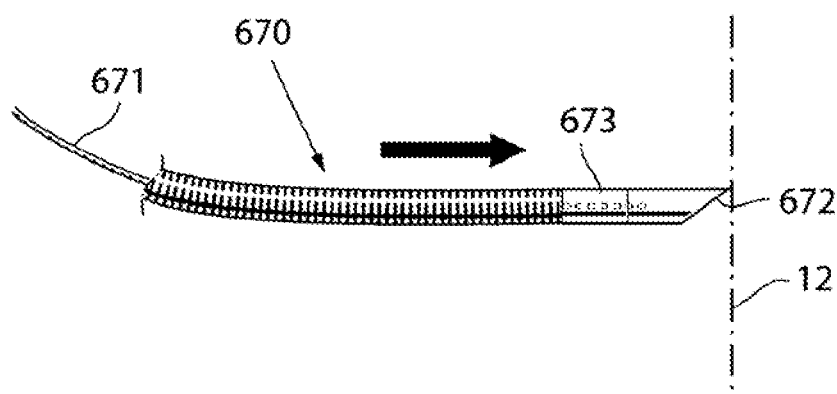
FIG. 41a,b shows a gastroscopic or laparoscopic instrument inserting a guiding wire.

FIG. 41*a* shows an instrument used in a method of engaging the stretching device according to any of the embodiments of the application to the stomach wall 12. The instrument comprises an elongated member 670 which is adapted to be flexible by means of a construction comprising multiple ring shaped members, however it is equally conceivable that said elongated member 670 is adapted to be flexible by means of said elongated member 670 being made of a flexible or adjustable material. The elongated member 670 is inserted into the body and placed in proximity to the stomach wall 12 of the patient, from the inside thereof. A stomach penetrating member 672 is placed in the distal end of the elongated member 670, retractably fixated to a protective sleeve 673 adapted to protect the tissue of the body from the sharp penetrating member 672 or cutter 672 after the cutting operation has been performed.

Figure 41B:
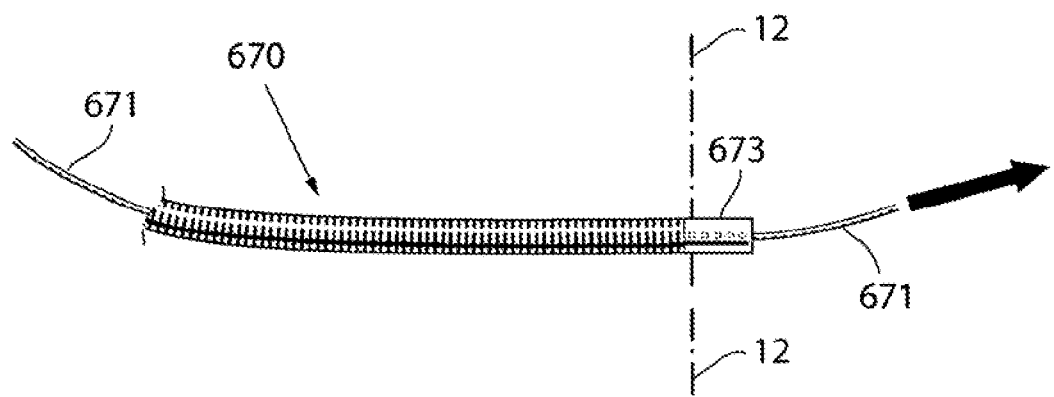

FIG. 41*b* shows the instrument comprising the elongated member 670 after the cutting operation has been performed and the stomach penetrating member or cutter 672 has been retracted into the protective sleeve 673. A guiding wire 671 is pushed through the elongated member 670, through the hole made in the stomach wall 12 and out through the abdomen and placed on the inside of the patients skin, which is penetrated from the outside to enable the guiding wire 671 to exit the abdomen. The guiding wire 671 can then be used to guide a conduit 18 or a lead attached to the stretching device 10 being placed in the stomach from the inside thereof. The stretching device 10 with the conduit 18 or electrical lead being a stretching device 10 according to any of the embodiments of this application. The guiding of the conduit 18 or electrical lead enables the attachment of the conduit 18 or electrical lead to a control unit 42 placed subcutaneously in the patient from the outside of the abdomen.

Figure 42:
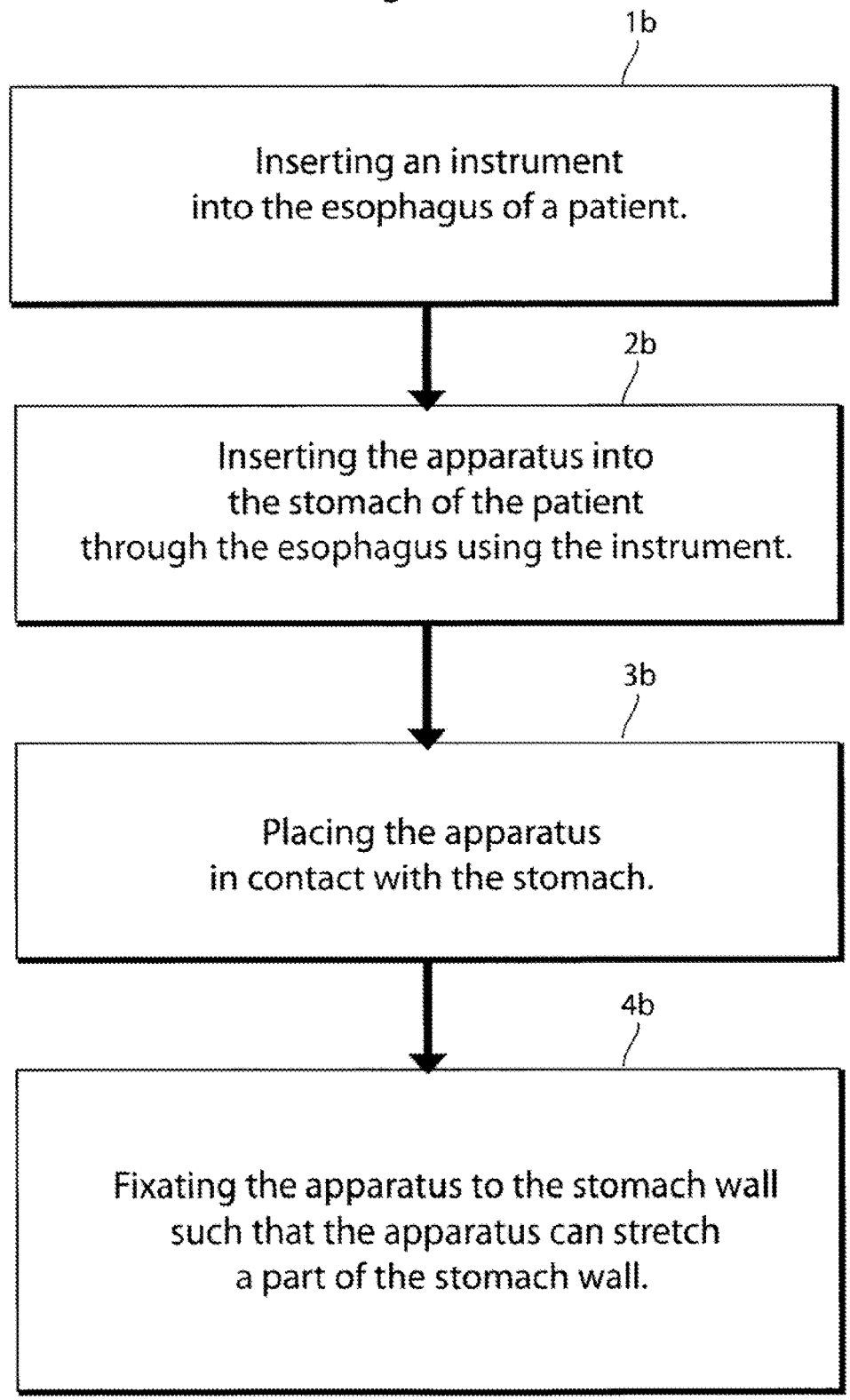
FIG. 42 shows a flowchart of a gastroscopic method.

FIG. 42 shows a flowchart describing the steps needed in an intraluminar method of inserting a device for stretching a portion of the stomach wall, the method comprises the steps of inserting an instrument into the esophagus 203 of the patient, step 1*a*, inserting a device into the stomach of the patient through the esophagus 203 using the instrument, step 2*a*, placing the device 10 in contact with the stomach wall 12, step 3*a*, fixating the device to the stomach wall 12 such that the device can stretch a part of the stomach wall 12. The method described could further comprise the step of non-invasively regulating the device after the placing of the device has been completed.

Figure 43:
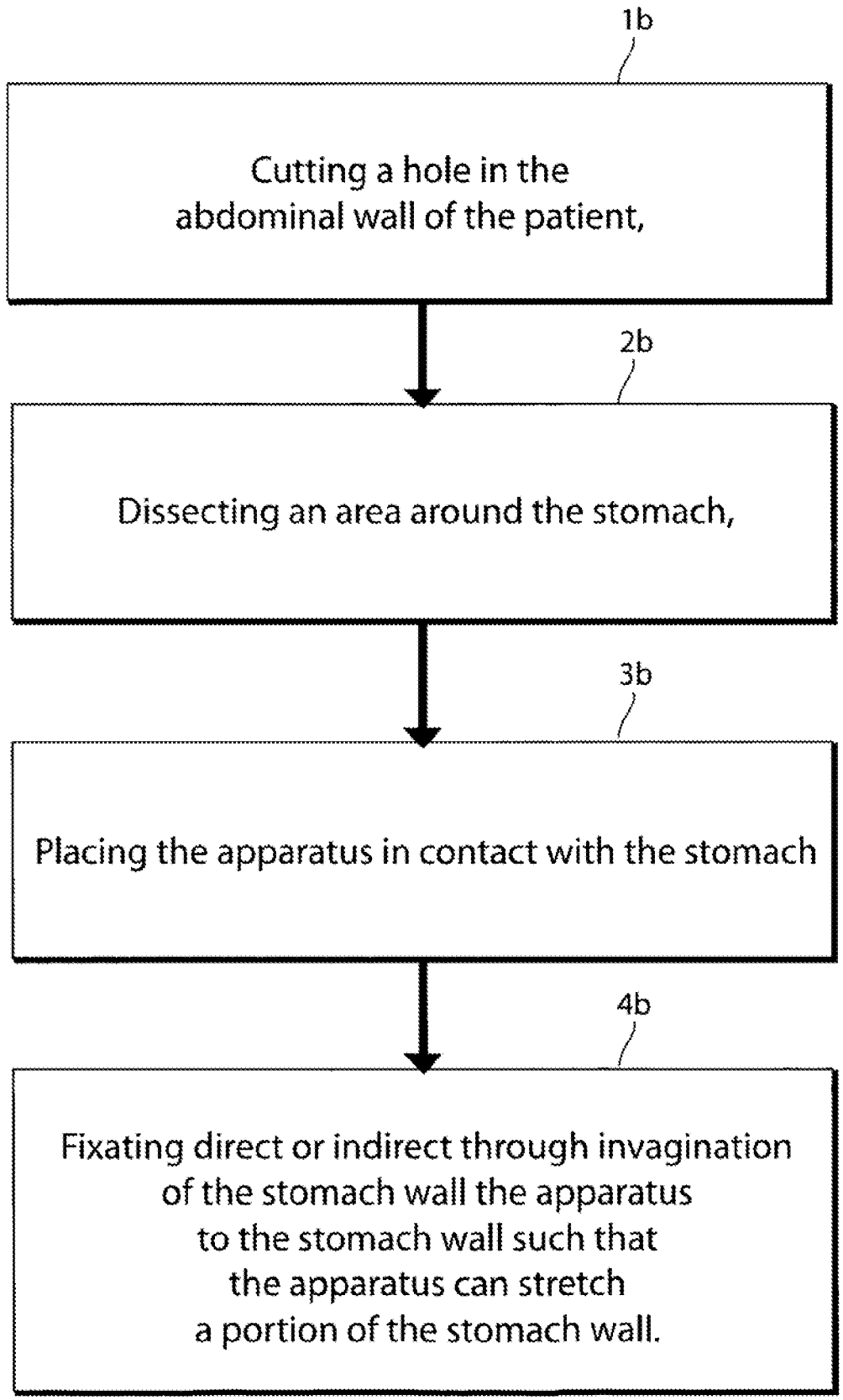
FIG. 43 shows a flowchart of a laparoscopic or surgical method.

FIG. 43 shows a flowchart describing the steps needed in an abdominal method of inserting a device for stretching a portion of the stomach wall, the method comprises the steps of cutting a hole in the abdominal wall of said patient, step 1*b*, dissecting an area around the stomach, step 2*b*, placing said device in contact with the stomach, step 3*b* and fixating direct or indirect through invagination of the stomach wall the device to the stomach wall such that the device can stretch a portion of said stomach wall, step 4*b*. The method described could further comprise the steps of closing the hole in the abdomen using sutures or staplers 14 and non-invasively regulating the device after the placing of the device has been completed.

Please note that any embodiment or part of embodiment or feature or method or associated system or part of system described herein may be combined in any combination.

The invention claimed is:

1. A surgical or laparoscopic method of treating obesity of a human patient using a device adapted to be non-invasively operated for actively stretching a portion of the stomach wall of said patient, the device comprises a stretching device having a shape and size allowing the device to be invaginated by the stomach fundus of the patient, and a non-invasive operation device for actively stretching the stomach wall of the patient, the method comprising the steps of:
   cutting a hole in the abdominal wall of said patient using a surgical cutting instrument,
   dissecting an area around the stomach using a surgical dissection instrument,
   invaginating said device in the stomach of the patient using stomach-to-stomach sutures or staplers, and
   implanting the operation device such that the operation device can actively and non-invasively control the device to stretch the invaginated stomach wall, such that a feeling of satiety is created.

2. The surgical or laparoscopic method according to claim 1, wherein said device further comprises a subcutaneous switch connected to said operation device, and wherein the method further comprises placing the subcutaneous switch subcutaneously in the patient.

3. The surgical or laparoscopic method according to claim 1, wherein said method further comprises the step of implanting a sensor for sensing a variable related to the patient eating, said sensor being directly or indirectly connected to the operation device.

4. The surgical or laparoscopic method according to claim 2, wherein said method further comprises the step of:
   (a) sensing a variable using the implantable sensor,
   (b) interpreting said sensed variable,
   (c) using said interpreted variable to control the operation of the operation device to automatically and non-invasively stretch a portion of the stomach wall.

5. The surgical or laparoscopic method according to claim 1, wherein the step of cutting a hole in the abdominal wall in the skin comprises:
   inserting a tube or needle into the patient's body,
   filling the body through the tube or needle with a gas and thereby expanding a cavity within the patient's body,
   inserting at least two laparoscopic trocars into said cavity,
   inserting at least one camera through at least one laparoscopic trocar, and
   inserting at least one dissecting tool through at least one laparoscopic trocar.

6. The surgical or laparoscopic method according to claim 1, further comprising the step of implanting at least one of:
   an internal energy source, and
   a wireless energy receiver for non-invasively energizing the operable stretching device.

7. The surgical or laparoscopic method according to claim 1, further comprising placing a receiver of wireless energy, adapted to be directly or indirectly connected to the operation device, subcutaneously in the patient.

8. The surgical or laparoscopic method according to claim 1, further comprising placing an internal data communicator, adapted to wirelessly communicate with an external data communicator, subcutaneously in the patient.

9. The surgical or laparoscopic method according to claim 1, wherein said operation device is a hydraulic operation device, and wherein the method further comprises implanting a hydraulic pump in fluid connection with said operation device.

10. The surgical or laparoscopic method according to claim 9, further comprising placing a fluid reservoir in fluid connection with the hydraulic pump, in the abdomen of the patient.

11. The surgical or laparoscopic method according to claim 10, wherein operating said operation device comprises moving fluid from the fluid reservoir to the operation device using said hydraulic pump.

* * * * *